(12) United States Patent
Chen et al.

(10) Patent No.: US 9,255,257 B2
(45) Date of Patent: Feb. 9, 2016

(54) PMST1 MUTANTS FOR CHEMOENZYMATIC SYNTHESIS OF SIALYL LEWIS X COMPOUNDS

(75) Inventors: Xi Chen, Woodland, CA (US); Go Sugiarto, Davis, CA (US); Kam Lau, Parkwood (AU)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 170 days.

(21) Appl. No.: 14/237,334

(22) PCT Filed: Aug. 6, 2012

(86) PCT No.: PCT/US2012/049748
§ 371 (c)(1),
(2), (4) Date: Jun. 18, 2014

(87) PCT Pub. No.: WO2013/022836
PCT Pub. Date: Feb. 14, 2013

(65) Prior Publication Data
US 2014/0302565 A1    Oct. 9, 2014

Related U.S. Application Data

(60) Provisional application No. 61/515,702, filed on Aug. 5, 2011.

(51) Int. Cl.
*C12P 19/18* (2006.01)
*C12N 9/10* (2006.01)

(52) U.S. Cl.
CPC .......... *C12N 9/1077* (2013.01); *C12N 9/1081* (2013.01); *C12P 19/18* (2013.01); *C12Y 204/99* (2013.01)

(58) Field of Classification Search
None
See application file for complete search history.

(56) References Cited

U.S. PATENT DOCUMENTS

| | | |
|---|---|---|
| 5,374,541 A | 12/1994 | Wong et al. |
| 2005/0089956 A1 | 4/2005 | Endo et al. |
| 2007/0275908 A1 | 11/2007 | Defrees et al. |
| 2009/0215115 A1 | 8/2009 | Gilbert et al. |
| 2010/0291631 A1 | 11/2010 | Yamamoto et al. |

OTHER PUBLICATIONS

Audry et al., "Current trends in the structure-activity relationships of sialyltransferases," Glycobiology, 2011, vol. 21(6), pp. 716-726.
Chung et al., "Vaccination against fowl cholera with acapsular Pasteurella multocida A:1," Vaccine, 2005, 23: 2751-2755.
Coutinho et al., "An evolving hierarchical family classification for glycosyltransferases," J Mol Biol., 2003, vol. 328, pp. 307-317.
Gilbert et al., "Characterization of a recombinant Neisseria meningitides alpha-2,3-sialyltransferase and its acceptor specificity," Eur J Biochem., 1997, 249: 187-194.
Gilbert et al., "Cloning of the lipooligosaccharide alpha-2,3-sialyltransferase from the bacterial pathogens Neisseria meningitidis and Neisseria gonorrhoeae," J Biol Chem., 1996, 271:28271-28276.
Izumi et al., "Microbial glycosyltransferases for carbohydrate synthesis: Alpha-2,3-sialyltransferase from Neisseria gonorrheae," J Am Chem Soc., 2001, 123:10909-10918.
Kushi et al., "Sialyltransferases of marine bacteria efficiently utilize glycosphingolipid substrates," Glycobiology, 2010, 20:187-198.
Lairson et al.,"Glycosyltransferases: Structures, Functions, and Mechanisms," Annu. Rev. Biochem., 2008, vol. 77, pp. 521-555.
Larsson et al., "Synthesis of reference standards to enable single cell metabolomic studies of tetramethylrhodaminelabeled ganglioside GM1," Carbohydr Res., 2007, 342:482-489.
Li et al., "The Hd0053 gene of Haemophilus ducreyi encodes an alpha2,3-sialyltransferase," Biochem Biophys Res Commun, 2007, vol. 361(2), pp. 555-560.
Li et al., "Sialic acid metabolism and sialyltransferases: natural functions and applications," Appl. Microbiol. Biotechnol., 2012, vol. 94, pp. 887-905.
Liu et al., "A striking example of the interfacing of glycal chemistry with enzymatically mediated sialylation: A concise synthesis of ganglioside GM3," J Am Chem Soc., 1993, 115:4933-4934.
May et al., "Complete genomic sequence of Pasteurella multocida, Pm70," Proc Natl Acad Sci USA, 2001, 98:3460-3465.
Ni et al., "Cytidine 5'-monophosphate (CMP)-induced structural changes in a multifunctional sialyltransferase from Pasteurella multocida," Biochemistry, 2006, 45:2139-2148.
Nishimura et al., "Transfer of ganglioside GM3 oligosaccharide from a water soluble polymer to ceramide by ceramide glycanase. A novel approach for the chemical-enzymatic synthesis of glycosphingolipids," J Am Chem Soc., 1997, 119:10555-10556.
Steenbergen et al., "Sialic acid metabolism and systemic pasteurellosis," Infect Immun., 2005, 73:1284-1294.
St. Michael et al., "Structural analysis of the lipopolysaccharide from Pasteurella multocida genome strain Pm70 and identification of the putative lipopolysaccharide glycosyltransferases," Glycobiology, 2005, 15:323-333.
Yu et al., "A multifunctional Pasteurella multocida sialyltransferase: A powerful tool for the synthesis of sialoside libraries," J Am Chem Soc., 2005, 127:17618-17619.
Zehavi et al., "Enzymic glycosphingolipid synthesis on polymer supports. III. Synthesis of G(M3), its analog [NeuNAc alpha(2-3) Gal beta(1-4)Glc beta(1-3)Cer] and their lyso-derivatives," Glycoconjugate J., 1998, 15:657-662.
International Search Report & Written Opinion for PCT/US2012/063826 dated Apr. 8, 2013.
Cheng, et al., "Multifunctionality of *Campylobacter jejuni* sialyltransferase CstII: Characterization of GD3/GT3 oligosaccharide synthase, GD3 oligosaccharide sialidase, and trans-sialidase activities," *Glycobiology*, vol. 18(9), pp. 686-697 (2008).
Kakuta, et al., "Crystal structure of Vibrionaceae *Photobacterium* sp. JT-ISH-224 α2,6-sialyltransferase in a ternary complex with donor product CMP and acceptor substrate lactose: catalytic mechanism and substrate recognition," *Glycobiology*, vol. 18(1), pp. 66-73 (2008).
Kim, et al., "Structural analysis of sialyltransferase PM0188 from *Pasteurella multocida* complexed with donor analogue and acceptor sugar," *BMB Reports*, vol. 41(1), pp. 48-54 (2008).
International Search Report for PCT/US2012/049748, mailed Feb. 25, 2013, 4 pages.

*Primary Examiner* — Christian Fronda
(74) *Attorney, Agent, or Firm* — Kilpatrick Townsend and Stockton LLP

(57) ABSTRACT

The present invention provides mutants of PmST1 for the preparation of sialyl-Lewis$^x$ oligosaccharides, and other sialosides with decreased sialidase activity.

22 Claims, 12 Drawing Sheets

SEQUENCE LISTING

<160> NUMBER OF SEQ ID NOS: 38

<210> SEQ ID NO 1
<211> LENGTH: 388
<212> TYPE: PRT
<213> ORGANISM: Pasteurella multocida
<220> FEATURE:
<223> OTHER INFORMATION: delta21PmST1 glycosyltransferase family 80
      (GT80), GT80 sialyltransferase delta24PMST1

<400> SEQUENCE: 1

```
Met Lys Thr Ile Thr Leu Tyr Leu Asp Pro Ala Ser Leu Pro Ala Leu
1               5                   10                  15

Asn Gln Leu Met Asp Phe Thr Gln Asn Asn Glu Asp Lys Thr His Pro
            20                  25                  30

Arg Ile Phe Gly Leu Ser Arg Phe Lys Ile Pro Asp Asn Ile Ile Thr
        35                  40                  45

Gln Tyr Gln Asn Ile His Phe Val Glu Leu Lys Asp Asn Arg Pro Thr
    50                  55                  60

Glu Ala Leu Phe Thr Ile Leu Asp Gln Tyr Pro Gly Asn Ile Glu Leu
65                  70                  75                  80

Asn Ile His Leu Asn Ile Ala His Ser Val Gln Leu Ile Arg Pro Ile
```

85                  90                  95
Leu Ala Tyr Arg Phe Lys His Leu Asp Arg Val Ser Ile Gln Gln Leu
            100                 105                 110

Asn Leu Tyr Asp Asp Gly Ser Met Glu Tyr Val Asp Leu Glu Lys Glu
            115                 120                 125

Glu Asn Lys Asp Ile Ser Ala Glu Ile Lys Gln Ala Glu Lys Gln Leu
            130                 135                 140

Ser His Tyr Leu Leu Thr Gly Lys Ile Lys Phe Asp Asn Pro Thr Ile
145                 150                 155                 160

Ala Arg Tyr Val Trp Gln Ser Ala Phe Pro Val Lys Tyr His Phe Leu
                165                 170                 175

Ser Thr Asp Tyr Phe Glu Lys Ala Glu Phe Leu Gln Pro Leu Lys Glu
                180                 185                 190

Tyr Leu Ala Glu Asn Tyr Gln Lys Met Asp Trp Thr Ala Tyr Gln Gln
                195                 200                 205

Leu Thr Pro Glu Gln Gln Ala Phe Tyr Leu Thr Leu Val Gly Phe Asn
            210                 215                 220

Asp Glu Val Lys Gln Ser Leu Glu Val Gln Gln Ala Lys Phe Ile Phe
225                 230                 235                 240

Thr Gly Thr Thr Thr Trp Glu Gly Asn Thr Asp Val Arg Glu Tyr Tyr
                245                 250                 255

Ala Gln Gln Gln Leu Asn Leu Leu Asn His Phe Thr Gln Ala Glu Gly
                260                 265                 270

Asp Leu Phe Ile Gly Asp His Tyr Lys Ile Tyr Phe Lys Gly His Pro
            275                 280                 285

Arg Gly Gly Glu Ile Asn Asp Tyr Ile Leu Asn Asn Ala Lys Asn Ile
            290                 295                 300

Thr Asn Ile Pro Ala Asn Ile Ser Phe Glu Val Leu Met Met Thr Gly
305                 310                 315                 320

Leu Leu Pro Asp Lys Val Gly Gly Val Ala Ser Ser Leu Tyr Phe Ser
                325                 330                 335

Leu Pro Lys Glu Lys Ile Ser His Ile Ile Phe Thr Ser Asn Lys Gln
                340                 345                 350

Val Lys Ser Lys Glu Asp Ala Leu Asn Asn Pro Tyr Val Lys Val Met
            355                 360                 365

Arg Arg Leu Gly Ile Ile Asp Glu Ser Gln Val Ile Phe Trp Asp Ser
            370                 375                 380

Leu Lys Gln Leu
385

<210> SEQ ID NO 2
<211> LENGTH: 1182
<212> TYPE: DNA
<213> ORGANISM: Pasteurella multocida
<220> FEATURE:
<223> OTHER INFORMATION: delta21PmST1 glycosyltransferase family 80
      (GT80), GT80 sialyltransferase delta24PmST1

<400> SEQUENCE: 2
atgaaaacaa tcacgctgta tttagatcct gcctccttac cggcattaaa tcagctgatg      60
gactttacgc aaaataatga agataaaaca catccacgta ttttggtct ttctcgcttt     120 aaaatccctg acaacattat tacacagtat caaaatatcc atttcgtcga actcaaagat     180
aatcgtccca ctgaagcact ttttacgatt ttagatcaat accctggtaa cattgagtta     240
aatatacact taaatattgc tcattccgtt caattaattc gtccgatttt ggcatatcgt     300

```
tttaaacatt tagatcgtgt atcaattcag cagttaaatc tttatgacga tggctcaatg      360
gaatatgttg atttagaaaa agaagaaaat aaagatattt ccgcagaaat taagcaagca      420
gaaaaacaac tttctcacta tttgcttact ggcaaaataa aatttgataa cccaactatt      480
gctcgttatg tctggcaatc cgcgttccca gtaaaatatc attttttaag tacagactat      540
tttgaaaaag ccgaattttt acaaccacta aaagaatatt tagcagaaaa ttatcaaaaa      600
atggactgga ctgcttacca acagctgact ccagaacagc aagcattcta cttaacattg      660
gtaggcttca atgacgaagt caagcagtcg ctagaagtgc aacaagctaa atttatcttt      720
accggcacga caacttggga aggaaatacc gatgtgcgag aatactacgc acagcaacaa      780
cttaatttac ttaatcactt tacccaagct gagggcgatt tatttattgg tgatcattat      840
aaaatctact ttaagggca tcctagaggt ggtgaaatta atgactacat tctgaacaat      900
gctaaaaata tcaccaatat ccctgccaat atttcctttg aagtattgat gatgacaggc      960
ttattacctg ataaagtggg tggtgttgca agttcactgt atttctcctt accaaaagaa     1020
aaaattagcc atattatttt cacatcgaat aaacaagtga aaagcaaaga agatgcgcta     1080
aataatccgt atgttaaggt catgcgtcgt ttaggtataa ttgacgaatc acaagtcatc     1140
ttttgggaca gtttaaaaca gttgggtgga ggtctcgagt ga                        1182
```

<210> SEQ ID NO 3
<211> LENGTH: 393
<212> TYPE: PRT
<213> ORGANISM: Artificial Sequence
<220> FEATURE:
<223> OTHER INFORMATION: synthetic delta21PmST1 glycosyltransferase
      family 80 (GT80) M120D mutant having decreased alpha2-3
      sialidase activity

<400> SEQUENCE: 3

```
Met Lys Thr Ile Thr Leu Tyr Leu Asp Pro Ala Ser Leu Pro Ala Leu
  1               5                  10                  15

Asn Gln Leu Met Asp Phe Thr Gln Asn Asn Glu Asp Lys Thr His Pro
             20                  25                  30

Arg Ile Phe Gly Leu Ser Arg Phe Lys Ile Pro Asp Asn Ile Ile Thr
         35                  40                  45

Gln Tyr Gln Asn Ile His Phe Val Glu Leu Lys Asp Asn Arg Pro Thr
     50                  55                  60

Glu Ala Leu Phe Thr Ile Leu Asp Gln Tyr Pro Gly Asn Ile Glu Leu
 65                  70                  75                  80

Asn Ile His Leu Asn Ile Ala His Ser Val Gln Leu Ile Arg Pro Ile
                 85                  90                  95

Leu Ala Tyr Arg Phe Lys His Leu Asp Arg Val Ser Ile Gln Gln Leu
            100                 105                 110

Asn Leu Tyr Asp Asp Gly Ser Asp Glu Tyr Val Asp Leu Glu Lys Glu
        115                 120                 125

Glu Asn Lys Asp Ile Ser Ala Glu Ile Lys Gln Ala Glu Lys Gln Leu
    130                 135                 140

Ser His Tyr Leu Leu Thr Gly Lys Ile Lys Phe Asp Asn Pro Thr Ile
145                 150                 155                 160

Ala Arg Tyr Val Trp Gln Ser Ala Phe Pro Val Lys Tyr His Phe Leu
                165                 170                 175

Ser Thr Asp Tyr Phe Glu Lys Ala Glu Phe Leu Gln Pro Leu Lys Glu
            180                 185                 190
```

-continued

```
Tyr Leu Ala Glu Asn Tyr Gln Lys Met Asp Trp Thr Ala Tyr Gln Gln
        195                 200                 205

Leu Thr Pro Glu Gln Gln Ala Phe Tyr Leu Thr Leu Val Gly Phe Asn
    210                 215                 220

Asp Glu Val Lys Gln Ser Leu Glu Val Gln Gln Ala Lys Phe Ile Phe
225                 230                 235                 240

Thr Gly Thr Thr Thr Trp Glu Gly Asn Thr Asp Val Arg Glu Tyr Tyr
                245                 250                 255

Ala Gln Gln Gln Leu Asn Leu Leu Asn His Phe Thr Gln Ala Glu Gly
            260                 265                 270

Asp Leu Phe Ile Gly Asp His Tyr Lys Ile Tyr Phe Lys Gly His Pro
        275                 280                 285

Arg Gly Gly Glu Ile Asn Asp Tyr Ile Leu Asn Asn Ala Lys Asn Ile
    290                 295                 300

Thr Asn Ile Pro Ala Asn Ile Ser Phe Glu Val Leu Met Met Thr Gly
305                 310                 315                 320

Leu Leu Pro Asp Lys Val Gly Gly Val Ala Ser Ser Leu Tyr Phe Ser
                325                 330                 335

Leu Pro Lys Glu Lys Ile Ser His Ile Ile Phe Thr Ser Asn Lys Gln
            340                 345                 350

Val Lys Ser Lys Glu Asp Ala Leu Asn Asn Pro Tyr Val Lys Val Met
        355                 360                 365

Arg Arg Leu Gly Ile Ile Asp Glu Ser Gln Val Ile Phe Trp Asp Ser
    370                 375                 380

Leu Lys Gln Leu Gly Gly Gly Leu Glu
385                 390
```

```
<210> SEQ ID NO 4
<211> LENGTH: 1182
<212> TYPE: DNA
<213> ORGANISM: Artificial Sequence
<220> FEATURE:
<223> OTHER INFORMATION: synthetic delta21PmST1 glycosyltransferase
      family 80 (GT80) M120D mutant having decreased alpha2-3
      sialidase activity

<400> SEQUENCE: 4
atgaaaacaa tcacgctgta tttagatcct gcctccttac cggcattaaa tcagctgatg      60
gactttacgc aaaataatga agataaaaca catccacgta tttttggtct ttctcgcttt     120
aaaatccctg acaacattat tacacagtat caaaatatcc atttcgtcga actcaaagat     180
aatcgtccca ctgaagcact tttacgattt ttagatcaat accctggtaa cattgagtta     240
aatatacact taaatattgc tcattccgtt caattaattc gtccgatttt ggcatatcgt     300
tttaaacatt tagatcgtgt atcaattcag cagttaaatc tttatgacga tggctcagat     360
gaatatgttg atttagaaaa agaagaaaat aaagatattt ccgcagaaat taagcaagca     420
gaaaaacaac tttctcacta tttgcttact ggcaaaataa aatttgataa cccaactatt     480
gctcgttatg tctggcaatc cgcgttccca gtaaaatatc attttttaag tacagactat     540
tttgaaaaag ccgaattttt acaaccacta aaagaatatt tagcagaaaa ttatcaaaaa     600
atggactgga ctgcttacca acagctgact ccagaacagc aagcattcta cttaacattg     660
gtaggcttca atgacgaagt caagcagtcg ctagaagtgc aacaagctaa atttatcttt     720
accggcacga caacttggga aggaaatacc gatgtgcgag aatactacgc acagcaacaa     780
cttaatttac ttaatcactt tacccaagct gagggcgatt tatttattgg tgatcattat     840
```

-continued

```
aaaatctact ttaaagggca tcctagaggt ggtgaaatta atgactacat tctgaacaat    900
gctaaaaata tcaccaatat ccctgccaat atttcctttg aagtattgat gatgacaggc    960
ttattacctg ataaagtggg tggtgttgca agttcactgt atttctcctt accaaaagaa   1020
aaaattagcc atattatttt cacatcgaat aaacaagtga aaagcaaaga agatgcgcta   1080
aataatccgt atgttaaggt catgcgtcgt ttaggtataa ttgacgaatc acaagtcatc   1140
tttttgggaca gtttaaaaca gttgggtgga ggtctcgagt ga                     1182
```

<210> SEQ ID NO 5
<211> LENGTH: 393
<212> TYPE: PRT
<213> ORGANISM: Artificial Sequence
<220> FEATURE:
<223> OTHER INFORMATION: synthetic delta21PmST1 glycosyltransferase
family 80 (GT80) M120H mutant having decreased alpha2-3
sialidase activity

<400> SEQUENCE: 5

```
Met Lys Thr Ile Thr Leu Tyr Leu Asp Pro Ala Ser Leu Pro Ala Leu
 1               5                   10                  15

Asn Gln Leu Met Asp Phe Thr Gln Asn Gl

Thr Asn Ile Pro Ala Asn Ile Ser Phe Glu Val Leu Met Met Thr Gly
305                 310                 315                 320

Leu Leu Pro Asp Lys Val Gly Val Ala Ser Ser Leu Tyr Phe Ser
            325                 330                 335

Leu Pro Lys Glu Lys Ile Ser His Ile Ile Phe Thr Ser Asn Lys Gln
                340                 345                 350

Val Lys Ser Lys Glu Asp Ala Leu Asn Asn Pro Tyr Val Lys Val Met
            355                 360                 365

Arg Arg Leu Gly Ile Ile Asp Glu Ser Gln Val Ile Phe Trp Asp Ser
        370                 375                 380

Leu Lys Gln Leu Gly Gly Gly Leu Glu
385                 390

<210> SEQ ID NO 6
<211> LENGTH: 1182
<212> TYPE: DNA
<213> ORGANISM: Artificial Sequence
<220> FEATURE:
<223> OTHER INFORMATION: synthetic delta21PmST1 glycosyltransferase
      family 80 (GT80) M120H mutant having decreased alpha2-3
      sialidase activity

<400> SEQUENCE: 6

```
atgaaaacaa tcacgctgta tttagatcct gcctccttac cggcattaaa tcagctgatg      60
gactttacgc aaaataatga agataaaaca catccacgta ttttttggtct ttctcgcttt    120
aaaatccctg acaacattat tacacagtat caaaatatcc atttcgtcga actcaaagat    180
aatcgtccca ctgaagcact ttttacgatt ttagatcaat accctggtaa cattgagtta    240
aatatacact aaatattgc tcattccgtt caattaattc gtccgatttt ggcatatcgt    300
tttaaacatt tagatcgtgt atcaattcag cagttaaatc tttatgacga tggctcacat    360
gaatatgttg atttagaaaa agaagaaaat aaagatattt ccgcagaaat taagcaagca    420
gaaaaacaac tttctcacta tttgcttact ggcaaaataa aatttgataa cccaactatt    480
gctcgttatg tctggcaatc cgcgttccca gtaaaatatc attttttaag tacagactat    540
tttgaaaaag ccgaatttt acaaccacta aaagaatatt tagcagaaaa ttatcaaaaa    600
atggactgga ctgcttacca acagctgact ccagaacagc aagcattcta cttaacattg    660
gtaggcttca atgacgaagt caagcagtcg ctagaagtgc aacaagctaa atttatcttt    720
accggcacga caacttggga aggaaatacc gatgtgcgag aatactacgc acagcaacaa    780
cttaattta ttaatcactt tacccaagct gagggcgatt tatttattgg tgatcattat    840
aaaatctact ttaagggca tcctagaggt ggtgaaatta tgactacat tctgaacaat    900
gctaaaaata tcaccaatat ccctgccaat atttcctttg aagtattgat gatgacaggc    960
ttattacctg ataaagtggg tggtgttgca agttcactgt atttctcctt accaaaagaa   1020
aaaattagcc atattatttt cacatcgaat aaacaagtga aaagcaaaga agatgcgcta   1080
aataatccgt atgttaaggt catgcgtcgt ttaggtataa ttgacgaatc acaagtcatc   1140
ttttgggaca gtttaaaaca gttgggtgga ggtctcgagt ga                      1182
```

<210> SEQ ID NO 7
<211> LENGTH: 393
<212> TYPE: PRT
<213> ORGANISM: Artificial Sequence
<220> FEATURE:
<223> OTHER INFORMATION: synthetic delta21PmST1 glycosyltransferase family 80 (GT80) E247F mutant having decreased alpha2-3
sialidase activity

<400> SEQUENCE: 7

Met Lys Thr Ile Thr Leu Tyr Leu Asp Pro Ala Ser Leu Pro Ala Leu
1               5                   10                  15

Asn Gln Leu Met Asp Phe Thr Gln Asn Asn Glu Asp Lys Thr His Pro
            20                  25                  30

Arg Ile Phe Gly Leu Ser Arg Phe Lys Ile Pro Asp Asn Ile Ile Thr
        35                  40                  45

Gln Tyr Gln Asn Ile His Phe Val Glu Leu Lys Asp Asn Arg Pro Thr
    50                  55                  60

Glu Ala Leu Phe Thr Ile Leu Asp Gln Tyr Pro Gly Asn Ile Glu Leu
65                  70                  75                  80

Asn Ile His Leu Asn Ile Ala His Ser Val Gln Leu Ile Arg Pro Ile
                85                  90                  95

Leu Ala Tyr Arg Phe Lys His Leu Asp Arg Val Ser Ile Gln Gln Leu
            100                 105                 110

Asn Leu Tyr Asp Asp Gly Ser Met Glu Tyr Val Asp Leu Glu Lys Glu
        115                 120                 125

Glu Asn Lys Asp Ile Ser Ala Glu Ile Lys Gln Ala Glu Lys Gln Leu
    130                 135                 140

Ser His Tyr Leu Leu Thr Gly Lys Ile Lys Phe As

<210> SEQ ID NO 8
<211> LENGTH: 1182
<212> TYPE: DNA
<213> ORGANISM: Artificial Sequence
<220> FEATURE:
<223> OTHER INFORMATION: synthetic delta21PmST1 glycosyltransferase family 80 (GT80) E247F mutant having decreased alpha2-3 sialidase activity

<400> SEQUENCE: 8

```
atgaaaacaa tcacgctgta tttagatcct gcctccttac cggcattaaa tcagctgatg      60
gactttacgc aaaataatga agataaaaca catccacgta tttttggtct ttctcgcttt     120
aaaatccctg acaacattat tacacagtat caaaatatcc atttcgtcga actcaaagat     180
aatcgtccca ctgaagcact tttacgattt ttagatcaat accctggtaa cattgagtta     240
aatatacact taaatattgc tcattccgtt caattaattc gtccgatttt ggcatatcgt     300
tttaaacatt tagatcgtgt atcaattcag cagttaaatc tttatgacga tggctcaatg     360
gaatatgttg atttagaaaa agaagaaaat aaagatattt ccgcagaaat taagcaagca     420
gaaaaacaac tttctcacta tttgcttact ggcaaaataa aatttgataa cccaactatt     480
gctcgttatg tctggcaatc cgcgttccca gtaaaatatc atttttttaag tacagactat     540 tttgaaaaag ccgaattttt acaaccacta aaagaatatt tagcagaaaa ttatcaaaaa     600
atggactgga ctgcttacca acagctgact ccagaacagc aagcattcta cttaacattg     660
gtaggcttca atgacgaagt caagcagtcg ctagaagtgc aacaagctaa atttatcttt     720
accggcacga caacttggtt tggaaatacc gatgtgcgag aatactacgc acagcaacaa     780
cttaatttac ttaatcactt tacccaagct gagggcgatt tatttattgg tgatcattat     840
aaaatctact ttaaagggca tcctagaggt ggtgaaatta atgactacat tctgaacaat     900
gctaaaaata tcaccaatat ccctgccaat atttcctttg aagtattgat gatgacaggc     960
ttattacctg ataaagtggg tggtgttgca agttcactgt atttctcctt accaaaagaa    1020
aaaattagcc atattatttt cacatcgaat aaacaagtga aaagcaaaga agatgcgcta    1080
aataatccgt atgttaaggt catgcgtcgt ttaggtataa ttgacgaatc acaagtcatc    1140
ttttgggaca gtttaaaaca gttgggtgga ggtctcgagt ga                       1182
```

<210> SEQ ID NO 9
<211> LENGTH: 393
<212> TYPE: PRT
<213> ORGANISM: Artificial Sequence
<220> FEATURE:
<223> OTHER INFORMATION: synthetic delta21PmST1 glycosyltransferase family 80 (GT80) R289Y mutant having decreased alpha2-3 sialidase activity

<400> SEQUENCE: 9

```
Met Lys Thr Ile Thr Leu Tyr Leu Asp Pro Ala Ser Leu Pro Ala Leu
 1               5                  10                  15

Asn Gln Leu Met Asp Phe Thr Gln Asn Asn Glu Asp Lys Thr His Pro
            20                  25                  30

Arg Ile Phe Gly Leu Ser Arg Phe Lys Ile Pro Asp Asn Ile Ile Thr
        35                  40                  45

Gln Tyr Gln Asn Ile His Phe Val Glu Leu Lys Asp Asn Arg Pro Thr
    50                  55                  60

Glu Ala Leu Phe Thr Ile Leu Asp Gln Tyr Pro Gly Asn Ile Glu Leu
65                  70                  75                  80
```

Asn Ile His Leu Asn Ile Ala His Ser Val Gln Leu Ile Arg Pro Ile
              85                  90                  95

Leu Ala Tyr Arg Phe Lys His Leu Asp Arg Val Ser Ile Gln Gln Leu
            100                 105                 110

Asn Leu Tyr Asp Asp Gly Ser Met Glu Tyr Val Asp Leu Glu Lys Glu
        115                 120                 125

Glu Asn Lys Asp Ile Ser Ala Glu Ile Lys Gln Ala Glu Lys Gln Leu
    130                 135                 140

Ser His Tyr Leu Leu Thr Gly Lys Ile Lys Phe Asp Asn Pro Thr Ile
145                 150                 155                 160

Ala Arg Tyr Val Trp Gln Ser Ala Phe Pro Val Lys Tyr His Phe Leu
                165                 170                 175

Ser Thr Asp Tyr Phe Glu Lys Ala Glu Phe Leu Gln Pro Leu Lys Glu
            180                 185                 190

Tyr Leu Ala Glu Asn Tyr Gln Lys Met Asp Trp Thr Ala Tyr Gln Gln
        195                 200                 205

Leu Thr Pro Glu Gln Gln Ala Phe Tyr Leu Thr Leu Val Gly Phe Asn
    210                 215                 220

Asp Glu Val Lys Gln Ser Leu Glu Val Gln Gln Ala Lys Phe Ile Phe
225                 230                 235                 240

Thr Gly Thr Thr Thr Trp Glu Gly Asn Thr Asp Val Arg Glu Tyr Tyr
                245                 250                 255

Ala Gln Gln Gln Leu Asn Leu Leu Asn His Phe Thr Gln Ala Glu Gly
            260                 265                 270

Asp Leu Phe Ile Gly Asp His Tyr Lys Ile Tyr Phe Lys Gly His Pro
        275                 280                 285

Tyr Gly Gly Glu Ile Asn Asp Tyr Ile Leu Asn Asn Ala Lys Asn Ile
    290                 295                 300

Thr Asn Ile Pro Ala Asn Ile Ser Phe Glu Val Leu Met Met Thr Gly
305                 310                 315                 320

Leu Leu Pro Asp Lys Val Gly Val Ala Ser Ser Leu Tyr Phe Ser
                325                 330                 335

Leu Pro Lys Glu Lys Ile Ser His Ile Ile Phe Thr Ser Asn Lys Gln
            340                 345                 350

Val Lys Ser Lys Glu Asp Ala Leu Asn Asn Pro Tyr Val Lys Val Met
        355                 360                 365

Arg Arg Leu Gly Ile Ile Asp Glu Ser Gln Val Ile Phe Trp Asp Ser
    370                 375                 380

Leu Lys Gln Leu Gly Gly Gly Leu Glu
385                 390

<210> SEQ ID NO 10
<211> LENGTH: 1182
<212> TYPE: DNA
<213> ORGANISM: Artificial Sequence
<220> FEATURE:
<223> OTHER INFORMATION: synthetic delta21PmST1 glycosyltransferase
      family 80 (GT80) R289Y mutant having decreased alpha2-3 sialidase
      activity

<400> SEQUENCE: 10
atgaaaacaa tcacgctgta tttagatcct gcctccttac cggcattaaa tc

```
aatcgtccca ctgaagcact ttttacgatt ttagatcaat accctggtaa cattgagtta    240
aatatacact taaatattgc tcattccgtt caattaattc gtccgatttt ggcatatcgt    300
tttaaacatt tagatcgtgt atcaattcag cagttaaatc tttatgacga tggctcaatg    360
gaatatgttg atttagaaaa agaagaaaat aaagatattt ccgcagaaat taagcaagca    420
gaaaaacaac tttctcacta tttgcttact ggcaaaataa aatttgataa cccaactatt    480
gctcgttatg tctggcaatc cgcgttccca gtaaaatatc attttttaag tacagactat    540
tttgaaaaag ccgaattttt acaaccacta aaagaatatt tagcagaaaa ttatcaaaaa    600
atggactgga ctgcttacca acagctgact ccagaacagc aagcattcta cttaacattg    660
gtaggcttca atgacgaagt caagcagtcg ctagaagtgc aacaagctaa atttatcttt    720
accggcacga caacttggga aggaaatacc gatgtgcgag aatactacgc acagcaacaa    780
cttaatttac ttaatcactt tacccaagct gagggcgatt tatttattgg tgatcattat    840
aaaatctact ttaagggca tccttatggt ggtgaaatta atgactacat tctgaacaat    900
gctaaaaata tcaccaatat ccctgccaat atttcctttg aagtattgat gatgacaggc    960
ttattacctg ataaagtggg tggtgttgca agttcactgt atttctcctt accaaaagaa   1020
aaaattagcc atattatttt cacatcgaat aaacaagtga aaagcaaaga agatgcgcta   1080
aataatccgt atgttaaggt catgcgtcgt ttaggtataa ttgacgaatc acaagtcatc   1140
ttttgggaca gtttaaaaca gttgggtgga ggtctcgagt ga                      1182
```

<210> SEQ ID NO 11
<211> LENGTH: 393
<212> TYPE: PRT
<213> ORGANISM: Artificial Sequence
<220> FEATURE:
<223> OTHER INFORMATION: synthetic delta21PmST1 glycosyltransferase
      family 80 (GT80) E247F/R289Y double mutant having decreased
      alpha2-3 sialidase activity

<400> SEQUENCE: 11

```
Met Lys Thr Ile Thr Leu Tyr Leu Asp Pro Ala Ser Leu Pro Ala Leu
1               5                   10                  15

Asn Gln Leu Met

Ser Thr Asp Tyr Phe Glu Lys Ala Glu Phe Leu Gln Pro Leu Lys Glu
            180                 185                 190

Tyr Leu Ala Glu Asn Tyr Gln Lys Met Asp Trp Thr Ala Tyr Gln Gln
        195                 200                 205

Leu Thr Pro Glu Gln Gln Ala Phe Tyr Leu Thr Leu Val Gly Phe Asn
    210                 215                 220

Asp Glu Val Lys Gln Ser Leu Glu Val Gln Gln Ala Lys Phe Ile Phe
225                 230                 235                 240

Thr Gly Thr Thr Thr Trp Phe Gly Asn Thr Asp Val Arg Glu Tyr Tyr
                245                 250                 255

Ala Gln Gln Gln Leu Asn Leu Leu Asn His Phe Thr Gln Ala Glu Gly
        260                 265                 270

Asp Leu Phe Ile Gly Asp His Tyr Lys Ile Tyr Phe Lys Gly His Pro
    275                 280                 285

Tyr Gly Gly Glu Ile Asn Asp Tyr Ile Leu Asn Asn Ala Lys Asn Ile
        290                 295                 300

Thr Asn Ile Pro Ala Asn Ile Ser Phe Glu Val Leu Met Met Thr Gly
305                 310                 315                 320

Leu Leu Pro Asp Lys Val Gly Val Ala Ser Ser Leu Tyr Phe Ser
                325                 330                 335

Leu Pro Lys Glu Lys Ile Ser His Ile Ile Phe Thr Ser Asn Lys Gln
        340                 345                 350

Val Lys Ser Lys Glu Asp Ala Leu Asn Asn Pro Tyr Val Lys Val Met
    355                 360                 365

Arg Arg Leu Gly Ile Ile Asp Glu Ser Gln Val Ile Phe Trp Asp Ser
370                 375                 380

Leu Lys Gln Leu Gly Gly Gly Leu Glu
385                 390

<210> SEQ ID NO 12
<211> LENGTH: 1182
<212> TYPE: DNA
<213> ORGANISM: Artificial Sequence
<220> FEATURE:
<223> OTHER INFORMATION: synthetic delta21PmST1 glycosyltransferase
      family 80 (GT80) E247F/R289Y double mutant having decreased
      alpha2-3 sialidase activity

<400> SEQUENCE: 12
atgaaaacaa tcacgctgta tttagatcct gcctccttac cggcattaaa tcagctgatg     60
gactttacgc aaaataatga agataaaaca catccacgta tttttggtct ttctcgcttt    120
aaaatccctg acaacattat tacacagtat caaaatatcc atttcgtcga actcaaagat    180
aatcgtccca ctgaagcact ttttacgatt ttagatcaat accctggtaa cattgagtta    240
aatatacact taaatattgc tcattccgtt caattaattc gtccgatttt ggcatatcgt    300
tttaaacatt tagatcgtgt atcaattcag cagttaaatc tttatgacga tggctcaatg    360
gaatatgttg atttagaaaa agaagaaaat aaagatattt ccgcagaaat taagcaagca    420
gaaaaacaac tttctcacta tttgcttact ggcaaaataa aatttgataa cccaactatt    480
gctcgttatg tctggcaatc cgcgttccca gtaaaatatc attttttaag tacagactat    540
tttgaaaaag ccgaattttt acaaccacta aaagaatatt tagcagaaaa ttatcaaaaa    600
atggactgga ctgcttacca acagctgact ccagaacagc aagcattcta cttaacattg    660
gtaggcttca atgacgaagt caagcagtcg ctagaagtgc aacaagctaa atttatcttt    720
accggcacga caacttggtt tggaaatacc gatgtgcgag aatactacgc acagcaacaa    780

```
cttaatttac ttaatcactt tacccaagct gagggcgatt tatttattgg tgatcattat    840
aaaatctact ttaaagggca tccttatggt ggtgaaatta atgactacat tctgaacaat    900
gctaaaaata tcaccaatat ccctgccaat atttcctttg aagtattgat gatgacaggc    960
ttattacctg ataaagtggg tggtgttgca agttcactgt atttctcctt accaaaagaa   1020
aaaattagcc atattatttt cacatcgaat aaacaagtga aagcaaaga agatgcgcta    1080 aataatccgt atgttaaggt catgcgtcgt ttaggtataa ttgacgaatc acaagtcatc   1140
ttttgggaca gtttaaaaca gttgggtgga ggtctcgagt ga                      1182

<210> SEQ ID NO 13
<211> LENGTH: 412
<212> TYPE: PRT
<213> ORGANISM: Pasteurella multocida
<220> FEATURE:
<223> OTHER INFORMATION: PmST1 wild-type glycosyltransferase family 80
      (GT80), GT80 sialyltransferase, Pm0188Ph

<400> SEQUENCE: 13

Met Lys Asn Arg Arg Leu Asn Phe Lys Leu Phe Phe Leu Ile Ile Phe
 1               5                  10                  15

Ser Leu Phe Ser Thr Leu Ser Trp Ser Lys Thr Ile Thr Leu Tyr Leu
            20                  25                  30

Asp Pro Ala Ser Leu Pro Ala Leu Asn Gln Leu Met Asp Phe Thr Gln
        35                  40                  45

Asn Asn Glu Asp Lys Thr His Pro Arg Ile Phe Gly Leu Ser Arg Phe
    50                  55                  60

Lys Ile Pro Asp Asn Ile Ile Thr Gln Tyr Gln Asn Ile His Phe Val
65                  70                  75                  80

Glu Leu Lys Asp Asn Arg Pro Thr Glu Ala Leu Phe Thr Ile Leu Asp
                85                  90                  95

Gln Tyr Pro Gly Asn Ile Glu Leu Asn Ile His Leu Asn Ile Ala His
            100                 105                 110

Ser Val Gln Leu Ile Arg Pro Ile Leu Ala Tyr Arg Phe Lys His Leu
        115                 120                 125

Asp Arg Val Ser Ile Gln Gln Leu Asn Leu Tyr Asp Asp Gly Ser Met
    130                 135                 140

Glu Tyr Val Asp Leu Glu Lys Glu Glu Asn Lys Asp Ile Ser Ala Glu
145                 150                 155                 160

Ile Lys Gln Ala Glu Lys Gln Leu Ser His Tyr Leu Leu Thr Gly Lys
                165                 170                 175

Ile Lys Phe Asp Asn Pro Thr Ile Ala Arg Tyr Val Trp Gln Ser Ala
            180                 185                 190

Phe Pro Val Lys Tyr His Phe Leu Ser Thr Asp Tyr Phe Glu Lys Ala
        195                 200                 205

Glu Phe Leu Gln Pro Leu Lys Glu Tyr Leu Ala Glu Asn Tyr Gln Lys
    210                 215                 220

Met Asp Trp Thr Ala Tyr Gln Gln Leu Thr Pro Glu Gln Gln Ala Phe
225                 230                 235                 240

Tyr Leu Thr Leu Val Gly Phe Asn Asp Glu Val Lys Gln Ser Leu Glu
                245                 250                 255

Val Gln Gln Ala Lys Phe Ile Phe Thr Gly Thr Thr Thr Trp Glu Gly
            260                 265                 270

Asn Thr Asp Val Arg Glu Tyr Tyr Ala Gln Gln Gln Leu Asn Leu Leu
        275                 280                 285
```

```
Asn His Phe Thr Gln Ala Glu Gly Asp Leu Phe Ile Gly Asp His Tyr
    290                 295                 300
Lys Ile Tyr Phe Lys Gly His Pro Arg Gly Gly Glu Ile Asn Asp Tyr
305                 310                 315                 320
Ile Leu Asn Asn Ala Lys Asn Ile Thr Asn Ile Pro Ala Asn Ile Ser
                325                 330                 335
Phe Glu Val Leu Met Met Thr Gly Leu Leu Pro Asp Lys Val Gly Gly
                340                 345                 350
Val Ala Ser Ser Leu Tyr Phe Ser Leu Pro Lys Glu Lys Ile Ser His
            355                 360                 365
Ile Ile Phe Thr Ser Asn Lys Gln Val Lys Ser Lys Glu Asp Ala Leu
    370                 375                 380
Asn Asn Pro Tyr Val Lys Val Met Arg Arg Leu Gly Ile Ile Asp Glu
385                 390                 395                 400
Ser Gln Val Ile Phe Trp Asp Ser Leu Lys Gln Leu
                405                 410
```

<210> SEQ ID NO 14
<211> LENGTH: 1239
<212> TYPE: DNA
<213> ORGANISM: Pasteurella multocida
<220> FEATURE:
<223> OTHER INFORMATION: PmST1 wild-type glycosyltransferase family 80
      (GT80), GT80 sialyltransferase, Pm0188Ph

<400> SEQUENCE: 14

```
atgaaaaatc gtcgactcaa tttcaaactg ttttcctca tcatttttc attattcagc      60
acactgagtt ggtcaaaaac aatcacgctg tatttagatc ctgcctcctt accggcatta     120
aatcagctga tggactttac gcaaaataat gaagataaaa cacatccacg tatttttggt     180
ctttctcgct ttaaaatccc tgacaacatt attacacagt atcaaaatat ccatttcgtc     240
gaactcaaag ataatcgtcc cactgaagca ctttttacga ttttagatca atacccctggt    300
aacattgagt taaatataca cttaaatatt gctcattccg ttcaattaat tcgtccgatt     360
ttggcatatc gttttaaaca tttagatcgt gtatcaattc agcagttaaa tctttatgac     420
gatggctcaa tggaatatgt tgatttagaa aaagaagaaa ataaagatat tccgcagaa      480
attaagcaag cagaaaaaca actttctcac tatttgctta ctggcaaaat aaaatttgat     540
aacccaacta ttgctcgtta tgtctggcaa tccgcgttcc agtaaaata tcatttttta     600
agtacagact attttgaaaa agccgaattt tacaaccac taaagaata tttagcagaa      660
aattatcaaa aaatggactg gactgcttac caacagctga ctccagaaca gcaagcattc     720
tacttaacat tggtaggctt caatgacgaa gtcaagcagt cgctagaagt gcaacaagct     780
aaatttatct ttaccggcac gacaacttgg gaaggaaata ccgatgtgcg agaatactac     840
gcacagcaac aacttaattt acttaatcac tttaccccaag ctgagggcga tttatttatt     900
ggtgatcatt ataaaatcta ctttaaaggg catcctagag tggtgaaat taatgactac      960
attctgaaca atgctaaaaa tatcaccaat atccctgcca atatttcctt tgaagtattg    1020
atgatgacag gcttattacc tgataaagtg ggtggtgttg caagttcact gtatttctcc    1080
ttaccaaaag aaaaaattag ccatattatt ttcacatcga ataaacaagt gaaaagcaaa    1140
gaagatgcgc taaataatcc gtatgttaag gtcatgcgtc gtttaggtat aattgacgaa    1200
tcacaagtca tcttttggga cagtttaaaa cagttgtaa                           1239
```

<210> SEQ ID NO 15
<211> LENGTH: 514
<212> TYPE: PRT
<213> ORGANISM: Unknown
<220> FEATURE:
<223> OTHER INFORMATION: Psp2,6ST glycosyltransferase family 80 (GT80), GT80 sialyltransferase, Psp-pst6-1

<400> SEQUENCE: 15

```
Met Lys Asn Phe Leu Leu Leu Thr Leu Ile Leu Leu Thr Ala Cys Asn
1               5                   10                  15

Asn Ser Glu Glu Asn Thr Gln Ser Ile Ile Lys Asn Asp Ile Asn Lys
            20                  25                  30

Thr Ile Ile Asp Glu Glu Tyr Val Asn Leu Pro Ile Asn Gln Ser
        35                  40                  45

Asn Ile Ser Phe Thr Lys His Ser Trp Val Gln Thr Cys Gly Thr Gln
    50                  55                  60

Gln Leu Leu Thr Glu Gln Asn Lys Glu Ser Ile Ser Leu Ser Val Val
65                  70                  75                  80

Ala Pro Arg Leu Asp Asp Glu Lys Tyr Cys Phe Asp Phe Asn Gly
            85                  90                  95

Val Ser Asn Lys Gly Lys Tyr Ile Thr Lys Val Thr Leu Asn Val
            100                 105                 110

Val Ala Pro Ser Leu Glu Val Tyr Val Asp His Ala Ser Leu Pro Thr
        115                 120                 125

Leu Gln Gln Leu Met Asp Ile Ile Lys Ser Glu Glu Glu Asn Pro Thr
130                 135                 140

Ala Gln Arg Tyr Ile Ala Trp Gly Arg Ile Val Pro Thr Asp Glu Gln
145                 150                 155                 160

Met Lys Glu Leu Asn Ile Thr Ser Phe Ala Leu Ile Asn Asn His Thr
                165                 170                 175

Pro Ala Asp Leu Val Gln Glu Ile Val Lys Gln Ala Gln Thr Lys His
            180                 185                 190

Arg Leu Asn Val Lys Leu Ser Ser Asn Thr Ala His Ser Phe Asp Asn
        195                 200                 205

Leu Val Pro Ile Leu Lys Glu Leu Asn Ser Phe Asn Asn Val Thr Val
    210                 215                 220

Thr Asn Ile Asp Leu Tyr Asp Asp Gly Ser Ala Glu Tyr Val Asn Leu
225                 230                 235                 240

Tyr Asn Trp Arg Asp Thr Leu Asn Lys Thr Asp Asn Leu Lys Ile Gly
                245                 250                 255

Lys Asp Tyr Leu Glu Asp Val Ile Asn Gly Ile Asn Glu Asp Thr Ser
            260                 265                 270

Asn Thr Gly Thr Ser Ser Val Tyr Asn Trp Gln Lys Leu Tyr Pro Ala
        275                 280                 285

Asn Tyr His Phe Leu Arg Lys Asp Tyr Leu Thr Leu Glu Pro Ser Leu
    290                 295                 300

His Glu Leu Arg Asp Tyr Ile Gly Asp Ser Leu Lys Gln Met Gln Trp
305                 310                 315                 320

Asp Gly Phe Lys Lys Phe Asn Ser Lys Gln Gln Glu Leu Phe Leu Ser
                325                 330                 335

Ile Val Asn Phe Asp Lys Gln Lys Leu Gln Asn Glu Tyr Asn Ser Ser
            340                 345                 350

Asn Leu Pro Asn Phe Val Phe Thr Gly Thr Thr Val Trp Ala Gly Asn
        355                 360                 365
```

```
His Glu Arg Glu Tyr Tyr Ala Lys Gln Gln Ile Asn Val Ile Asn Asn
    370                 375                 380

Ala Ile Asn Glu Ser Ser Pro His Tyr Leu Gly Asn Ser Tyr Asp Leu
385                 390                 395                 400

Phe Phe Lys Gly His Pro Gly Gly Gly Ile Ile Asn Thr Leu Ile Met
                405                 410                 415

Gln Asn Tyr Pro Ser Met Val Asp Ile Pro Ser Lys Ile Ser Phe Glu
                420                 425                 430

Val Leu Met Met Thr Asp Met Leu Pro Asp Ala Val Ala Gly Ile Ala
                435                 440                 445

Ser Ser Leu Tyr Phe Thr Ile Pro Ala Glu Lys Ile Lys Phe Ile Val
    450                 455                 460

Phe Thr Ser Thr Glu Thr Ile Thr Asp Arg Glu Thr Ala Leu Arg Ser
465                 470                 475                 480

Pro Leu Val Gln Val Met Ile Lys Leu Gly Ile Val Lys Glu Glu Asn
                485                 490                 495

Val Leu Phe Trp Ala Asp Leu Pro Asn Cys Glu Thr Gly Val Cys Ile
                500                 505                 510

Ala Val
```

<210> SEQ ID NO 16
<211> LENGTH: 1545
<212> TYPE: DNA
<213> ORGANISM: Unknown
<220> FEATURE:
<223> OTHER INFORMATION: Psp2,6ST glycosyltransferase family 80 (GT80),
      GT80 sialyltransferase, Psp-pst6-1

<400> SEQUENCE: 16

```
atgaaaaact tttattatt aactttaata ttacttactg cttgtaataa ttcagaagaa    60
aatacacaat ctattattaa aaatgatatt aataaaacta ttattgatga ggagtatgtt   120
aatttagagc caattaatca atcaaacatc tcttttacaa acactcttg ggtacaaact    180
tgtggtacgc aacaactatt aacagaacaa ataaagagt caatatcatt atctgtagtg   240
gcgccacgat tagatgacga tgaaaagtac tgctttgatt ttaatggtgt tagtaataaa   300
ggtgaaaaat atataacaaa agtaacatta aacgtagtgg ctccatcttt agaggtttat   360
gttgatcatg catctcttcc aactcttcag cagctaatgg atattattaa atcggaagaa   420
gaaaatccta cagcacaaag atatatagct tgggggagaa tagttccgac tgatgagcaa   480
atgaaagagt taaatattac atcgtttgca ttgataaata accatacacc agctgactta   540
gtacaagaaa ttgttaagca agcacaaaca aagcatagat tgaatgttaa acttagctct   600
aacactgctc attcatttga taatttagtg ccaatactaa aagaattaaa ttcgtttaat   660
aacgttacgg taacaaatat agattatat gatgatggtt cagcagaata tgtaaattta   720
tataactgga gagatacatt aaataaaaca gataatttaa aaattggtaa agattatctt   780
gaggatgtca ttaatggtat caatgaagac acttcaaata caggaacatc atctgtttat   840
aactggcaaa actatatccc agctaactac catttttaa gaaaagatta tttaacttta   900
gaaccatcat tacatgagtt acgagactat attggtgata gtttaaagca aatgcaatgg   960
gatggtttca aaaaattcaa tagcaaacaa caagaattat tcttatcgat tgttaatttt  1020
gacaaacaaa aattacaaaa tgaatataat tcatctaatt taccaaactt tgtgtttaca  1080
ggtacgactg tatgggctgg taaccatgaa agagagtatt atgcgaaaca acaaattaat  1140
gtcattaata atgcaattaa tgaatcgagc ccacatatt taggcaatag ttatgatttg  1200
```

```
ttcttcaaag gtcaccctgg tggcggtatc attaatacat taataatgca aaactatcct   1260
tcaatggttg atattccatc aaaaatatca tttgaagttt tgatgatgac agatatgctt   1320
cctgatgcag ttgctggtat agcgagctct ttatatttca cgataccagc tgaaaaaatt   1380
aaatttatag ttttttacatc gacagaaact ataactgatc gtgaaactgc tttgagaagt   1440
cctttagttc aagtaatgat aaaactaggt attgtaaaag aagagaatgt acttttttgg   1500
gctgatctgc caaattgtga aacaggtgtt tgtattgcag tctag                    1545
```

<210> SEQ ID NO 17
<211> LENGTH: 402
<212> TYPE: PRT
<213> ORGANISM: Unknown
<220> FEATURE:
<223> OTHER INFORMATION: Vsp2,3ST glycosyltransferase family 80 (GT80),
      GT80 sialyltransferase, Vsp_2_3ST

<400> SEQUENCE: 17

```
Met Lys Asn Ile Ile Thr Lys Arg Met Leu Ile Ile Leu Ser Ser Leu
 1               5                  10                  15

Phe Thr Ile Ile Gly Cys Asn Asn Asp Asn Ser Thr Thr Thr Asn Asn
            20                  25                  30

Asn Ala Ile Glu Ile Tyr Val Asp Arg Ala Thr Leu Pro Thr Ile Gln
        35                  40                  45

Gln Met Thr Lys Ile Val Ser Gln Lys Thr Ser Asn Lys Lys Leu Ile
    50                  55                  60

Ser Trp Ser Arg Tyr Pro Ile Thr Asp Lys Ser Leu Leu Lys Lys Ile
65                  70                  75                  80

Asn Ala Glu Phe Phe Lys Glu Gln Phe Glu Leu Thr Glu Ser Leu Lys
                85                  90                  95

Asn Ile Ile Leu Ser Glu Asn Ile Asp Asn Leu Ile Ile His Gly Asn
            100                 105                 110

Thr Leu Trp Ser Ile Asp Val Val Asp Ile Ile Lys Glu Val Asn Leu
        115                 120                 125

Leu Gly Lys Asn Ile Pro Ile Glu Leu His Phe Tyr Asp Asp Gly Ser
    130                 135                 140

Ala Glu Tyr Val Arg Ile Tyr Glu Phe Ser Lys Leu Pro Glu Ser Glu
145                 150                 155                 160

Gln Lys Tyr Lys Thr Ser Leu Ser Lys Asn Asn Ile Lys Phe Ser Ile
                165                 170                 175

Asp Gly Thr Asp Ser Phe Lys Asn Thr Ile Glu Asn Ile Tyr Gly Phe
            180                 185                 190

Ser Gln Leu Tyr Pro Thr Thr Tyr His Met Leu Arg Ala Asp Ile Phe
        195                 200                 205

Asp Thr Thr Leu Lys Ile Asn Pro Leu Arg Glu Leu Leu Ser Asn Asn
    210                 215                 220

Ile Lys Gln Met Lys Trp Asp Tyr Phe Lys Asp Phe Asn Tyr Lys Gln
225                 230                 235                 240

Lys Asp Ile Phe Tyr Ser Leu Thr Asn Phe Asn Pro Lys Glu Ile Gln
                245                 250                 255

Glu Asp Phe Asn Lys Asn Ser Asn Lys Asn Phe Ile Phe Ile Gly Ser
            260                 265                 270

Asn Ser Ala Thr Ala Thr Ala Glu Glu Gln Ile Asn Ile Ile Ser Glu
        275                 280                 285

Ala Lys Lys Glu Asn Ser Ser Ile Ile Thr Asn Ser Ile Ser Asp Tyr
```

```
                  290                 295                 300
Asp Leu Phe Phe Lys Gly His Pro Ser Ala Thr Phe Asn Glu Gln Ile
305                 310                 315                 320

Ile Asn Ala His Asp Met Ile Glu Ile Asn Asn Lys Ile Pro Phe Glu
                325                 330                 335

Ala Leu Ile Met Thr Gly Ile Leu Pro Asp Ala Val Gly Met Gly
                340                 345                 350

Ser Ser Val Phe Phe Ser Ile Pro Lys Glu Val Lys Asn Lys Phe Val
            355                 360                 365

Phe Tyr Lys Ser Gly Thr Asp Ile Glu Asn Asn Ser Leu Ile Gln Val
        370                 375                 380

Met Leu Lys Leu Asn Leu Ile Asn Arg Asp Asn Ile Lys Leu Ile Ser
385                 390                 395                 400

Asp Ile
```

<210> SEQ ID NO 18
<211> LENGTH: 1209
<212> TYPE: DNA
<213> ORGANISM: Unknown
<220> FEATURE:
<223> OTHER INFORMATION: Vsp2,3ST glycosyltransferase family 80 (GT80), GT80 sialyltransferase, Vsp_2_3ST

<400> SEQUENCE: 18

```
atgaaaaaca ttataacaaa agaatgcta attattcttt cttctctatt cactattatc      60
ggatgcaaca atgataacag cactaccaca ataacaatg cgatagaaat atatgttgat     120
agagccactc ttccaactat tcagcaaatg acaaaatag tcagtcaaaa acaagtaat     180
aaaaaactta tttcatggtc tagatacccca ataactgata atcgttatt aaaaaaaatt   240
aatgcagaat tttttaaaga acaatttgaa ttaactgaat cactaaaaaa catcatatta   300
agtgaaaata tcgacaacct tataatccat ggtaatacac tctggtctat agatgtagta   360
gatataataa agaagttaa tctcctcggg aaaaacatac caattgaatt acatttttat   420
gacgatggtt cagctgaata tgtgagaata tacgaatttt caaaactgcc tgagtcagaa   480
caaaataca aacgtcact atctaaaaac aacataaat tcagcataga tgggactgat    540
tcatttaaaa acacaataga aaacattat ggattctcac aattataccc aacaacatat   600
cacatgttaa gagcggatat attcgataca acattaaaaa taaacccatt gagagagttg   660
ctttcaaata atataaaaca atgaaatgg gattacttta agactttaa ttataaacaa    720
aaagatattt tttactctttt gactaacttc aacccaaaag aaatacagga agatttcaac    780
aaaaactcaa ataaaaactt cattttttata ggaagtaata gtgctacagc aacagcagaa   840
gagcaaataa atattattcc agaagcaaaa aagaaaata gtagcattat aacaaactct   900
atatcagact atgatttatt tttcaaaggc cacccaagcg ccacattcaa cgaacaaata   960
attaatgcac acgatatgat cgaaattaac aacaagatcc cattcgaagc gttaataatg   1020
acaggaatac tacctgatgc tgtaggtggg atgggtagtt ctgttttctt tagcattcca   1080
aaagaagtga aaacaaaatt tgttttttat aaaagcggta cggatataga aacaatagc    1140
ctaatacaag taatgctaaa acttaactta ataaatcgtg acaatataaa actaatcagc   1200
gacatttaa                                                           1209
```

<210> SEQ ID NO 19
<211> LENGTH: 399
<212> TYPE: PRT

<213> ORGANISM: Unknown
<220> FEATURE:
<223> OTHER INFORMATION: Hd0053 glycosyltransferase family 80 (GT80),
    GT80 sialyltransferase

<400> SEQUENCE: 19

```
Met Leu Ile Gln Gln Asn Leu Glu Ile Tyr Leu Asp Tyr Ala Thr Ile
1               5                   10                  15

Pro Ser Leu Ala Cys Phe Met His Phe Ile Gln His Lys Asp Asp Val
            20                  25                  30

Asp Ser Ile Arg Leu Phe Gly Leu Ala Arg Phe Asp Ile Pro Gln Ser
        35                  40                  45

Ile Ile Asp Arg Tyr Pro Ala Asn His Leu Phe Tyr His Asn Ile Asp
50                  55                  60

Asn Arg Asp Leu Thr Ala Val Leu Asn Gln Leu Ala Asp Ile Leu Ala
65                  70                  75                  80

Gln Glu Asn Lys Arg Phe Gln Ile Asn Leu His Leu Asn Leu Phe His
                85                  90                  95

Ser Ile Asp Leu Phe Phe Ala Ile Tyr Pro Ile Tyr Gln Gln Tyr Gln
            100                 105                 110

His Lys Ile Ser Thr Ile Gln Leu Gln Leu Tyr Asp Asp Gly Ser Glu
        115                 120                 125

Gly Ile Val Thr Gln His Ser Leu Cys Lys Ile Ala Asp Leu Glu Gln
130                 135                 140

Leu Ile Leu Gln His Lys Asn Val Leu Glu Leu Thr Lys Gly
145                 150                 155                 160

Thr Ala Asn Val Pro Asn Pro Thr Leu Leu Arg Tyr Leu Trp Asn Asn
                165                 170                 175

Ile Ile Asp Ser Gln Phe His Leu Ile Ser Asp His Phe Leu Gln His
            180                 185                 190

Pro Lys Leu Gln Pro Leu Lys Arg Leu Leu Lys Arg Tyr Thr Ile Leu
        195                 200                 205

Asp Phe Thr Cys Tyr Pro Arg Phe Asn Ala Glu Gln Lys Gln Leu Leu
210                 215                 220

Lys Glu Ile Leu His Ile Ser Asn Glu Leu Glu Asn Leu Leu Lys Leu
225                 230                 235                 240

Leu Lys Gln His Asn Thr Phe Leu Phe Thr Gly Thr Thr Ala Phe Asn
                245                 250                 255

Leu Asp Gln Glu Lys Leu Asp Leu Leu Thr Gln Leu His Ile Leu Leu
            260                 265                 270

Leu Asn Glu His Gln Asn Pro His Ser Thr His Tyr Ile Gly Asn Asn
        275                 280                 285

Tyr Leu Leu Leu Ile Lys Gly His Ala Asn Ser Pro Ala Leu Asn His
290                 295                 300

Thr Leu Ala Leu His Phe Pro Asp Ala Ile Phe Leu Pro Ala Asn Ile
305                 310                 315                 320

Pro Phe Glu Ile Phe Ala Met Leu Gly Phe Thr Pro Asn Lys Met Gly
                325                 330                 335

Gly Phe Ala Ser Thr Ser Tyr Ile Asn Tyr Pro Thr Glu Asn Ile Asn
            340                 345                 350

His Leu Phe Phe Leu Thr Ser Asp Gln Pro Ser Ile Arg Thr Lys Trp
        355                 360                 365

Leu Asp Tyr Glu Lys Gln Phe Gly Leu Met Tyr Ser Leu Leu Ala Met
370                 375                 380
```

Gln Lys Ile Asn Glu Asp Gln Ala Phe Met Cys Thr Ile His Asn
385                 390                 395

<210> SEQ ID NO 20
<211> LENGTH: 1200
<212> TYPE: DNA
<213> ORGANISM: Unknown
<220> FEATURE:
<223> OTHER INFORMATION: Hd0053 glycosyltransferase family 80 (GT80),
      GT80 sialyltransferase

<400> SEQUENCE: 20

```
atgctgattc aacaaaatct tgaaatttat cttgattatg caactatccc aagcttggct      60
tgttttatgc atttattca acataaagat gatgttgata gcattcgttt atttggtcta     120
gcacgttttg atattccaca atcaattatc gatcgctatc ctgctaacca tttgttctac     180
cataacatcg ataatcgtga tcttactgcc gtattaaatc aactagcaga cattcttgcc     240
caagagaata agcgcttcca gatcaatcta catttaaacc tatttcacag catcgactta     300
ttttttgcca tttacccaat ctatcagcaa tatcaacata aaatttcaac tattcaatta     360
cagctttatg atgatggctc agaaggcatt gtcacccagc attctttatg taaaatagcc     420
gatcttgagc aactgatttt gcaacataaa atgtattac tagaactgct tactaaaggc     480
actgctaacg tgcctaatcc tactttgctc cgctatttat ggaataacat tattgatagc     540
caatttcact tgatttctga tcatttcctc cagcatccta attcaaacc gctaaaacgc     600
ttattaaaac gttatacaat tttagatttt acttgttatc ctcgctttaa tgctgagcaa     660
aaacaactcc tcaagaaat attgcatatc tctaatgagc tagaaaactt attaaaactg     720
ctcaaacagc ataatacttt tttatttacg ggcacaaccg cctttaactt ggatcaagaa     780
aaacttgact tattaacaca actacatatt ttgttgctta atgagcacca aaatccccac     840
tcaacgcatt acattggcaa taattattta ttactgatta aaggccacgc aaatagtcct     900
gctttgaatc atactttagc tttacatttt cctgatgcaa tattcctgcc tgctaatatt     960
ccatttgaga tctttgcaat gctaggtttt acgcccaata aatggggggg ctttgctagc    1020
actagctaca ttaattatcc aacagaaaat ataaatcatc tgttcttctt aacctctgat    1080
cagccgtcta ttcgaaccaa atggttggat tatgaaaagc agtttggctt aatgtatagt    1140
ttattagcca tgcaaaaaat caatgaagat caagcattta tgtgtacaat acataattaa    1200
```

<210> SEQ ID NO 21
<211> LENGTH: 675
<212> TYPE: PRT
<213> ORGANISM: Unknown
<220> FEATURE:
<223> OTHER INFORMATION: Pd2,6ST glycosyltransferase family 80 (GT80),
      GT80 sialyltransferase, Pd2_6ST

<400> SEQUENCE: 21

Met Lys Lys Ile Leu Thr Val Leu Ser Ile Phe Ile Leu Ser Ala Cys
 1               5                  10                  15

Asn Ser Asp Asn Thr Ser Leu Lys Glu Thr Val Ser Ser Asn Ser Ala
             20                  25                  30

Asp Val Val Glu Thr Glu Thr Tyr Gln Leu Thr Pro Ile Asp Ala Pro
         35                  40                  45

Ser Ser Phe Leu Ser His Ser Trp Glu Gln Thr Cys Gly Thr Pro Ile
     50                  55                  60

Leu Asn Glu Ser Asp Lys Gln Ala Ile Ser Phe Asp Phe Val Ala Pro
65                  70                  75                  80

```
Glu Leu Lys Gln Asp Glu Lys Tyr Cys Phe Thr Phe Lys Gly Ile Thr
                 85                  90                  95

Gly Asp His Arg Tyr Ile Thr Asn Thr Thr Leu Thr Val Val Ala Pro
            100                 105                 110

Thr Leu Glu Val Tyr Ile Asp His Ala Ser Leu Pro Ser Leu Gln Gln
        115                 120                 125

Leu Ile His Ile Ile Gln Ala Lys Asp Glu Tyr Pro Ser Asn Gln Arg
    130                 135                 140

Phe Val Ser Trp Lys Arg Val Thr Val Asp Ala Asp Asn Ala Asn Lys
145                 150                 155                 160

Leu Asn Ile His Thr Tyr Pro Leu Lys Gly Asn Asn Thr Ser Pro Glu
                165                 170                 175

Met Val Ala Ala Ile Asp Glu Tyr Ala Gln Ser Lys Asn Arg Leu Asn
            180                 185                 190

Ile Glu Phe Tyr Thr Asn Thr Ala His Val Phe Asn Asn Leu Pro Pro
        195                 200                 205

Ile Ile Gln Pro Leu Tyr Asn Asn Glu Lys Val Lys Ile Ser His Ile
    210                 215                 220

Ser Leu Tyr Asp Asp Gly Ser Ser Glu Tyr Val Ser Leu Tyr Gln Trp
225                 230                 235                 240

Lys Asp Thr Pro Asn Lys Ile Glu Thr Leu Glu Gly Glu Val Ser Leu
                245                 250                 255

Leu Ala Asn Tyr Leu Ala Gly Thr Ser Pro Asp Ala Pro Lys Gly Met
            260                 265                 270

Gly Asn Arg Tyr Asn Trp His Lys Leu Tyr Asp Thr Asp Tyr Tyr Phe
        275                 280                 285

Leu Arg Glu Asp Tyr Leu Asp Val Glu Ala Asn Leu His Asp Leu Arg
    290                 295                 300

Asp Tyr Leu Gly Ser Ser Ala Lys Gln Met Pro Trp Asp Glu Phe Ala
305                 310                 315                 320

Lys Leu Ser Asp Ser Gln Gln Thr Leu Phe Leu Asp Ile Val Gly Phe
                325                 330                 335

Asp Lys Glu Gln Leu Gln Gln Gln Tyr Ser Gln Ser Pro Leu Pro Asn
            340                 345                 350

Phe Ile Phe Thr Gly Thr Thr Thr Trp Ala Gly Gly Glu Thr Lys Glu
        355                 360                 365

Tyr Tyr Ala Gln Gln Gln Val Asn Val Ile Asn Asn Ala Ile Asn Glu
    370                 375                 380

Thr Ser Pro Tyr Tyr Leu Gly Lys Asp Tyr Asp Leu Phe Phe Lys Gly
385                 390                 395                 400

His Pro Ala Gly Gly Val Ile Asn Asp Ile Ile Leu Gly Ser Phe Pro
                405                 410                 415

Asp Met Ile Asn Ile Pro Ala Lys Ile Ser Phe Glu Val Leu Met Met
            420                 425                 430

Thr Asp Met Leu Pro Asp Thr Val Ala Gly Ile Ala Ser Ser Leu Tyr
        435                 440                 445

Phe Thr Ile Pro Ala Asp Lys Val Asn Phe Ile Val Phe Thr Ser Ser
    450                 455                 460

Asp Thr Ile Thr Asp Arg Glu Glu Ala Leu Lys Ser Pro Leu Val Gln
465                 470                 475                 480

Val Met Leu Thr Leu Gly Ile Val Lys Glu Lys Asp Val Leu Phe Trp
                485                 490                 495
```

```
Ala Asp His Lys Val Asn Ser Met Glu Val Ala Ile Asp Glu Ala Cys
            500                 505                 510
Thr Arg Ile Ile Ala Lys Arg Gln Pro Thr Ala Ser Asp Leu Arg Leu
        515                 520                 525
Val Ile Ala Ile Ile Lys Thr Ile Thr Asp Leu Glu Arg Ile Gly Asp
    530                 535                 540
Val Ala Glu Ser Ile Ala Lys Val Ala Leu Glu Ser Phe Ser Asn Lys
545                 550                 555                 560
Gln Tyr Asn Leu Leu Val Ser Leu Glu Leu Gly Gln His Thr Val
                565                 570                 575
Arg Met Leu His Glu Val Leu Asp Ala Phe Ala Arg Met Asp Val Lys
            580                 585                 590
Ala Ala Ile Glu Val Tyr Gln Glu Asp Asp Arg Ile Asp Gln Glu Tyr
        595                 600                 605
Glu Ser Ile Val Arg Gln Leu Met Ala His Met Met Glu Asp Pro Ser
    610                 615                 620
Ser Ile Pro Asn Val Met Lys Val Met Trp Ala Ala Arg Ser Ile Glu
625                 630                 635                 640
Arg Val Gly Asp Arg Cys Gln Asn Ile Cys Glu Tyr Ile Ile Tyr Phe
                645                 650                 655
Val Lys Gly Lys Asp Val Arg His Thr Lys Pro Asp Asp Phe Gly Thr
            660                 665                 670
Met Leu Asp
        675
```

<210> SEQ ID NO 22
<211> LENGTH: 2028
<212> TYPE: DNA
<213> ORGANISM: Unknown
<220> FEATURE:
<223> OTHER INFORMATION: Pd2,6ST glycosyltransferase family 80 (GT80), GT80 sialyltransferase, Pd2_6ST

<400> SEQUENCE: 22

```
atgaagaaaa tactgacagt tctatctatt tttattcttt cagcgtgtaa tagtgacaat    60
accagcttga agaaacggt aagctctaat tctgcagatg tagtagaaac agaaacttac   120
caactgacac cgattgatgc tcctagctct tttttatctc attcttggga gcaaacatgt   180
ggcacaccta tcttgaatga aagtgacaag caagcgtat cttttgattt tgttgctcca   240
gagttaaagc aagatgaaaa gtattgtttt acttttaaag gtattacagg cgatcatagg   300
tatatcacaa atacaacatt aactgttgtt gcacctacgc tagaagttta catcgatcat   360
gcatccttac catcgctaca gcagcttatc cacattattc aagcaaaaga tgaatacccca   420
agtaatcaac gttttgtctc ttggaagcgt gtaactgttg atgctgataa tgccaataag   480
ttaaacattc atacttatcc attaaaaggc aataatacct caccagaaat ggtggcagcg   540
attgatgagt atgctcagag caaaaatcga ttgaatatag agttctatac aaatacagct   600
catgttttta ataatttacc acctattatt caacctttat ataataacga aaggtgaaa    660
atttctcata ttagtttgta tgatgatggt tcttctgaat atgtaagttt atatcaatgg   720
aaagatacac aaataagat agaaacatta gaaggtgaag tatcgcttct tgctaattat   780
ttagcaggaa catctccgga tgcaccaaaa ggaatgggaa atcgttataa ctggcataaa   840
ttatatgaca ctgattatta cttttttgcgc gaagattacc ttgacgttga agcaaaccta   900
catgatttac gtgattattt aggctcttcc gcaaagcaaa tgccatggga tgaatttgct   960
```

-continued

```
aaattatctg attctcagca aacactattt ttagatattg tgggttttga taaagagcaa    1020
ttgcaacaac aatattcaca atccccacta ccaaacttta ttttaccgg cacaacaact     1080 tgggctgggg gggaaacgaa agagtattat gctcagcaac aagtaaatgt gattaataat    1140
gcgatcaatg aaactagccc ttattattta ggtaaagact acgatctatt tttcaagggg    1200
catcctgctg gtggcgttat taacgacatc attcttggaa gcttccctga tatgatcaat    1260
attccagcca agatttcatt tgaggtcttg atgatgacgg atatgttgcc tgatacagta    1320
gctggtattg cgagctctct gtacttcaca attcctgccg ataaagttaa ttttattgta    1380
tttacttcat ctgacactat tactgatcgt gaagaggctc ttaaatcacc attagtacaa    1440
gtgatgctaa cgttgggtat tgttaaagaa aaagatgttc tgttctgggc tgatcataaa    1500
gtaaactcga tggaagttgc cattgatgaa gcctgtactc ggatcattgc aaagcgacaa    1560
ccaaccgcga gtgatttacg cttggttatt gctattatca aaacaattac tgatcttgag    1620
cgtattggcg atgtggcaga agtattgct aaagtcgcat tagagagctt tagtaataag     1680
caatataacc tattggtttc tttagaatct cttggccagc atacggttcg aatgctgcat    1740
gaggtgttag atgcgtttgc tcgtatggat gttaaagccg caatagaagt gtaccaagaa    1800
gatgatcgaa ttgatcaaga gtatgagtcg atagtcagac agctaatggc ccatatgatg    1860
gaagatccaa gctcaattcc taatgtaatg aaagtgatgt gggcggcacg ttctattgag    1920
cgagtgggtg atcgctgtca aaacattgt gagtacatta tctactttgt gaagggtaaa     1980
gacgttcgcc ataccaaacc agatgatttt ggtactatgc tcgattaa                 2028
```

<210> SEQ ID NO 23
<211> LENGTH: 497
<212> TYPE: PRT
<213> ORGANISM: Unknown
<220> FEATURE:
<223> OTHER INFORMATION: P1ST6_JT-1 glycosyltransferase family 80
      (GT80), GT80 sialyltransferase

<400> SEQUENCE: 23

```
Met Lys Arg Ile Phe Cys Leu Val Ser Ala Ile Leu Leu Ser Ala Cys
  1               5                  10                  15

Asn Asp Asn Gln Asn Thr Val Asp Val Val Ser Thr Val Asn Asp
             20                  25                  30

Asn Val Ile Glu Asn Asn Thr Tyr Gln Val Lys Pro Ile Asp Thr Pro
         35                  40                  45

Thr Thr Phe Asp Ser Tyr Ser Trp Ile Gln Thr Cys Gly Thr Pro Ile
     50                  55                  60

Leu Lys Asp Asp Glu Lys Tyr Ser Leu Ser Phe Asp Phe Val Ala Pro
 65                  70                  75                  80

Glu Leu Asp Gln Asp Glu Lys Phe Cys Phe Glu Phe Thr Gly Asp Val
                 85                  90                  95

Asp Gly Lys Arg Tyr Val Thr Gln Thr Asn Leu Thr Val Val Ala Pro
            100                 105                 110

Thr Leu Glu Val Tyr Val Asp His Ala Ser Leu Pro Ser Leu Gln Gln
        115                 120                 125

Leu Met Lys Ile Ile Gln Gln Lys Asn Glu Tyr Ser Gln Asn Glu Arg
    130                 135                 140

Phe Ile Ser Trp Gly Arg Ile Arg Leu Thr Glu Asp Asn Ala Glu Lys
145                 150                 155                 160

Leu Asn Ala His Ile Tyr Pro Leu Ala Gly Asn Asn Thr Ser Gln Glu
                165                 170                 175
```

Leu Val Asp Ala Val Ile Asp Tyr Ala Asp Ser Lys Asn Arg Leu Asn
            180                 185                 190

Leu Glu Leu Asn Thr Asn Thr Gly His Ser Phe Arg Asn Ile Ala Pro
        195                 200                 205

Ile Leu Arg Ala Thr Ser Ser Lys Asn Asn Ile Leu Ile Ser Asn Ile
210                 215                 220

Asn Leu Tyr Asp Asp Gly Ser Ala Glu Tyr Val Ser Leu Tyr Asn Trp
225                 230                 235                 240

Lys Asp Thr Asp Asn Lys Ser Gln Lys Leu Ser Asp Ser Phe Leu Val
            245                 250                 255

Leu Lys Asp Tyr Leu Asn Gly Ile Ser Ser Glu Lys Pro Asn Gly Ile
        260                 265                 270

Tyr Ser Ile Tyr Asn Trp His Gln Leu Tyr His Ser Ser Tyr Tyr Phe
    275                 280                 285

Leu Arg Lys Asp Tyr Leu Thr Val Glu Thr Lys Leu His Asp Leu Arg
290                 295                 300

Glu Tyr Leu Gly Gly Ser Leu Lys Gln Met Ser Trp Asp Thr Phe Ser
305                 310                 315                 320

Gln Leu Ser Lys Gly Asp Lys Glu Leu Phe Leu Asn Ile Val Gly Phe
            325                 330                 335

Asp Gln Glu Lys Leu Gln Gln Glu Tyr Gln Gln Ser Glu Leu Pro Asn
        340                 345                 350

Phe Val Phe Thr Gly Thr Thr Thr Trp Ala Gly Gly Glu Thr Lys Glu
    355                 360                 365

Tyr Tyr Ala Gln Gln Gln Val Asn Val Asn Asn Ala Ile Asn Glu
370                 375                 380

Thr Ser Pro Tyr Tyr Leu Gly Arg Glu His Asp Leu Phe Phe Lys Gly
385                 390                 395                 400

His Pro Arg Gly Gly Ile Ile Asn Asp Ile Ile Leu Gly Ser Phe Asn
            405                 410                 415

Asn Met Ile Asp Ile Pro Ala Lys Val Ser Phe Glu Val Leu Met Met
        420                 425                 430

Thr Gly Met Leu Pro Asp Thr Val Gly Gly Ile Ala Ser Ser Leu Tyr
    435                 440                 445

Phe Ser Ile Pro Ala Glu Lys Val Ser Phe Ile Val Phe Thr Ser Ser
450                 455                 460

Asp Thr Ile Thr Asp Arg Glu Asp Ala Leu Lys Ser Pro Leu Val Gln
465                 470                 475                 480

Val Met Met Thr Leu Gly Ile Val Lys Glu Lys Asp Val Leu Phe Trp
            485                 490                 495

Cys

<210> SEQ ID NO 24
<211> LENGTH: 1494
<212> TYPE: DNA
<213> ORGANISM: Unknown
<220> FEATURE:
<223> OTHER INFORMATION: PlST6_JT-1 glycosyltransferase family 80
      (GT80), GT80 sialyltransferase

<400> SEQUENCE: 24
atgaaaagaa tattttgttt agtctctgct attttattat cagcatgtaa tgataatcag      60
aatacagtag atgtagttgt atctactgtg aatgataacg ttattgaaaa taatacttac     120
caagttaaac ccattgatac tccaactact tttgattcct attcttggat acaaacatgc     180

```
ggtactccaa tattaaaaga cgatgagaag tactctttga gttttgactt tgttgcacct       240
gagttagatc aagatgaaaa attctgcttt gagtttactg gtgatgttga tggtaagcgt       300
tatgttaccc aaacgaattt aactgttgtt gccccaacac tagaagtata tgtggatcat       360
gcatcattgc catcattaca gcagttaatg aaaataatcc aacagaaaaa tgagtattca       420
cagaatgagc gctttatttc ttggggacga attagactta cagaagataa tgcagaaaaa       480
ttaaatgccc atatatatcc attagctgga ataatacat cacaagaact tgtagatgca        540
gttattgact atgctgactc taaaaatcga ttaaatctag agcttaatac gaatacgggg       600
cactcttttc gtaacatcgc tccaatatta cgtgcaacat catcaaagaa taatatattg       660
atctcaaata ttaatctata cgatgatggt tcagctgaat atgttagcct ttataactgg       720
aaagatactg acaataaatc tcaaaaatta tctgatagtt ttttagttct aaagattat        780 ttaaatggta tttcttcgga aaaccgaat ggtatttaca gtatatataa ctggcatcag        840
ctatatcatt caagttacta ctttcttcga aaggattacc taactgttga aactaagtta       900
catgatttaa gagaatattt aggtggttcc ttaaagcaga tgtcatggga actttttcg        960 caattatcaa aaggtgataa agaactattt ttaaatattg ttgggtttga ccaagaaaaa      1020
ttacagcaag aatatcaaca atctgaattg cctaattttg ttttcacagg gacgacaaca      1080
tgggctggtg gtgaaactaa agaatattat gctcaacagc aggtaaatgt tgttaataat      1140
gcaataaatg agacaagtcc ttactatcta ggtagagagc atgatctttt ctttaaaggc      1200
catccaagag gaggaattat taatgatatt attttaggca gttttaataa tatgattgat      1260
attccagcta aggtatcatt tgaagtattg atgatgacag ggatgctacc tgatactgtt      1320
ggaggtattg caagctcttt gtattttca ataccagctg aaaaagtaag ttttattgta       1380
tttacatcgt ctgacactat tacagataga gaggacgcat taaaatcgcc tttagttcaa      1440
gtaatgatga cattgggtat tgtaaaagaa aaagatgttc tattttggtg ctga            1494
```

<210> SEQ ID NO 25
<211> LENGTH: 511
<212> TYPE: PRT
<213> ORGANISM: Unknown
<220> FEATURE:
<223> OTHER INFORMATION: PlST6_JT-2 glycosyltransferase family 80
      (GT80), GT80 sialyltransferase

<400> SEQUENCE: 25

```
Met Lys Arg Ile Phe Cys Leu Val Ser Ala Ile Leu Ser Ala Cys
  1               5                  10                  15

Asn Asp Asn Gln Asn Thr Val Asp Val Val Ser Thr Val Asn Asp
                 20                  25                  30

Asn Val Ile Glu Asn Asn Thr Tyr Gln Val Lys Pro Ile Asp Thr Pro
                 35                  40                  45

Thr Thr Phe Asp Ser Tyr Ser Trp Ile Gln Thr Cys Gly Thr Pro Ile
         50                  55                  60

Leu Lys Asp Asp Glu Lys Tyr Ser Leu Ser Phe Asp Phe Val Ala Pro
 65                  70                  75                  80

Glu Leu Asp Gln Asp Glu Lys Phe Cys Phe Glu Phe Thr Gly Asp Val
                 85                  90                  95

Asp Gly Lys Arg Tyr Val Thr Gln Thr Asn Leu Thr Val Val Ala Pro
                100                 105                 110

Thr Leu Glu Val Tyr Val Asp His Ala Ser Leu Pro Ser Leu Gln Gln
                115                 120                 125
```

Leu Met Lys Ile Ile Gln Gln Lys Asn Glu Tyr Ser Gln Asn Glu Arg
130                 135                 140

Phe Ile Ser Trp Gly Arg Ile Gly Leu Thr Glu Asp Asn Ala Glu Lys
145                 150                 155                 160

Leu Asn Ala His Ile Tyr Pro Leu Ala Gly Asn Asn Thr Ser Gln Glu
            165                 170                 175

Leu Val Asp Ala Val Ile Asp Tyr Ala Asp Ser Lys Asn Arg Leu Asn
            180                 185                 190

Leu Glu Leu Asn Thr Asn Thr Ala His Ser Phe Pro Asn Leu Ala Pro
            195                 200                 205

Ile Leu Arg Ile Ile Ser Ser Lys Ser Asn Ile Leu Ile Ser Asn Ile
210                 215                 220

Asn Leu Tyr Asp Asp Gly Ser Ala Glu Tyr Val Asn Leu Tyr Asn Trp
225                 230                 235                 240

Lys Asp Thr Glu Asp Lys Ser Val Lys Leu Ser Asp Ser Phe Leu Val
            245                 250                 255

Leu Lys Asp Tyr Phe Asn Gly Ile Ser Ser Glu Lys Pro Ser Gly Ile
            260                 265                 270

Tyr Gly Arg Tyr Asn Trp His Gln Leu Tyr Asn Thr Ser Tyr Tyr Phe
            275                 280                 285

Leu Arg Lys Asp Tyr Leu Thr Val Glu Pro Gln Leu His Asp Leu Arg
290                 295                 300

Glu Tyr Leu Gly Gly Ser Leu Lys Gln Met Ser Trp Asp Gly Phe Ser
305                 310                 315                 320

Gln Leu Ser Lys Gly Asp Lys Glu Leu Phe Leu Asn Ile Val Gly Phe
            325                 330                 335

Asp Gln Glu Lys Leu Gln Gln Glu Tyr Gln Gln Ser Glu Leu Pro Asn
            340                 345                 350

Phe Val Phe Thr Gly Thr Thr Thr Trp Ala Gly Gly Glu Thr Lys Glu
            355                 360                 365

Tyr Tyr Ala Gln Gln Gln Val Asn Val Val Asn Asn Ala Ile Asn Glu
370                 375                 380

Thr Ser Pro Tyr Tyr Leu Gly Arg Glu His Asp Leu Phe Phe Lys Gly
385                 390                 395                 400

His Pro Arg Gly Gly Ile Ile Asn Asp Ile Ile Leu Gly Ser Phe Asn
            405                 410                 415

Asn Met Ile Asp Ile Pro Ala Lys Val Ser Phe Glu Val Leu Met Met
            420                 425                 430

Thr Gly Met Leu Pro Asp Thr Val Gly Gly Ile Ala Ser Ser Leu Tyr
            435                 440                 445

Phe Ser Ile Pro Ala Glu Lys Val Ser Phe Ile Val Phe Thr Ser Ser
450                 455                 460

Asp Thr Ile Thr Asp Arg Glu Asp Ala Leu Lys Ser Pro Leu Val Gln
465                 470                 475                 480

Val Met Met Thr Leu Gly Ile Val Lys Glu Lys Asp Val Leu Phe Trp
            485                 490                 495

Ser Asp Leu Pro Asp Cys Ser Ser Gly Val Cys Ile Ala Gln Tyr
            500                 505                 510

<210> SEQ ID NO 26
<211> LENGTH: 1536
<212> TYPE: DNA
<213> ORGANISM: Unknown
<220> FEATURE:

<223> OTHER INFORMATION: PlST6_JT-2 glycosyltransferase family 80
(GT80), GT80 sialyltransferase

<400> SEQUENCE: 26

```
atgaaaagaa tattttgttt agtctctgct attttattat cagcatgtaa tgataatcag      60
aatacagtag atgtagttgt atctactgtg aatgataacg ttattgaaaa taatacttac     120
caagttaaac ccattgatac tccaactact tttgattcct attcttggat acaaacatgc     180
ggtactccaa tattaaaaga cgatgagaag tactctttga gttttgactt tgttgcacct     240
gagttagatc aagatgaaaa attctgcttt gagtttactg gtgatgttga tggtaagcgt     300
tatgttaccc aaactaattt gactgttgtt gccccaacac tagaagtata tgtggatcat     360
gcatcattgc catcattaca gcagttaatg aaaataatcc aacagaaaaa tgagtattca     420
cagaatgagc gctttatttc ttggggacga attggactta cagaagataa cgcagaaaaa     480
ttaaatgccc atatatatcc attagctgga ataacacat cacaagaact tgtagatgca      540
gttattgact atgctgactc taaaaatcga ttaaatctag agcttaatac gaatacagcg     600
cattcttttc caaatctagc accaatatta cgtataatat catcaaagag taatatacta     660
atttcaaata ttaatttata tgatgatggt tctgcagagt atgttaacct ttataactgg     720
aaagatactg aagataaatc cgtaaaatta tcggatagtt ttttagttct aaaagattat     780
tttaatggta tttcgtcgga aaagccttct ggtatttatg gcgatataa ttggcatcag     840
ctatacaata caagttacta ttttcttcga aaagactact taacagttga acctcagtta     900
catgacttaa gagaatactt aggtggttct ttaaaacaaa tgtcatggga tggttttttct     960
caattatcaa aaggtgataa agaactattt ttaaatattg ttgggtttga ccaagaaaaa    1020
ttacagcaag aatatcaaca atctgaattg cctaattttg ttttcacagg acgacaaca    1080
tgggctggtg gtgaaactaa agaatattat gctcaacagc aggtaaatgt tgttaataat    1140
gcaataaatg agacaagtcc ttactatcta ggtagagagc atgatctttt cttttaaaggt    1200
catccaagag gaggaattat taatgatatt atttttaggca gttttaataa tatgattgat    1260
attccagcta aggtatcatt tgaagtattg atgatgacag gatgctacc tgatactgtt    1320
ggaggtattg caagctcttt gtattttca ataccagctg aaaaagtaag ttttattgta    1380
tttacatcgt ctgacactat tacagataga gaggacgcat taaaatcgcc tttagttcaa    1440
gtaatgatga cattgggtat tgtaaaagaa aagatgttc tattttggtc tgacttacca    1500
gattgttcta gtggtgtgtg tattgctcaa tattag                              1536
```

<210> SEQ ID NO 27
<211> LENGTH: 409
<212> TYPE: PRT
<213> ORGANISM: Unknown
<220> FEATURE:
<223> OTHER INFORMATION: Pp_Pst3-1 glycosyltransferase family 80 (GT80),
GT80 sialyltransferase

<400> SEQUENCE: 27

```
Met Phe Val Phe Cys Lys Lys Ile Phe Phe Leu Ile Phe Ile Ser Leu
 1               5                  10                  15

Met Ile Leu Gly Gly Cys Asn Ser Asp Ser Lys His Asn Asn Ser Asp
            20                  25                  30

Gly Asn Ile Thr Lys Asn Lys Thr Ile Glu Val Tyr Val Asp Arg Ala
        35                  40                  45

Thr Leu Pro Thr Ile Gln Gln Met Thr Gln Ile Ile Asn Glu Asn Ser
    50                  55                  60
```

```
Asn Asn Lys Lys Leu Ile Ser Trp Ser Arg Tyr Pro Ile Asn Asp Glu
 65                  70                  75                  80

Thr Leu Leu Glu Ser Ile Asn Gly Ser Phe Lys Asn Arg Pro Glu
                 85                  90                  95

Leu Ile Lys Ser Leu Asp Ser Met Ile Leu Thr Asn Glu Ile Lys Lys
            100                 105                 110

Val Ile Ile Asn Gly Asn Thr Leu Trp Ala Val Asp Val Asn Ile
            115                 120                 125

Ile Lys Ser Ile Glu Ala Leu Gly Lys Lys Thr Glu Ile Glu Leu Asn
130                 135                 140

Phe Tyr Asp Asp Gly Ser Ala Glu Tyr Val Arg Leu Tyr Asp Phe Ser
145                 150                 155                 160

Arg Leu Pro Glu Ser Glu Gln Glu Tyr Lys Ile Ser Leu Ser Lys Asp
                165                 170                 175

Asn Ile Gln Ser Ser Ile Asn Gly Thr Gln Pro Phe Asp Asn Ser Ile
                180                 185                 190

Glu Asn Ile Tyr Gly Phe Ser Gln Leu Tyr Pro Thr Thr Tyr His Met
            195                 200                 205

Leu Arg Ala Asp Ile Phe Glu Thr Asn Leu Pro Leu Thr Ser Leu Lys
210                 215                 220

Arg Val Ile Ser Asn Asn Ile Lys Gln Met Lys Trp Asp Tyr Phe Thr
225                 230                 235                 240

Thr Phe Asn Ser Gln Gln Lys Asn Lys Phe Tyr Asn Phe Thr Gly Phe
                245                 250                 255

Asn Pro Glu Lys Ile Lys Glu Gln Tyr Lys Ala Ser Pro His Glu Asn
                260                 265                 270

Phe Ile Phe Ile Gly Thr Asn Ser Gly Thr Ala Thr Ala Glu Gln Gln
            275                 280                 285

Ile Asp Ile Leu Thr Glu Ala Lys Lys Pro Asp Ser Pro Ile Ile Thr
290                 295                 300

Asn Ser Ile Gln Gly Leu Asp Leu Phe Phe Lys Gly His Pro Ser Ala
305                 310                 315                 320

Thr Tyr Asn Gln Gln Ile Ile Asp Ala His Asn Met Ile Glu Ile Tyr
                325                 330                 335

Asn Lys Ile Pro Phe Glu Ala Leu Ile Met Thr Asp Ala Leu Pro Asp
                340                 345                 350

Ala Val Gly Gly Met Gly Ser Ser Val Phe Phe Ser Leu Pro Asn Thr
            355                 360                 365

Val Glu Asn Lys Phe Ile Phe Tyr Lys Ser Asp Thr Asp Ile Glu Asn
            370                 375                 380

Asn Ala Leu Ile Gln Val Met Ile Glu Leu Asn Ile Val Asn Arg Asn
385                 390                 395                 400

Asp Val Lys Leu Ile Ser Asp Leu Gln
                405

<210> SEQ ID NO 28
<211> LENGTH: 1230
<212> TYPE: DNA
<213> ORGANISM: Unknown
<220> FEATURE:
<223> OTHER INFORMATION: Pp_Pst3-1 glycosyltransferase family 80 (GT80),
      GT80 sialyltransferase

<400> SEQUENCE: 28
atgttcgttt tttgtaaaaa aatatttttt ttgattttta tttcactaat gattctgggg      60
```

```
ggctgtaata gtgactctaa gcacaataac tcagatggta atattacaaa aaataaaaca      120
atagaagttt atgttgatag agcaacatta ccaactattc aacaaatgac tcagattatt      180
aatgaaaatt caataataa gaaacttatt tcttggtctc gatacccat taatgatgaa        240 acgttattag aatcaattaa tggatcattt tttaaaaata ggccagagct aattaaatct      300
cttgattcta tgatacttac taatgagatt aaaaaagtaa tcattaatgg taataccta      360 tgggcagtag atgtcgttaa tattataaaa tcaattgaag ctcttggaaa aaaacagag       420 attgaactaa attttatga tgacggtagt gcagaatatg ttcgattata tgactttca       480 agattacctg aatcagaaca agaatataaa atatccttat caaaggataa cattcaatca     540
agtataaatg aactcaacc atttgataac tcaattgaaa atatctatgg cttttcgcag      600
ttatacccaa caacatatca tatgctcaga gcagatattt ttgaaactaa tttacctttg     660
acctctttga aaagagtaat atcaaataat attaagcaaa tgaaatggga ttattttaca    720
acttttaatt cccaacagaa gaataaattc tataatttca cgggatttaa cccagaaaaa    780
attaaggaac aatataaagc aagccctcat gaaaattta tttttatcgg aactaattca    840
ggaacagcaa cggcagagca acaaatagat attcttacag aagctaaaaa gccagatagc    900
ccgataataa ctaattcaat tcaaggattg gatttgtttt tcaaaggaca tccgagtgca    960
acttataatc aacaaatcat tgatgctcat aaatatgattg aaatttataa taagatacca  1020
tttgaagctc taataatgac tgatgcattg cctgatgctg tcggtggaat gggaagttcg   1080 gtattttta gcttgccaaa tacagtagag aataaattta ttttttataa aagtgatacg    1140
gatattgaaa ataatgctct tatacaagta atgattgaac tgaatatcgt taatagaaat   1200
gatgttaagt tgataagtga tttgcagtaa                                    1230
```

<210> SEQ ID NO 29
<211> LENGTH: 409
<212> TYPE: PRT
<213> ORGANISM: Unknown
<220> FEATURE:
<223> OTHER INFORMATION: Pp_Pst3-2 glycosyltransferase family 80 (GT80),
      GT80 sialyltransferase

<400> SEQUENCE: 29

Met Leu Val Phe Cys Lys Lys Met Phe Phe Ser Val Phe Ile Ser Leu
1               5                   10                  15

Met Ile Leu Gly Gly Cys Asn Ser Asp Ser Asn His Asn Asn Ser Asp
            20                  25                  30

Gly Asn Ile Thr Lys Asn Lys Thr Ile Glu Val Tyr Val Asp Arg Ala
        35                  40                  45

Thr Leu Pro Thr Ile Gln Gln Met Thr Gln Ile Asn Glu Asn Ser
    50                  55                  60

Asn Asn Lys Lys Leu Ile Ser Trp Ser Arg Tyr Pro Ile Asn Asp Glu
65                  70                  75                  80

Glu Leu Leu Glu Ser Ile Asn Gly Ser Phe Phe Lys Asn Asn Ser Glu
                85                  90                  95

Leu Ile Lys Ser Leu Asp Ser Met Ile Leu Thr Asn Asp Ile Lys Lys
            100                 105                 110

Val Ile Ile Asn Gly Asn Thr Leu Trp Ala Ala Asp Val Val Asn Ile
        115                 120                 125

Ile Lys Ser Ile Glu Ala Phe Gly Lys Lys Thr Glu Ile Glu Leu Asn
    130                 135                 140

Phe Tyr Asp Asp Gly Ser Ala Glu Tyr Val Arg Leu Tyr Asp Phe Ser
145                 150                 155                 160

Lys Leu Pro Glu Ser Glu Gln Gly Tyr Lys Ile Ser Leu Ser Lys Asp
                165                 170                 175

Asn Ile Leu Ser Ser Ile Asn Gly Thr Gln Pro Phe Glu Asn Val Val
            180                 185                 190

Glu Asn Ile Tyr Gly Phe Ser Gln Leu Tyr Pro Thr Thr Tyr His Met
        195                 200                 205

Leu Arg Ala Asp Ile Phe Glu Thr Asn Leu Pro Leu Arg Ser Leu Lys
210                 215                 220

Gly Val Leu Ser Asn Asn Ile Lys Gln Met Lys Trp Asp Tyr Phe Lys
225                 230                 235                 240

Thr Phe Asn Ser Gln Gln Lys Asp Lys Phe Tyr Asn Phe Thr Gly Phe
                245                 250                 255

Asn Pro Asp Glu Ile Met Glu Gln Tyr Lys Ala Ser Pro Asn Lys Asn
            260                 265                 270

Phe Ile Phe Val Gly Thr Asn Ser Gly Thr Ala Thr Ala Glu Gln Gln
        275                 280                 285

Ile Asp Ile Leu Thr Glu Ala Lys Asn Pro Asn Ser Pro Ile Ile Thr
290                 295                 300

Lys Ser Ile Gln Gly Phe Asp Leu Phe Phe Lys Gly His Pro Ser Ala
305                 310                 315                 320

Thr Tyr Asn Lys Gln Ile Ile Asp Ala His Asn Met Ile Glu Ile Tyr
                325                 330                 335

Asn Lys Ile Pro Phe Glu Ala Leu Ile Met Thr Asp Ala Leu Pro Asp
            340                 345                 350

Ala Val Gly Gly Met Gly Ser Ser Val Phe Phe Ser Leu Pro Asn Thr
        355                 360                 365

Val Glu Asn Lys Phe Ile Phe Tyr Lys Ser Asp Thr Asp Ile Glu Asn
370                 375                 380

Asn Ala Leu Ile Gln Val Met Ile Glu Leu Asn Ile Val Asn Arg Asn
385                 390                 395                 400

Asp Val Lys Leu Ile Ser Asp Leu Gln
                405

<210> SEQ ID NO 30
<211> LENGTH: 1230
<212> TYPE: DNA
<213> ORGANISM: Unknown
<220> FEATURE:
<223> OTHER INFORMATION: Pp_Pst3-2 glycosyltransferase family 80 (GT80),
    GT80 sialyltransferase

<400> SEQUENCE: 30
atgctcgttt tttgtaaaaa aatgtttttt tcagttttta tttcactaat gattcttggg      60
ggatgtaata gtgactctaa tcacaataac tcagatggaa atattacaaa aaataaaaca     120
atagaagttt atgttgatag agcaacatta ccaactattc aacaaatgac tcagattatt     180
aatgaaaatt caaataacaa aaaactgatt tcttggtcac gatacctat taatgatgaa      240 gagttattgg aatcaattaa tggctcattt ttaaaaaata attcagagct aattaagtct     300
cttgattcta tgatacttac taatgatata aaaaagtaa tcatcaacgg taataccta       360 tgggcagcag atgtcgttaa tattataaaa tcaattgaag cttttggaaa aaaacagaa      420 atagaactaa attttatga tgatggtagt gcggaatatg ttcgtttata tgacttttca     480
aaattaccag aatcagaaca ggaatataaa atttctttgt caaaggataa cattctttca    540

```
agtataaatg gaactcaacc atttgaaaat gttgttgaaa acatttatgg tttttctcag    600
ttatacccaa cgacatatca tatgctcaga gctgatattt ttgaaactaa tttaccattg    660
agatccttga aaggggtatt atcaaataat attaagcaaa tgaaatggga ctactttaaa    720
actttcaatt cacagcagaa ggataaattt tataatttta caggctttaa cccagacgaa    780
attatggagc aatataaagc aagtcctaat aaaaacttta tttttgtcgg tactaattca    840
ggaactgcaa cagcagagca acaaattgat attctgacag aagctaaaaa tccaaatagt    900
cctataataa ctaaatcaat tcaagggttt gatttgtttt ttaaaggaca tcctagtgca    960
acttataata aacaaatcat agatgctcat aatatgattg aaatttataa taagatacca   1020
tttgaagctc taatcatgac tgatgcattg cctgatgctg tcggtggaat gggaagttcg   1080
gtatttttta gcttgccaaa tacagtagag aataaattta ttttttataa aagtgatacg   1140
gatattgaaa ataatgctct tatacaagtt atgattgaac taaatattgt caatagaaat   1200
gatgttaagt tgataagtga tttgcagtaa                                    1230
```

<210> SEQ ID NO 31
<211> LENGTH: 5
<212> TYPE: PRT
<213> ORGANISM: Artificial Sequence
<220> FEATURE:
<223> OTHER INFORMATION: synthetic sialyltransferase domain sialyltransferase motif A, Pasteurella multicoda glycosyltransferase family 80 (GT80), GT80 sialyltransferase amino acid positions 139-143

<400> SEQUENCE: 31

```
Tyr Asp Asp Gly Ser
 1               5
```

<210> SEQ ID NO 32
<211> LENGTH: 38
<212> TYPE: DNA
<213> ORGANISM: Artificial Sequence
<220> FEATURE:
<223> OTHER INFORMATION: synthetic site-directed mutagenesis primer for E271F

<400> SEQUENCE: 32

```
accggcacga caacttggtt tggaaatacc gatgtgcg                              38
```

<210> SEQ ID NO 33
<211> LENGTH: 45
<212> TYPE: DNA
<213> ORGANISM: Artificial Sequence
<220> FEATURE:
<223> OTHER INFORMATION: synthetic site-directed mutagenesis primer for R313Y

<400> SEQUENCE: 33

```
atctacttta aagggcatcc ttatggtggt gaaattaatg actac                      45
```

<210> SEQ ID NO 34
<211> LENGTH: 6
<212> TYPE: PRT
<213> ORGANISM: Artificial Sequence
<220> FEATURE:
<223> OTHER INFORMATION: synthetic His-6 tag

<400> SEQUENCE: 34

```
His His His His His His
1               5
```

```
<210> SEQ ID NO 35
<211> LENGTH: 46
<212> TYPE: DNA
<213> ORGANISM: Artificial Sequence
<220> FEATURE:
<223> OTHER INFORMATION: synthetic site-directed mutagenesis primer for
      M144D

<400> SEQUENCE: 35
aatctttatg acgatggctc agatgaatat gttgatttag aaaaag                    46

<210> SEQ ID NO 36
<211> LENGTH: 46
<212> TYPE: DNA
<213> ORGANISM: Artificial Sequence
<220> FEATURE:
<223> OTHER INFORMATION: synthetic site-directed mutagenesis primer for
      M144H

<400> SEQUENCE: 36
aatctttatg acgatggctc acatgaatat gttgatttag aaaaag                    46

<210> SEQ ID NO 37
<211> LENGTH: 45
<212> TYPE: DNA
<213> ORGANISM: Artificial Sequence
<220> FEATURE:
<223> OTHER INFORMATION: synthetic site-directed mutagenesis primer for
      A35D

<400> SEQUENCE: 37
atcacgctgt atttagatcc tgattcctta ccggcattaa atcag                     45

<210> SEQ ID NO 38
<211> LENGTH: 45
<212> TYPE: DNA
<213> ORGANISM: Artificial Sequence
<220> FEATURE:
<223> OTHER INFORMATION: synthetic site-directed mutagenesis primer for
      A35H

<400> SEQUENCE: 38
atcacgctgt atttagatcc tcattcctta ccggcattaa atcag                     45
```

PMST1 MUTANTS FOR CHEMOENZYMATIC SYNTHESIS OF SIALYL LEWIS X COMPOUNDS

CROSS-REFERENCE TO RELATED APPLICATIONS

This application is the U.S. National Stage Entry under §371 of International Application No. PCT/US2012/049748, filed Aug. 6, 2012, which claims priority to U.S. Provisional Application No. 61/515,702, filed Aug. 5, 2011 which is incorporated in its entirety herein for all purposes.

STATEMENT AS TO RIGHTS TO INVENTIONS MADE UNDER FEDERALLY SPONSORED RESEARCH AND DEVELOPMENT

This invention was made with Government support under Grant Nos. R01GM076360 awarded by National Institutes of Health. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -2106-1.TXT, created on Jun. 16, 2014, 86,016 bytes, machine format IBM-PC, MS-Windows operating system, is hereby incorporated by reference in its entirety for all purposes.

BACKGROUND OF THE INVENTION

Glycosyltransferase-catalyzed reactions have gained increasing attention and application for the synthesis of complex carbohydrates and glycoconjugates. Most mammalian glycosyltransferases suffer from no or low expression in *E. coli* systems and more restricted substrate specificity. In comparison, bacterial glycosyltransferases are generally easier to access using *E. coli* expression systems and have more promiscuous substrate flexibility. Nevertheless, despite the discovery of many bacterial glycosyltransferases which have promiscuities for both donor and acceptor substrates, the application of glycosyltransferases in the synthesis of carbohydrate-containing structures is limited by the availability and the substrate specificity of wild-type enzymes.

For example, sialyltransferases, the key enzymes that catalyze the transfer of a sialic acid residue from cytidine 5'-monophosphate-sialic acid (CMP-sialic acid) to an acceptor, have been commonly used for the synthesis of sialic acid-containing structures. Sialyl Lewis$^x$ [SLe$^x$, Siaα2-3Galβ1-4(Fucα1-3)GlcNAcβOR] is an important carbohydrate epitope involved in inflammation as well as adhesion and metastasis of cancer cells. It is a well-known tumor-associated carbohydrate antigen and has been used as a candidate for cancer vaccine. The biosynthesis of SLe$^x$ involves the formation of Siaα2-3Galβ1-4GlcNAcβOR catalyzed by an α2-3-sialyltransferase followed by an α1-3-fucosyltransferase-catalyzed fucosylation. This biosynthetic sequence usually cannot be altered as common α2-3-sialyltransferases do not use fucose-containing Lewis$^x$ [Le$^x$, Galβ1-4(Fucα1-3)GlcNAcβOR] as a substrate.

As common terminal monosaccharides, sialic acids constitute a family of great structural diversity. So far, more than 50 structurally distinct sialic acid forms have been identified in nature. To obtain SLe$^x$ with different sialic acid forms to elucidate the biological significance of naturally occurring sialic acid modifications, an efficient enzymatic approach is to use Le$^x$ [Galβ1-4(Fucα1-3)GlcNAcβOR] as a fucose-containing acceptor to add different sialic acid forms by a suitable α2-3-sialyltransferase. This process of introducing different forms of sialic acid onto the common fucosylated acceptor Le$^x$ in the last step has significant advantages compared to the normal SLe$^x$ biosynthetic pathway in which fucosylation is the last glycosylation process. It not only simplifies the synthetic scheme as a less number of reactions are needed, but also makes the purification process much easier as negatively charged SLe$^x$ product is separated from neutral Le$^x$ oligosaccharide instead of separating both negatively charged oligosaccharides SLe$^x$ and non-fucosylated sialosides if fucosylation occurs in the last step.

We and others have demonstrated that a myxoma virus α2-3-sialyltransferase can use Le$^x$ as an acceptor substrate for synthesizing SLe$^x$. Nevertheless, the low expression level of the enzyme in *E. coli* (<0.1 mg L$^{-1}$ culture) limits its application in preparative and large-scale synthesis of SLe$^x$.

We have previously shown that a multifunctional α2-3-sialyltransferase from *Pasteurella multocida* (PmST1) has a good expression level in *E. coli* (100 mg L$^{-1}$ culture) (*J. Am. Chem. Soc.* 2005, 127, 17618-17619.). It can use Le$^x$ as an acceptor for the synthesis of SLe$^x$ but the yields are poor (<20%) in spite of different conditions tested. What is needed, therefore, are α2-3-sialyltransferases having good α2-3-sialyltransferase activity with good expression levels, and lowered α2-3-sialidase or donor substrate hydrolysis activity. Surprisingly, the present invention meets this and other needs.

BRIEF SUMMARY OF THE INVENTION

In some embodiments, the present invention provides an isolated glycosyltransferase, wherein the amino acid of the glycosyltransferase corresponding to position 120 of SEQ ID NO:1 is any amino acid other than M, the amino acid the glycosyltransferase corresponding to position 247 of SEQ ID NO:1 is any amino acid other than E, or the amino acid the glycosyltransferase corresponding to position 289 of SEQ ID NO:1 is any amino acid other than R. The glycosyltransferase of the present invention has decreased α2-3 sialidase or donor substrate hydrolysis activity compared to a control glycosyltransferase, wherein the amino acid of the control glycosyltransferase corresponding to position 120 of SEQ ID NO:1 is M, the amino acid of the control glycosyltransferase corresponding to position 247 of SEQ ID NO:1 is E, and the amino acid of the control glycosyltransferase corresponding to position 289 of SEQ ID NO:1 is R. Finally, the glycosyltransferase of the present invention can be a member of the glycosyltransferase family 80 (GT80).

In some embodiments, the present invention provides a recombinant nucleic acid encoding an isolated glycosyltransferase of the present invention.

In some embodiments, the present invention provides a cell including a recombinant nucleic acid of the present invention.

In some embodiments, the present invention provide a method of preparing an oligosaccharide, the method including forming a reaction mixture including an acceptor sugar, a donor substrate of a sugar moiety and a nucleotide, and the glycosyltransferase of the present invention, under conditions sufficient to transfer the sugar moiety from the donor substrate to the acceptor sugar, thereby forming the oligosaccharide.

Figure 1:
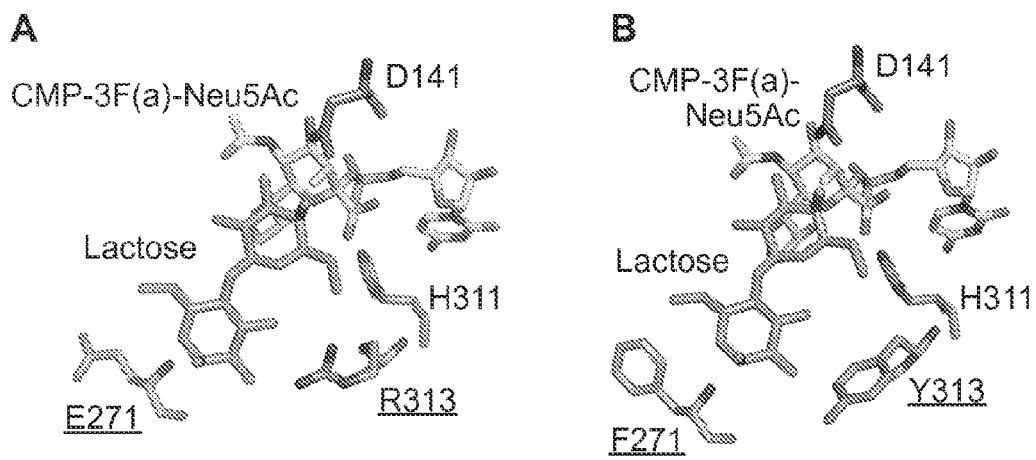
FIG. 1 shows the ternary crystal structure of PmST1 (PDB ID: 2IHZ) with bound CMP-3F(axial)-Neu5Ac and lactose (FIG. 1A) and the structure of the modeled PmST1 double mutant E271F/R313Y of PmST1 wild type sequence SEQ ID NO: 13 (FIG. 1B). The mutation sites are underlined. The mutant structure was obtained from automated homology modeling using Swiss-Model.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "mutant," in the context of glycosyltransferases of the present invention, means a polypeptide, typically recombinant, that comprises one or more amino acid substitutions relative to a corresponding, naturally-occurring or unmodified glycosyltransferase, such as an alpha2-3 sialyltransferase.

In the context of glycosyltransferases, "corresponding to" another sequence (e.g., regions, fragments, nucleotide or amino acid positions, or the like) is based on the convention of numbering according to nucleotide or amino acid position number and then aligning the sequences in a manner that maximizes the percentage of sequence identity. Because not all positions within a given "corresponding region" need be identical, non-matching positions within a corresponding region may be regarded as "corresponding positions." Accordingly, as used herein, referral to an "amino acid of the glycosyltransferase corresponding to position [X]" of a specified glycosyltransferase refers to equivalent positions, based on alignment, in other glycosyltransferases and structural homologues and families. In some embodiments of the present invention, "correspondence" of amino acid positions are determined with respect to a region of the glycosyltransferase comprising one or more motifs of SEQ ID NO:1, 13, 15, 17, 19, 21, 23, 25, 27 or 29. When a glycosyltransferase polypeptide sequence differs from SEQ ID NO:1, 13, 15, 17, 19, 21, 23, 25, 27 or 29 (e.g., by changes in amino acids or addition or deletion of amino acids), it may be that a particular mutation associated with improved activity as discussed herein will not be in the same position number as it is in SEQ ID NO:1, 13, 15, 17, 19, 21, 23, 25, 27 or 29.

A nucleic acid is "operably linked" when it is placed into a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation.

As used herein, "percent sequence identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% identity over a specified region), when compared and aligned for maximum correspondence over a comparison window, or designated region as measured using one of the following sequence comparison algorithms or by manual alignment and visual inspection. These definitions also refer to the complement of a test sequence. Optionally, the identity exists over a region that is at least about 50 nucleotides in length, or more typically over a region that is 100 to 500 or 1000 or more nucleotides in length.

The terms "similarity" or "percent similarity," in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarly exists over a region that is at least about 50 amino acids in length, or more typically over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Algorithms suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873-87, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, typically less than about 0.01, and more typically less than about 0.001.

"Recombinant," as used herein, refers to an amino acid sequence or a nucleotide sequence that has been intentionally modified by recombinant methods. By the term "recombinant nucleic acid" herein is meant a nucleic acid, originally formed in vitro, in general, by the manipulation of a nucleic acid by endonucleases, in a form not normally found in nature. Thus an isolated, mutant glycosyltransferase nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. A "recombinant protein" is a protein made using recombinant techniques, i.e., through the expression of a recombinant nucleic acid as depicted above.

The term "vector" refers to a piece of DNA, typically double-stranded, which may have inserted into it a piece of foreign DNA. The vector may be, for example, of plasmid origin. Vectors contain "replicon" polynucleotide sequences that facilitate the autonomous replication of the vector in a host cell. Foreign DNA is defined as heterologous DNA, which is DNA not naturally found in the host cell, which, for example, replicates the vector molecule, encodes a selectable or screenable marker, or encodes a transgene. The vector is used to transport the foreign or heterologous DNA into a suitable host cell. Once in the host cell, the vector can replicate independently of or coincidental with the host chromosomal DNA, and several copies of the vector and its inserted DNA can be generated. In addition, the vector can also contain the necessary elements that permit transcription of the inserted DNA into an mRNA molecule or otherwise cause replication of the inserted DNA into multiple copies of RNA. Some expression vectors additionally contain sequence elements adjacent to the inserted DNA that increase the half-life of the expressed mRNA and/or allow translation of the mRNA into a protein molecule. Many molecules of mRNA and polypeptide encoded by the inserted DNA can thus be rapidly synthesized.

The term "nucleotide," in addition to referring to the naturally occurring ribonucleotide or deoxyribonucleotide monomers, shall herein be understood to refer to related structural variants thereof, including derivatives and analogs, that are functionally equivalent with respect to the particular context in which the nucleotide is being used (e.g., hybridization to a complementary base), unless the context clearly indicates otherwise.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (*Science* 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

As used herein, the term "oligosaccharide" refers to a compound containing at least two sugars covalently linked together. Oligosaccharides include disaccharides, trisaccharides, tetrasachharides, pentasaccharides, hexasaccharides, heptasaccharides, octasaccharides, and the like. Covalent linkages generally consist of glycosidic linkages (i.e., C—O—C bonds) formed from the hydroxyl groups of adjacent sugars. Linkages can occur between the 1-carbon and the 4-carbon of adjacent sugars (i.e., a 1-4 linkage), the 1-carbon and the 3-carbon of adjacent sugars (i.e., a 1-3 linkage), the 1-carbon and the 6-carbon of adjacent sugars (i.e., a 1-6 linkage), or the 1-carbon and the 2-carbon of adjacent sugars (i.e., a 1-2 linkage). A sugar can be linked within an oligosaccharide such that the anomeric carbon is in the $\alpha$- or $\beta$-configuration. The oligosaccharides prepared according to the methods of the invention can also include linkages between carbon atoms other than the 1-, 2-, 3-, 4-, and 6-carbons.

"Acceptor sugar" refers a sugar that accepts the sugar being added. For example, the acceptor sugar can be an oligosaccharide, such as a fucosylated oligosaccharide, that accepts a sialic acid or analog thereof.

"Donor substrate" refers to a compound having a nucleotide and the sugar that is added to the acceptor, where the sugar and nucleotide are covalently bound together. The sugar can be sialic acid or analogs thereof. The nucleotide can be any suitable nucleotide such as cytidine monophosphate (CMP).

"Sialic acid aldolase" refers to an aldolase that prepares sialic acid using pyruvate and N-acetyl mannose (ManNAc).

III. Glycosyltransferases

The present invention includes a variety of sialyltransferases with reduced sialidase and/or donor substrate hydrolysis activity. Sialyltransferases are one class of glycosyltransferases, enzymes that catalyze the transfer of a sugar from a nucleotide-sugar complex (donor substrate) to an acceptor, a mono, di or oligosaccharide. Sialyltransferases catalyze the transfer of N-acetylneuraminic acid, and analogs thereof, from a sialic acid-nucleotide complex, the donor substrate, to the terminal sugar of the acceptor which can be a monosaccharide, an oligosaccharide, a glycolipid, a glycopeptide, or a glycoprotein. Representative sialyltransferases include, but are not limited to, sialyltransferases in family EC 2.4.99, such as beta-galactosamide alpha-2,6-sialyltransferase (EC 2.4.99.1), alpha-N-acetylgalactosaminide alpha-2,6-sialyltransferase (EC 2.4.99.3), beta-galactoside alpha-2,3-sialyltransferase (EC 2.4.99.4), N-acetyllactosaminide alpha-2,3-sialyltransferase (EC 2.4.99.6), alpha-N-acetylneuraminide alpha-2,8-sialyltransferase (EC 2.4.99.8); lactosylceramide alpha-2,3-sialyltransferase (EC 2.4.99.9). The sialyltransferases of the present invention also include those of the CAZy GT80 family, or EC 2.4.99.4, drawn to alpha2-3 and alpha2-6 sialyltransferases, as well as sialyltransferases in the GT29, GT30, GT38, GT42, GT52, and GT73 families. Representative GT80 sialyltransferases include, but are not limited to, PmST1, Psp26ST, Vsp23ST, Pd26ST, PlST6 JT-1, PlST6 JT-2, Pp Pst3-1, Pp Pst3-2, Np23ST and Hd0053. (See Glycobiology 201, 21(6), 716; J. Mol. Biol. 2003, 328, 307; Annu. Rev. Biochem. 2008, 77, 521; Appl. Microbiol. Biotechnol. 2012, 94, 887 for review of sialyltransferases.)

The glycosyltransferases of the present invention include those having decreased $\alpha$2-3 sialidase or donor substrate hydrolysis activity compared to a control glycosyltransferase. $\alpha$2-3 sialidase activity refers to the back reaction starting from the product oligosaccharide, cleaving the glycosidic bond between the sugar from the donor substrate and the acceptor, resulting in the donor substrate and the acceptor.

In some embodiments, the glycosyltransferase can be an $\alpha$2-3-sialyltransferase. The $\alpha$2-3-sialyltransferases of the present invention can include sialyltransferases of *Pasteurella multocida*. In some embodiments, the glycosyltransferases of the present invention can have a motif in the sialyltransferase domain including at least one of sialyltransferase motif A (YDDGS (SEQ ID NO:31), corresponding to positions 139-143 of PmST1 wild type, SEQ ID NO: 13) and sialyltransferase motif B (KGH, corresponding to positions 309-311 of PmST1 wild type, SEQ ID NO: 13).

The glycosyltransferases of the present invention can include a polypeptide having any suitable percent identity to the control sequence. For example, the glycosyltransferases of the present invention can include a polypeptide having a percent sequence identity to the control glycosyltransferase sequence of at least 20, 30, 40, 50, 55, 60, 65, 70, 75, 80, 85, 90, 91, 92, 93, 94, 95, 96, 97, 98 or at least 99%. In some embodiments, percent sequence identity can be at least 80%. In some embodiments, percent sequence identity can be at least 90%. In some embodiments, percent sequence identity can be at least 95%. In some embodiments, the glycosyltransferase includes a polypeptide sequence having at least 80% sequence identity to SEQ ID NO:1.

In some embodiments, the isolated glycosyltransferase includes a polypeptide sequence of SEQ ID NO: 3 (M120D), SEQ ID NO: 5 (M120H), SEQ ID NO: 7 (E247F), SEQ ID NO: 9 (R289Y) or SEQ ID NO: 11 (E247F/R289Y).

The precise length of glycosyltransferases can vary, so the precise amino acid positions corresponding to each mutation can vary depending on the particular control glycosyltransferase used. Amino acid and nucleic acid sequence alignment programs are readily available (see, e.g., those referred to supra) and, given the particular motifs identified herein, serve to assist in the identification of the exact amino acids (and corresponding codons) for modification in accordance with the present invention. The positions of several mutations are shown in the table below for the PmST1 wild type sequence (SEQ ID NO: 13) and the $\Delta$24PmST1 (SEQ ID NO: 1) sequence.

| Mutation | PmST1 wild type (SEQ ID NO: 13) | $\Delta$24PmST1 (SEQ ID NO: 1) |
|---|---|---|
| 1 | M144D | M120D |
| 2 | M144H | M120H |
| 3 | E271F | E247F |
| 4 | R313Y | R289Y |
| 5 | E271F/R313Y | E247F/R289Y |

The above table illustrates "correspondence" of an amino acid position to a different sequence. For example, amino acid position 144 in the PmST1 wild type sequence (SEQ ID NO: 13) corresponds to position 120 of the $\Delta$24PmST1 sequence (SEQ ID NO: 1).

The control glycosyltransferases of the present invention includes any suitable glycosyltransferase or sialyltransferase. The glycosyltransferases of the present invention includes mutants corresponding to any position of PmST1 wild type sequence (SEQ ID NO: 13) and $\Delta$24PmST1 (SEQ ID NO: 1) (see *Biochemistry* 2006, 45(7), 2139, and 2007, 46(21), 6288). For example, the glycosyltransferases of the present invention include, but are not limited to, mutants at at least one of positions 120, 247 and 289 of $\Delta$24PmST1 (SEQ ID NO: 1). Other glycosyltransferases include mutants at at least one of positions 144, 271 and 313 of PmST1 wild type sequence (SEQ ID NO: 13). The mutants can include any suitable amino acid other than the native amino acid. For example, the amino acid can be V, I, L, M, F, W, P, S, T, A, G, C, Y, N, Q, D, E, K, R, or H. In some embodiments, the control glycosyltransferase can be the PmST1 wild type sequence (SEQ ID NO: 13) or the Δ24PmST1 (SEQ ID NO: 1). In some embodiments, the control glycosyltransferase can be Δ24PmST1 (SEQ ID NO: 1).

In some embodiments, the present invention provides an isolated glycosyltransferase, wherein the amino acid of the glycosyltransferase corresponding to position 120 of SEQ ID NO:1 is any amino acid other than M, the amino acid the glycosyltransferase corresponding to position 247 of SEQ ID NO:1 is any amino acid other than E, or the amino acid the glycosyltransferase corresponding to position 289 of SEQ ID NO:1 is any amino acid other than R. The glycosyltransferase of the present invention has decreased α2-3 sialidase or donor substrate hydrolysis activity compared to a control glycosyltransferase, wherein the amino acid of the control glycosyltransferase corresponding to position 120 of SEQ ID NO:1 is M, the amino acid of the control glycosyltransferase corresponding to position 247 of SEQ ID NO:1 is E, and the amino acid of the control glycosyltransferase corresponding to position 289 of SEQ ID NO:1 is R. Finally, the glycosyltransferase of the present invention can be a member of the glycosyltransferase family 80 (GT80).

In some embodiments, the isolated glycosyltransferase has decreased α2-3 sialidase activity, and includes at least one of the amino acid corresponding to position 247 of SEQ ID NO:1 is any amino acid other than E, and the amino acid corresponding to position 289 of SEQ ID NO:1 is any amino acid other than R. Decreased α2-3 sialidase activity can be measured by the ratio of α2-3 sialidase activity for the control glycosyltransferase to the α2-3 sialidase activity of the isolated glycosyltransferase. The ratio can be at least 2:1, 3:1, 4:1, 5:1, 10:1, 20:1, 30:1, 40:1, 50:1, 100:1, 200:1, 300:1, 400:1, 500:1 or at least 1000:1. In some embodiments, the ratio is at least 5:1. In some embodiments, the ratio is at least 10:1. In some embodiments, the ratio is at least 100:1. In some embodiments, the ratio is at least 1000:1.

In some embodiments, the isolated glycosyltransferase having decreased α2-3 sialidase activity includes the amino acid corresponding to position 247 of SEQ ID NO:1 is any amino acid other than E, and the amino acid corresponding to position 289 of SEQ ID NO:1 is any amino acid other than R.

In some embodiments, the isolated glycosyltransferase having decreased α2-3 sialidase activity includes the amino acid corresponding to position 117 of SEQ ID NO:1 is D or E. In some embodiments, the isolated glycosyltransferase having decreased α2-3 sialidase activity includes the amino acid corresponding to position 117 of SEQ ID NO:1 is A, G, V, L or 1. In some embodiments, the isolated glycosyltransferase having decreased α2-3 sialidase activity includes the amino acid corresponding to position 287 of SEQ ID NO:1 is H, K, R, W or F.

Other glycosyltransferases of the present invention have decreased donor substrate hydrolysis activity. Decreased donor substrate hydrolysis activity can be measured by the ratio of donor substrate hydrolysis activity for the control glycosyltransferase to the donor substrate hydrolysis activity of the isolated glycosyltransferase. The ratio can be at least 2:1, 3:1, 4:1, 5:1, 6:1, 7:1, 8:1, 9:1 or at least 10:1. In some embodiments, the isolated glycosyltransferase has decreased donor substrate hydrolysis activity, wherein the amino acid corresponding to position 120 of SEQ ID NO:1 is any amino acid other than M. In some embodiments, the ratio of donor substrate hydrolysis activity for the control α2-3 sialidase to the donor substrate hydrolysis activity of the isolated glycosyltransferase is at least 2:1.

In some embodiments, the amino acid corresponding to position 120 of SEQ ID NO:1 can be any amino acid of V, I, L, F, W, P, S, T, A, G, C, Y, N, Q, D, E, K, R, or H. In some embodiments, the amino acid corresponding to position 120 of SEQ ID NO:1 can be any amino acid of D, E, H, K or R. In some embodiments, the amino acid corresponding to position 120 of SEQ ID NO:1 can be any amino acid of D or H. In some embodiments, the amino acid corresponding to position 120 of SEQ ID NO:1 can be amino acid D. In some embodiments, the amino acid corresponding to position 120 of SEQ ID NO:1 can be amino acid H.

In some embodiments, the amino acid corresponding to position 247 of SEQ ID NO:1 can be any amino acid of V, I, L, M, F, W, P, S, T, A, G, C, Y, N, Q, D, K, R, or H. In some embodiments, the amino acid corresponding to position 247 of SEQ ID NO:1 can be any amino acid of F, Y or W. In some embodiments, the amino acid corresponding to position 247 of SEQ ID NO:1 can be amino acid F.

In some embodiments, the amino acid corresponding to position 289 of SEQ ID NO:1 can be any amino acid of V, I, L, M, F, W, P, S, T, A, G, C, Y, N, Q, D, E, K, and H. In some embodiments, the amino acid corresponding to position 289 of SEQ JD NO:1 can be any amino acid of Y, F or W. In some embodiments, the amino acid corresponding to position 289 of SEQ ID NO:1 can be amino acid Y.

The glycosyltransferases of the present invention can have one or more mutations. In some embodiments, the glycosyltransferase includes the amino acid corresponding to position 247 of SEQ ID NO:1 can be any amino acid of F, Y or W, and the amino acid corresponding to position 289 of SEQ ID NO:1 can be any amino acid of Y, F or W. In some embodiments, the amino acid corresponding to position 247 of SEQ ID NO:1 can be amino acid F, and the amino acid corresponding to position 289 of SEQ ID NO:1 can be amino acid Y.

In some embodiments, the isolated glycosyltransferase can be the amino acid corresponding to position 120 of SEQ ID NO:1 is D, E, H, K or R, the amino acid corresponding to position 247 of SEQ ID NO:1 is F, Y or W, or the amino acid corresponding to position 289 of SEQ ID NO:1 is Y, F or W. In some embodiments, the isolated glycosyltransferase can be the amino acid corresponding to position 120 of SEQ ID NO:1 is D or H, the amino acid corresponding to position 247 of SEQ ID NO:1 is F, or the amino acid corresponding to position 289 of SEQ ID NO:1 is Y.

The glycosyltransferases of the present invention can be constructed by mutating the DNA sequences that encode the corresponding unmodified glycosyltransferase (e.g., a wild-type glycosyltransferase or a corresponding variant from which the glycosyltransferase of the invention is derived), such as by using techniques commonly referred to as site-directed mutagenesis. Nucleic acid molecules encoding the unmodified form of the glycosyltransferase can be mutated by a variety of techniques well-known to one of ordinary skill in the art. (See, e.g., *PCR Strategies* (M. A. Innis, D. H. Gelfand, and J. J. Sninsky eds., 1995, Academic Press, San Diego, Calif.) at Chapter 14*; PCR Protocols: A Guide to Methods and Applications* (M. A. Innis, D. H. Gelfand, J. J. Sninsky, and T. J. White eds., Academic Press, NY, 1990).

By way of non-limiting example, the two primer system, utilized in the Transformer Site-Directed Mutagenesis kit from Clontech, may be employed for introducing site-directed mutants into a polynucleotide encoding an unmodified form of the glycosyltransferase. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids result in high mutation efficiency and allow minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis, such as for example, on a Mutation Detection Enhancement gel (Mallinckrodt Baker, Inc., Phillipsburg, N.J.) to confirm that no other alterations in the sequence have occurred (by band shift comparison to the unmutagenized control). Alternatively, the entire DNA region can be sequenced to confirm that no additional mutational events have occurred outside of the targeted region.

Verified mutant duplexes in pET (or other) overexpression vectors can be employed to transform *E. coli* such as, e.g., strain *E. coli* BL21 (DE3) pLysS, for high level production of the mutant protein, and purification by standard protocols. The method of FAB-MS mapping, for example, can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutated protein). The set of cleavage fragments is fractionated by, for example, microbore HPLC (reversed phase or ion exchange, again depending on the specific region to be modified) to provide several peptides in each fraction, and the molecular weights of the peptides are determined by standard methods, such as FAB-MS. The determined mass of each fragment are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS data agrees with prediction. If necessary to verify a changed residue, CAD-tandem MS/MS can be employed to sequence the peptides of the mixture in question, or the target peptide can be purified for subtractive Edman degradation or carboxypeptidase Y digestion depending on the location of the modification.

Recombinant Nucleic Acids

Mutant glycosyltransferases with at least one amino acid substituted can be generated in various ways. In the case of amino acids located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: DNA encoding the unmodified glycosyltransferase is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on. Alternatively, the multi-site mutagenesis method of Seyfang & Jin (*Anal. Biochem.* 324:285-291. 2004) may be utilized.

Accordingly, also provided are recombinant nucleic acids, optionally isolated, encoding any of the glycosyltransferases of the present invention (e.g., glycosyltransferases comprising any of SEQ ID NOs:4, 6, 8, 10 and 12). Using a nucleic acid of the present invention, encoding a glycosyltransferase of the invention, a variety of vectors can be made. Any vector containing replicon and control sequences that are derived from a species compatible with the host cell can be used in the practice of the invention. Generally, expression vectors include transcriptional and translational regulatory nucleic acid regions operably linked to the nucleic acid encoding the mutant glycosyltransferase. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. In addition, the vector may contain a Positive Retroregulatory Element (PRE) to enhance the half-life of the transcribed mRNA (see Gelfand et al. U.S. Pat. No. 4,666,848). The transcriptional and translational regulatory nucleic acid regions will generally be appropriate to the host cell used to express the glycosyltransferase. Numerous types of appropriate expression vectors, and suitable regulatory sequences are known in the art for a variety of host cells. In general, the transcriptional and translational regulatory sequences may include, e.g., promoter sequences, ribosomal binding sites, transcriptional start and stop sequences, translational start and stop sequences, and enhancer or activator sequences. In typical embodiments, the regulatory sequences include a promoter and transcriptional start and stop sequences. Vectors also typically include a polylinker region containing several restriction sites for insertion of foreign DNA. In certain embodiments, "fusion flags" are used to facilitate purification and, if desired, subsequent removal of tag/flag sequence, e.g., "His-Tag". However, these are generally unnecessary when purifying an thermoactive and/or thermostable protein from a mesophilic host (e.g., *E. coli*) where a "heat-step" may be employed. The construction of suitable vectors containing DNA encoding replication sequences, regulatory sequences, phenotypic selection genes, and the mutant glycosyltransferase of interest are prepared using standard recombinant DNA procedures. Isolated plasmids, viral vectors, and DNA fragments are cleaved, tailored, and ligated together in a specific order to generate the desired vectors, as is well-known in the art (see, e.g., Sambrook et al., *Molecular Cloning: A Laboratory Manual* (Cold Spring Harbor Laboratory Press, New York, N.Y., 2nd ed. 1989)). In some embodiments, the present invention provides a recombinant nucleic acid encoding an isolated glycosyltransferase of the present invention.

Host Cells

In certain embodiments, the expression vector contains a selectable marker gene to allow the selection of transformed host cells. Selection genes are well known in the art and will vary with the host cell used. Suitable selection genes can include, for example, genes coding for ampicillin and/or tetracycline resistance, which enables cells transformed with these vectors to grow in the presence of these antibiotics.

In one aspect of the present invention, a nucleic acid encoding a glycosyltransferase of the invention is introduced into a cell, either alone or in combination with a vector. By "introduced into" or grammatical equivalents herein is meant that the nucleic acids enter the cells in a manner suitable for subsequent integration, amplification, and/or expression of the nucleic acid. The method of introduction is largely dictated by the targeted cell type. Exemplary methods include CaPO$_4$ precipitation, liposome fusion, LIPOFECTIN®, electroporation, viral infection, and the like.

In some embodiments, prokaryotes are used as host cells for the initial cloning steps of the present invention. Other host cells include, but are not limited to, eukaryotic (e.g., mammalian, plant and insect cells), or prokaryotic (bacterial) cells. Exemplary host cells include, but are not limited to, *Escherichia coli, Saccharomyces cerevisiae, Pichia pastoris*, Sf9 insect cells, and CHO cells. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 94 (ATCC No. 31,446), *E. coli* strain W3110 (ATCC No. 27,325), *E. coli* K12 strain DG 116 (ATCC No. 53,606), *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various *Pseudomonas* species can all be used as hosts. Prokaryotic host cells or other host cells with rigid cell walls are typically transformed using the calcium chloride method as described in section 1.82 of Sambrook et al., supra. Alternatively, electroporation can be used for transformation of these cells. Prokaryote transformation techniques are set forth in, for example Dower, in *Genetic Engineering, Principles and Methods* 12:275-296 (Plenum Publishing Corp., 1990); Hanahan et al., *Meth. Enzymol.*, 204:63, 1991. Plasmids typically used for transformation of *E. coli* include pBR322, pUCI8, pUCI9, pUCI18, pUCI19, and Bluescript M13, all of which are described in sections 1.12-1.20 of Sambrook et al., supra. However, many other suitable vectors are available as well.

In some embodiments, the glycosyltransferases of the present invention are produced by culturing a host cell transformed with an expression vector containing a nucleic acid encoding the glycosyltransferase, under the appropriate conditions to induce or cause expression of the glycosyltransferase. Methods of culturing transformed host cells under conditions suitable for protein expression are well-known in the art (see, e.g., Sambrook et al., supra). Suitable host cells for production of the glycosyltransferases from lambda pL promoter-containing plasmid vectors include *E. coli* strain DG116 (ATCC No. 53606) (see U.S. Pat. No. 5,079,352 and Lawyer, F. C. et al., *PCR Methods and Applications* 2:275-87, 1993, which are both incorporated herein by reference). Following expression, the glycosyltransferase can be harvested and isolated. Methods for purifying the thermostable glycosyltransferase are described in, for example, Lawyer et al., supra. In some embodiments, the present invention provides a cell including a recombinant nucleic acid of the present invention. In some embodiments, the cell can be prokaryotes, eukaryotes, mammalian, plant, bacteria or insect cells.

IV. Methods of Making Oligosaccharides

Figure 5:
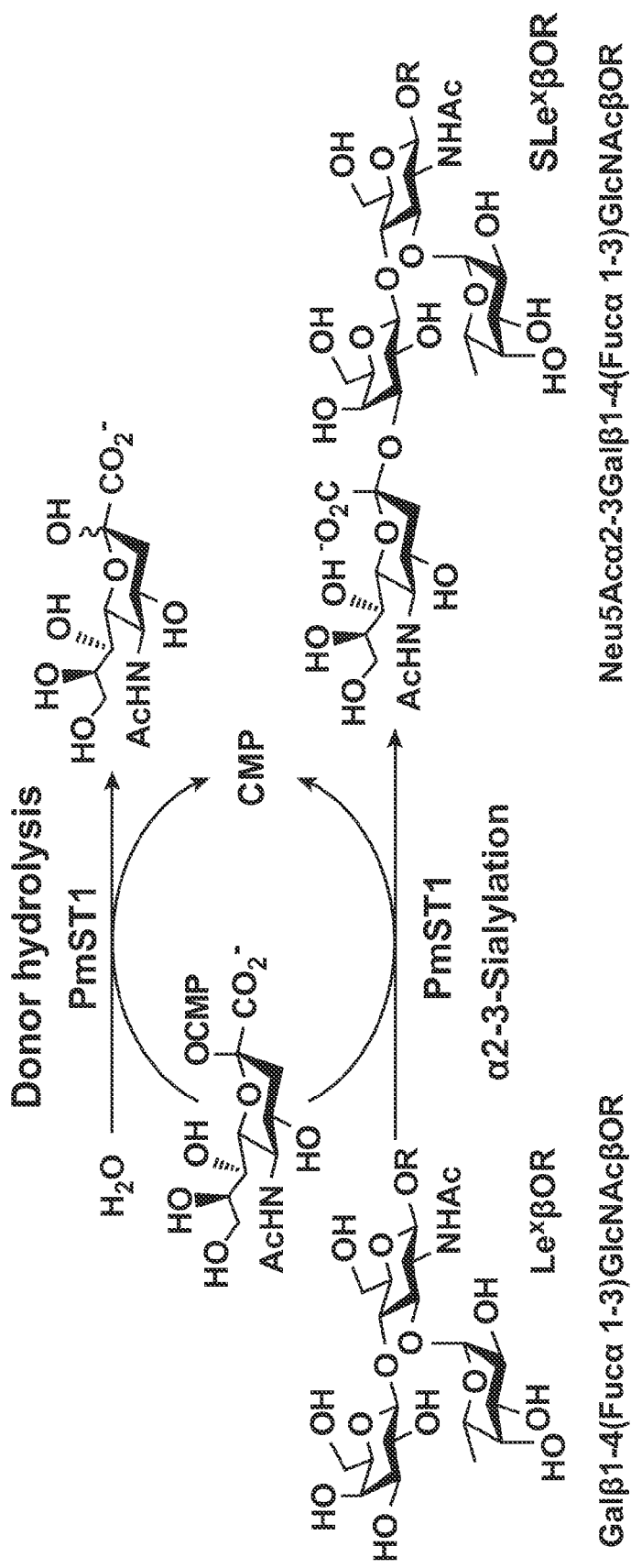

The glycosyltransferases of the present invention can be used to prepare oligosaccharides, specifically to add N-acetylneuraminic acid (Neu5Ac), other sialic acids, and analogs thereof, to a monosaccharide, an oligosaccharide, a glycolipid, a glycopeptide, or a glycoprotein. As shown in FIG. 5, the glycosyltransferase PmST1, catalyzes the addition of CMP-Neu5Ac to a fucosylated oligosaccharide by transferring the Neu5Ac to the oligosaccharide.

In some embodiments, the present invention provides a method of preparing an oligosaccharide, the method including forming a reaction mixture including an acceptor sugar, a donor substrate containing a sugar moiety and a nucleotide, and the glycosyltransferase of the present invention, under conditions sufficient to transfer the sugar moiety from the donor substrate to the acceptor sugar, thereby forming the oligosaccharide.

The acceptor sugar can be any suitable oligosaccharide, glycolipid, glycopeptide, or glycoprotein. When the acceptor sugar is an oligosaccharide, any suitable oligosaccharide can be used. For example, the acceptor sugar can be Galβ1-4GlcNAcβOR, wherein R can H, a sugar or an oligosaccharide. Alternatively, the acceptor sugar can be fucosylated, such as Galβ1-4(Fucα 1-3)GlcNAcβOR (Lewis$^x$βOR or Le$^x$-βOR) wherein R can H, a sugar or an oligosaccharide.

The donor substrate includes a nucleotide and sugar. Any nucleotide can be used, include, but are not limited to, adenine, guanine, cytosine, uracil and thymine nucleotides with one, two or three phosphate groups. In some embodiments, the nucleotide can be cytidine monophosphate (CMP). The sugar can be any suitable sugar. When the glycosyltransferase is a sialyltransferase, the sugar can be N-acetylneuraminic acid or Neu5Ac, other sialic acids and analogs thereof. Sialic acid is a general term for N- and O-substituted derivatives of neuraminic acid, and includes, but is not limited to, N-acetyl (Neu5Ac) or N-glycolyl (Neu5Gc) substitutions, as well as O-substitutions including acetyl, lactyl, methyl, sulfate and phosphate, among others. In some embodiments, the sialic acid can be a compound of the formula:

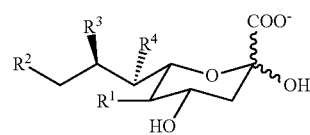

wherein R$^1$ can be H, OH, N$_3$, NHC(O)Me, NHC(O)CH$_2$OH, NHC(O)CH$_2$N$_3$, NHC(O)OCH$_2$C=CH$_2$, NHC(O)CH$_2$F, NHC(O)CH$_2$NHCbz, NHC(O)CH$_2$OC(O)Me, or NHC(O)

CH$_2$OBn; and R$^2$, R$^3$, and R$^4$ can be independently selected from H, OH, N$_3$, OMe, F, OSO$_3^-$, OPO$_3$H$^-$, or OC(O)Me. In some embodiments, the donor substrate can be CMP-Neu5Ac. Other donor substrates are useful in the methods of the present invention. In other embodiments, the sialic acid can be a compound of the formula:

$$R^2 \overset{OH}{\underset{R^1}{\diagdown}} \overset{OH}{\diagdown} \underset{HO}{\diagdown} \overset{COO^-}{\diagdown} OH.$$

Any glycosyltransferase of the present invention can be used in the methods of the present invention. In some embodiments, the glycosyltransferase can include a polypeptide sequence such as SEQ ID NO: 3 (M120D), SEQ ID NO: 5 (M120H), SEQ ID NO: 7 (E247F), SEQ ID NO: 9 (R289Y) or SEQ ID NO: 11 (E247F/R289Y). In some embodiments, the glycosyltransferase can include a polypeptide sequence such as SEQ ID NO: 3 (M120D) or SEQ ID NO: 5 (M120H). In some embodiments, the glycosyltransferase can include a polypeptide sequence such as SEQ ID NO: 7 (E247F), SEQ ID NO: 9 (R289Y) or SEQ ID NO: 11 (E247F/R289Y). The glycosyltransferases can be, for example, purified, secreted by a cell present in the reaction mixture, or can catalyze the reaction within a cell expressing the glycosyltransferase.

In another aspect of the present invention, reaction mixtures are provided comprising the glycosyltransferases as described herein. The reaction mixtures can further comprise reagents for use in glycosylation techniques. For example, in certain embodiments, the reaction mixtures comprise a buffer, salts (e.g., Mn$^{2+}$, Mg$^{2+}$), and labels (e.g., fluorophores).

The donor substrate can be prepared prior to preparation of the oligosaccharide, or prepared in situ immediately prior to preparation of the oligosaccharide. In some embodiments, the method of the present invention also includes forming a reaction mixture including a CMP-sialic acid synthetase, cytidine triphosphate, and N-acetylneuraminic acid (Neu5Ac) or a Neu5Ac analog, under conditions suitable to form the CMP-Neu5Ac or CMP-Neu5Ac analog. In some embodiments, the step of forming the donor substrate and the step of forming the oligosaccharide are performed in one pot.

In some embodiments, the sugar is prepared separately prior to use in the methods of the present invention. Alternatively, the sugar can be prepared in situ immediately prior to use in the methods of the present invention. In some embodiments, the method also includes forming a reaction mixture including a sialic acid aldolase, pyruvic acid or derivatives thereof, and N-acetylmannosamine or derivatives thereof, under conditions suitable to form the Neu5Ac or Neu5Ac analog. In some embodiments, the step of forming the sugar, the step of forming the donor substrate and the step of forming the oligosaccharide are performed in one pot.

The oligosaccharide prepared by the method of the present invention can be any suitable oligosaccharide, glycolipid or glycoprotein. For example, the oligosaccharide can be an α2-3-linked sialyloligosaccharide. In some embodiments, the oligosaccharide can be a fucosylated oligosaccharide. In some embodiments, the oligosaccharide can be Neu5Acα2-3Galβ1-4(Fucα 1-3)GlcNAcβOR (Sia-Lewis$^x$βOR or SLe$^x$-βOR) wherein R can be H, a monosaccharide, or an oligosaccharide. In some embodiments, the oligosaccharide can be Neu5Acα2-3Galβ1-4GlcNAcβOR, wherein R can H, a monosaccharide, or an oligosaccharide.

V. EXAMPLES

Example 1

Decreasing the Sialidase Activity of Multifunctional *Pasteurella multocida* Alpha2-3-Sialyltransferase 1 (PmST1) by Site-Directed Mutagenesis Methods Materials. *Escherichia coli* BL21 (DE3) was from Invitrogen (Carlsbad, Calif., USA). Ni$^{2+}$-NTA agarose (nickel-nitrilotriacetic acid agarose) and QIAprep spin miniprep kit were from Qiagen (Valencia, Calif., USA). Bicinchoninic acid (RCA) protein assay kit was from Pierce Biotechnology, Inc. (Rockford, Ill.). QuikChange Multi Site-Directed Mutagenesis Kit was from Agilent Technologies company/Stratagene (Santa Clara, Calif.).

Site-directed mutagenesis. Site-directed mutagenesis was carried out using the QuikChange multi-site-directed mutagenesis kit from Stratagene according to the manufacturer's protocol. The primers used were 5'-ACCGGCACGA-CAACTTGGTTTGGAAATACCGATGTGCG -3' (SEQ ID NO:32) for E271F and 5'-ATCTACTTTAAAGGGCATCCT-TATGGTGGTGAAATTAATGACTAC-3' (SEQ ID NO:33) for R313Y. The sites of mutations are underlined.

Protein Expression and Purification. The plasmids containing the mutant genes were transformed into *E. coli* BL21 (DE3). The *E. coli* cells were cultured in LB-rich media (10 g L$^{-1}$ tryptone, 5 g L$^{-1}$ yeast extract, and 10 g L$^{-1}$ NaCl) supplemented with ampicillin (100 µg mL$^{-1}$). Overexpression of the mutant proteins was achieved by adding 0.1 mM of isopropyl-1-thio-β-D-galactopyranoside (IPTG) to the *E. coli* culture when its OD$_{600\ nm}$ reached 0.8. The incubation of the induced culture was performed at 37° C. for 3 h with vigorous shaking at 250 rpm in a C25KC incubator shaker (New Brunswick Scientific, Edison, N.J.).

His$_6$ (SEQ ID NO:34) tagged mutant proteins were purified from the cell lysate. To obtain the cell lysate, the cell pellet harvested by centrifugation at 4000 rpm for 2 h was resuspended in 20 mL (for cells obtained from one liter culture) of lysis buffer (pH 8.0, 100 mM Tris-HCl containing 0.1% Triton X-100). To lyse the cells, lysozyme (50 µg mL$^{-1}$) and DNaseI (3 µg mL$^{-1}$) were then added to the resuspended cells followed by shaking at 37° C. for 60 min. The cell lysate was obtained as the supernatant after centrifugation at 11,000 rpm for 20 min. Purification of His$_6$ (SEQ ID NO:34) tagged proteins from the lysate was achieved using an ÄKTA FPLC system (GE Healthcare) equipped with a HisTrap™ FF 5 mL column. The column was pre-equilibrated with 8 column volumes of the binding buffer (5 mM imidazole, 0.5 M NaCl, 50 mM Tris-HCl pH 7.5) prior to lysate loading. After the sample loading, the column was washed with 8 column volumes of the binding and washing buffer (40 mM imidazole, 0.5 M NaCl, 50 mM Tris-HCl pH 7.5). Protein elution was carried out with 8 column volumes of the elute buffer (200 mM imidazole, 0.5 M NaCl, 50 mM Tris-HCl pH 7.5). The fractions containing the purified enzyme were collected and stored at 4° C.

Kinetic Assays. The kinetic assays for the sialidase activity were performed in duplicate in a total volume of 10 µL in MES buffer (100 mM, pH 5.5) containing different concentrations of Neu5Acα2-3LacβMU (0.4, 1.0, 2.0, 4.0, 10.0, 20.0, 40.0, and 60.0 mM) and the mutant proteins (2.5 mg mL$^{-1}$ of D141A, 1.6 mg mL$^{-1}$ of E271F, 1 mg mL$^{-1}$ of R313Y, and 3.2 mg mL$^{-1}$ of E271F/R313Y). All reactions were allowed to proceed at 37° C. for 60 min (D141A), 1 min (E271F), 25 min (R313Y), and 20 min (E271F/R313Y). The apparent kinetic parameters were obtained by fitting the experimental data (the average values of duplicate assay results) into the Michaelis-Menten equation using Grafit 5.0.

To obtain the apparent kinetic parameters of LacβMU as the acceptor for the α2-3-sialyltransferase activity, the kinetic assays were performed in duplicate in reaction mixtures of 10 μL containing Tris-HCl buffer (100 mM, pH 8.5), a fixed concentration of CMP-Neu5Ac (1 mM), different concentrations of LacβMU (0.2, 0.5, 1.0, 2.0, 5.0, and 9.0 mM) and the mutant proteins (2 μg mL$^{-1}$ of E271F, 2 μg mL$^{-1}$ of R313Y, and 1.6 μg mL$^{-1}$ of E271F/R313Y). All reactions were allowed to proceed at 37° C. for 5 min (E271F), 7 min (R313Y), and 10 min (E271F/R313Y). The apparent kinetic parameters were obtained by fitting the experimental data (the average values of duplicate assay results) into the Michaelis-Menten equation using Grafit 5.0.

To obtain the apparent kinetic parameters of CMP-Neu5Ac as the donor for the α2-3-sialyltransferase activity, the kinetic assays were performed in duplicate in reaction mixtures of 10 μL containing Tris-HCl buffer (100 mM, pH 8.5), a fixed concentration of LacβMU (1 mM), different concentrations of CMP-Neu5Ac (0.1, 0.2, 0.5, 1.0, 2.0, 5.0, 10.0 and 20.0 mM) and the mutant proteins (2 μg mL$^{-1}$ of E271F, 2 μg mL$^{-1}$ of R313Y, and 1.6 μg mL$^{-1}$ of E271F/R313Y). All reactions were allowed to proceed at 37° C. for 2 min (E271F), 7 min (R313Y), and 5 min (E271F/R313Y). The apparent kinetic parameters were obtained by fitting the experimental data (the average values of duplicate assay results) into the Michaelis-Menten equation using Grafit 5.0.

All the sialidase and α2-3-sialyltransferase assays were performed in an HPLC system. Reactions were stopped by adding 10 μL of ethanol. After necessary dilutions were performed to adjust the concentrations of the fluorescent-labeled compounds, the samples were then kept on ice until aliquots of 8 μL were injected and analyzed by a Shimadzu LC-6AD system equipped with a membrane on-line degasser, a temperature control unit, and a fluorescence detector (Shimadzu RF-10AXL). A reverse-phase Premier C18 column (250×4.6 mm i.d., 5 μm particle size, Shimadzu) protected with a C18 guard column cartridge was used. The mobile phase was 25% acetonitrile. The fluorescent compounds LacβMU and Neu5Acα2-3LacβMU were detected by excitation at 325 nm and emission at 372 nm.

Acceptor substrate specificity assays by HPLC. Assays were performed in duplicate in 20 mL of Tris-HCl buffer (100 mM, pH 8.5) containing CMP-Neu5Ac (1 mM), a fluorescent acceptor (1 mM), MgCl2 (20 mM), and an enzyme (2 □g mL-1, wild-type PmST1 or E271R/R313Y mutant). Reactions were allowed to proceed for 5 min at 37° C. The 4-methylumbelliferone (MU)-labeled fluorescent acceptors and the products formed were detected with excitation at 325 nm and emission at 372 nm. The 9-fluorenylmethylcarbamate (Fmoc)-labeled fluorescent acceptors and the products formed were detected with excitation at 262 nm and emission at 313 nm. The 2-aminobenzoic acid (2AA)-labeled fluorescent acceptors and the products formed were detected with excitation at 315 nm and emission at 400 nm.

Stability studies by HPLC. Thermal stability studies were carried out by incubating wild-type PmST1 or E271F/R313Y mutant solution (20 μg mL$^{-1}$) at 37° C. Samples were withdrawn at various time intervals for enzyme activity assays.

Results

Kinetics of the α2-3-sialidase Activity.

To test the involvement of D141 and H311 in the α2-3-sialidase activity of PmST1, the α2-3-sialidase activity of two previously obtained PmST1 mutants, D141A and H311A, were evaluated using a fluorescent α2-3-sialoside, Neu5Acα2-3LacβMU, as the substrate. The α2-3-sialidase activity of H311A mutant was too low to obtain the kinetic data. For the α2-3-sialidase activity of D141A mutant, the $K_m$ value (15±1 mM) was about the same as the wild-type PmST1 (24 mM), but its catalytic efficiency was about 7,300-fold lower than that of the wild-type PmST1 mainly due to a much slower turnover number of the D141A mutant (Table 1). These data indicated that both D141 and H311 are important for the α2-3-sialidase activity of PmST1.

TABLE 1

Apparent kinetic data for the α2-3-sialidase activity of wild-type PmST1 (WT) and PmST1 mutants.

| | $K_m$ (mM) | $k_{cat}$ (s$^{-1}$) | $k_{cat}/K_m$ (s$^{-1}$ mM$^{-1}$) |
|---|---|---|---|
| WT[4] | 24 | 2.3 × 10$^2$ | 9.5 |
| D141A | 15 ± 1 | (1.9 ± 0.1) × 10$^{-2}$ | 1.3 × 10$^{-3}$ |
| E271F | 5.7 ± 0.9 | 0.92 ± 0.04 | 0.16 |
| R313Y | 51 ± 5 | 0.18 ± 0.01 | 3.6 × 10$^{-3}$ |
| E271F/R313Y | (5.4 ± 0.6) × 10$^2$ | 0.83 ± 0.08 | 1.5 × 10$^{-3}$ |

Kinetics of the α2-3-sialidase activity of the mutants E271F, R313Y, and E271F/R313Y. The designed PmST1 mutants E271F, R313Y, and E271F/R313Y were expressed in E. coli using the same expression condition as the wild-type PmST1 (100 mg L$^{-1}$ culture) and achieved a compatible level of expression (90 mg L$^{-1}$ culture). Similar to the wild-type PmST1, one-step Ni$^{2+}$-column purification was sufficient to provide pure protein (>99%) of the mutants.

The kinetic assays for the α2-3-sialidase activity of the mutants E271F, R313Y, and E271F/R313Y using a fluorescent 4-methylumbelliferyl sialoside, Neu5Acα2-3LacβMU, as the substrate (Table 1) indicated that E271F mutation decreased the α2-3-sialidase activity of PmST1 about 59-fold which was mainly caused by a 250-fold decrease in the turnover number despite of a 4.2-fold decrease in the $K_m$ value. As expected, the R313Y mutation at a site close to the critical H311 residue for the α2-3-sialidase activity of PmST1 caused a 2,639-fold decrease in the catalytic efficiency ($k_{cat}/K_m$=0.0036 s$^{-1}$ mM$^{-1}$) compared to the wild-type PmST1 ($k_{cat}/K_m$=9.5 s$^{-1}$ mM$^{-1}$) mainly due to a (1,278-fold) decreased $k_{cat}$ value and a 2-fold increased $K_m$ value. The E271F/R313Y double mutant had the lowest α2-3-sialidase activity ($k_{cat}/K_m$=0.0015 s$^{-1}$ mM$^{-1}$) which was a 6,333-fold decrease compared to the wild-type PmST1 due to a 22.5-fold increase in the $K_m$ value and a 277-fold decrease in the $k_{cat}$ value.

Kinetics of the α2-3-sialyltransferase activity of the mutants E271F, R313Y, and E271F/R313Y. Kinetic assays (Table 2) for the α2-3-sialyltransferase activity of mutants E271F, R313Y, and E271F/R313Y using LacβMU as the fluorescent acceptor and CMP-Neu5Ac as the donor indicated that either E271F or R313Y mutation did not cause significant changes on either the $K_m$ or the $k_{cat}$ value, leading to quite consistent catalytic efficiencies ($k_{cat}/K_m$=28-39 s$^{-1}$ mM$^{-1}$) compared to the wild-type PmST1 ($k_{cat}/K_m$=34 s$^{-1}$ mM$^{-1}$).

TABLE 2

Apparent kinetic data for the α2-3-sialyltransferase activity of wild-type PmST1 (WT) and PmST1 mutants.

| Enzymes | CMP-Neu5Ac | | | LacβMU | | |
|---|---|---|---|---|---|---|
| | $K_m$ (mM) | $k_{cat}$ (s$^{-1}$) | $k_{cat}/K_m$ (s$^{-1}$ mM$^{-1}$) | $K_m$ (mM) | $k_{cat}$ (s$^{-1}$) | $k_{cat}/K_m$ (s$^{-1}$ mM$^{-1}$) |
| WT[4] | 0.44 | 32 | 73 | 1.4 | 47 | 34 |
| E271F | 0.18 ± 0.01 | 26 ± 1 | $1.4 \times 10^2$ | 0.71 ± 0.12 | 28 ± 1 | 39 |
| R313Y | 0.62 ± 0.04 | 19 ± 1 | 30 | 0.67 ± 0.05 | 19 ± 1 | 28 |
| E271F/R313Y | 0.34 ± 0.02 | 23 ± 1 | 69 | 0.54 ± 0.04 | 17 ± 1 | 32 |

Figure 2:
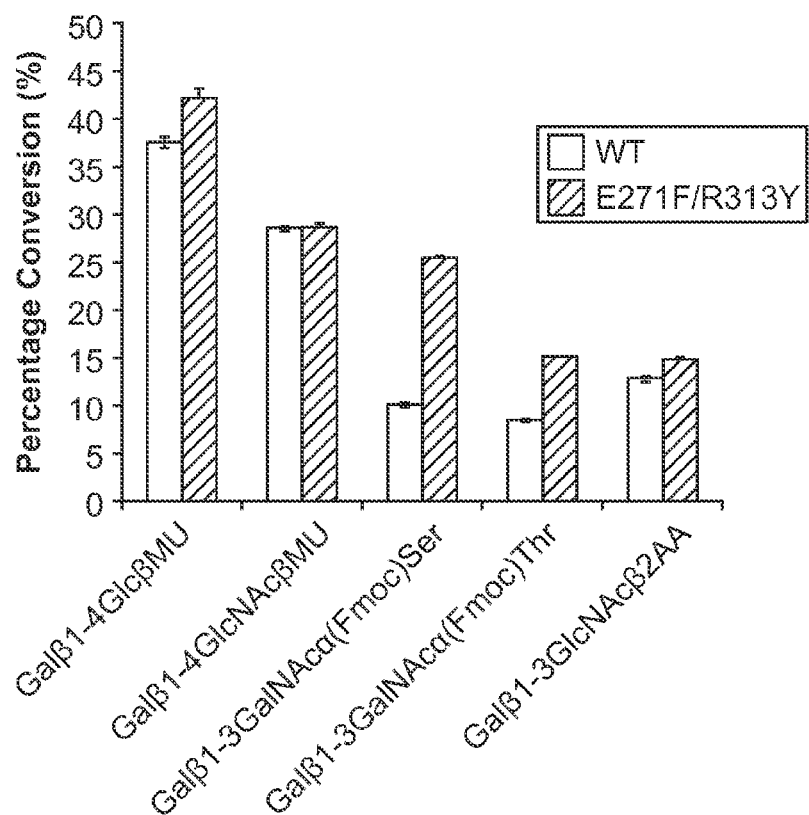
FIG. 2 shows acceptor substrate specificity data for the α2-3-sial pyrrolysine, can also be genetically coded for (Stadtman (1996) "Selenocysteine," *Annu Rev Biochem.* 65:83-100 and Ibba et al. (2002) "Genetic code: introducing pyrrolysine," *Curr Biol.* 12(13):R464-R466, which are both incorporated by reference). The term "amino acid" also includes unnatural amino acids, modified amino acids (e.g., having modified side chains and/or backbones), and amino acid analogs.

Acceptor substrate specificities of wild-type PmST1 and E271F/R313Y mutant. Fluorescent glycans with different glycosidic linkages and various monosaccharide units, including Galβ1-4Glcβ, Galβ1-4GlcNAcβ, Galβ1-3GalNAcα, and Galβ1-3GlcNAcβ structures, were used to investigate the acceptor substrate specificities of the wild-type PmST1 and E271F/R313Y mutant. As shown in FIG. 2, the E271F/R313Y mutant exhibited similar or slightly higher activity than the wild-type PmST1 towards different acceptors. Therefore, the acceptor promiscuity of PmST1 was not changed significantly by E271F and R313Y mutations.

Figure 3:
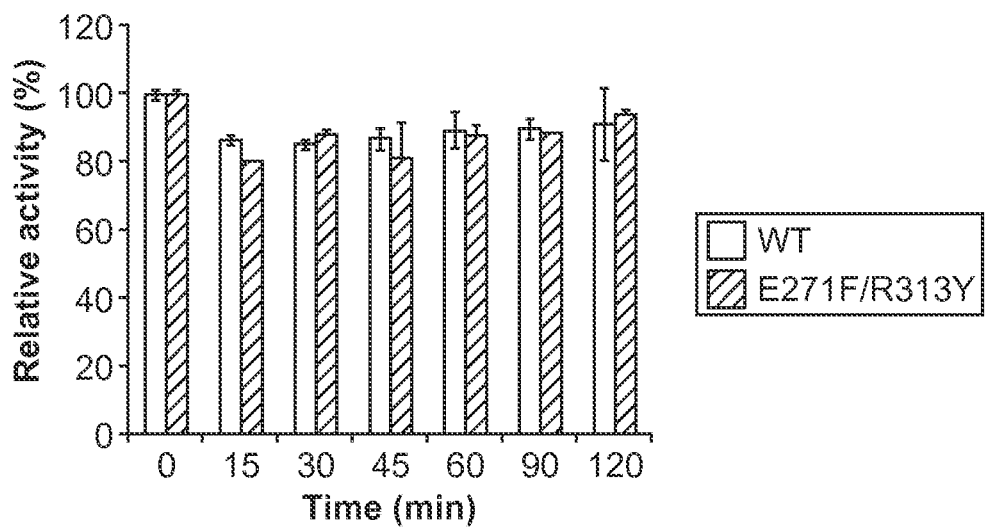

Thermal stabilities of wild-type PmST1 and E271F/R313Y mutant. Incubating the wild-type PmST1 and E271F/R313Y mutant at 37° C. for up to 2 hours did not decrease their activities significantly (FIG. 3). Therefore, both enzymes are considered quite stable and mutation does not affect the thermal stability of the PmST1.

Example 2

A Sialyltransferase Mutant with Decreased Donor Hydrolysis and Reduced Sialidase Activities for Directly Silylating Lewis$^x$ Methods Site-directed mutagenesis, expression and purification of PmST1 mutants. Site-directed mutagenesis was performed using the QuikChange multi-site-directed mutagenesis kit from Stratagene according to the manufacturer's protocol. The primers used were 5'-AATCTTTATGACGATGGCT-CAGATGAATATGTTGATTTAGAAAAAG-3' (SEQ ID NO:35) for M144D; 5'-AATCTTTATGACGATGGCTCA-CACaTGAATATGTTGATTTAGAAAAAG -3' (SEQ ID NO:36) for M144H; 5'-ATCACGCTGTATTTAGATCCT-GATTCCTTACCGGCATTAAATCAG-3' (SEQ ID NO:37) for A35D; and 5'-ATCACGCTGTATTTAGATCCTCATTC-CTTACCGGCATTAAATCAG-3' (SEQ ID NO:38) for A35H. The expression and purification of the mutants were performed as previously described for the WT PmST1 .

Kinetics of the donor hydrolysis activity of PmST1 and mutants by capillary electrophoresis analysis. The reactions were carried out in duplicate in a total volume of 10 μL at 37° C. for 15 min (WT), 40 min (D141A), 20 min (H311A), or 15 min (M144D and M144H) in Tris-HCl buffer (200 mM, pH 8.5) containing CMP-Neu5Ac (1, 2, 5, 10, 20 and 40 mM) and an enzyme (WT, 4 μg mL$^{-1}$; D141A, 1500 μg mL$^{-1}$; H311A, 40 μg mL$^{-1}$; M144D, 39 μg mL$^{-1}$; M144H, 5 μg mL$^{-1}$). The reactions were stopped by adding 10 μL of pre-chilled ethanol. The mixtures were incubated on ice for 30 min and centrifuged at 13,000 rpm for 5 min. The supernatants were diluted with borate buffer (25 mM, pH 9.5) and aliquots of 5 μL each were injected to a Beckman Coulter P/ACE™ MDQ Capillary Electrophoresis system equipped with a capillary (60 cm×75 μm i.d.) and monitored at 254 nm. The apparent kinetic parameters were obtained by fitting the experimental data (the average values of duplicate assay results) into the Michaelis-Menten equation using Grafit 5.0.

Kinetics of the α2-3-sialyltransferase activity of PmST1 mutants by HPLC analysis. With LacβMU as the acceptor substrate, the reactions were performed in duplicate at 37° C. for 10 min (M144D) or 4 min (M144H) in a reaction mixture (10 μL) containing Tris-HCl (100 mM, pH 8.5), an enzyme (5 μg mL$^{-1}$), and different concentrations (0.2, 0.5, 1.0, 2.0, and 5.0 mM) of LacβMU with a fixed concentration (1 mM) of CMP-Neu5Ac or different concentrations (0.2, 0.5, 1.0, 2.0, 5.0, and 10.0 mM) of CMP-Neu5Ac with a fixed concentration (1 mM) of LacβMU. With Le$^x$βMU as the acceptor substrate, the reactions were carried out in duplicate at 37° C. for 9 min (M144D) or 10 min (M144H) in a reaction mixture (10 μL) containing CAPSO (100 mM, pH 9.5), an enzyme (M144D, 39 μg mL$^{-1}$ or M144H, 5 μg mL$^-$), and various concentrations of Le$^x$βMU (1.0, 5.0, 10.0, 15.0, 25.0, and 35.0 mM) with a fixed concentration (1 mM) of CMP-Neu5Ac or various concentrations (0.2, 0.5, 1.0, 2.0, 5.0, 10.0, 20.0, and 40.0 mM) of CMP-Neu5Ac with a fixed concentration (1 mM) of Le$^x$βMU. Reactions were stopped by adding 10 μL of pre-chilled ethanol. The mixtures were incubated on ice for 30 min and centrifuged at 13,000 rpm for 5 min. The supernatants were diluted with 25% acetonitrile and kept on ice until aliquots of 8 μL were injected and analyzed by the Shimadzu LC-6AD system equipped with a membrane on-line degasser, a temperature control unit, and a fluorescence detector (Shimadzu RF-10AXL). A reverse-phase Premier C18 column (250×4.6 mm i.d., 5 μm particle size, Shimadzu) protected with a C18 guard column cartridge was used. The mobile phase was 25% acetonitrile. The fluorophore (MU)-labeled compounds were detected by excitation at 325 nm and emission at 372 nm. The apparent kinetic parameters were obtained by fitting the experimental data (the average values of duplicate assay results) into the Michaelis-Menten equation using Grafit 5.0.

Kinetics of the α2-3-sialidase activity of PmST1 mutants. The reactions were performed in duplicate in a total volume of 10 μL at 37° C. for 60 min (M144D) or 15 min (M144H) in MES buffer (100 mM, pH 5.5) containing Neu5Acα2-3LacβMU (0.4, 1, 2, 4, 10, 20, 40 and 60 mM) and an enzyme (M144H, 1.36 mg mL$^{-1}$ or M144D, 1.05 mg mL$^{-1}$). Sample treatment after the reaction and analysis were carried out by HPLC similar to that described above for the α2-3-sialyltransferase assays.

The α2-3-sialidase activity assays of PmST1 and mutants. The reactions were carried out in duplicate in a total volume of 10 μL at 37° C. for 20 hr in MES buffer (100 mM, pH 5.5) containing Neu5Acα2-3Le$^x$βMU (1 mM) and an enzyme (4 mg mL$^{-1}$). Aliquots of 1 μL were withdrawn at 1 hr, 6 hr and 20 hr, and analyzed by HPLC as described above for the α2-3-sialyltransferase assays.

Accession Codes. The structure of PmST1 M144D mutant in complex with CMP-3F(a)-Neu5Ac was deposited with a PDB ID code 3S44.

Materials and compound characterization. Chemicals were purchased and used without further purification. $^1$H NMR (600 MHz) and $^{13}$C NMR (150 MHz) spectra were recorded on a Varian VNMRS 600 MHz spectrometer or $^1$H NMR (800 MHz) and $^{13}$C NMR (200 MHz) on a Bruker 800 MHz spectrometer. High resolution electrospray ionization (ESI) mass spectra were obtained at the Mass Spectrometry Facility in the University of California, Davis. Silica gel 60 Å A was used for flash column chromatography. Thin-layer chromatography (TLC) was performed on silica gel plates using anisaldehyde sugar stain or 5% sulfuric acid in ethanol stain for detection. Gel filtration chromatography was performed with a column (100 cm×2.5 cm) packed with BioGel P-2 Fine resins. *Pasteurella multocida* sialic acid aldolase, 1 *N. meningitidis* CMP-sialic acid synthetase (NmCSS), 2 and wild-type PmST1 were expressed in *E. coli* and purified as described previously.

Crystallization and structure determination. PmST1 M144D mutant in Tris-HCl buffer (20 mM, pH 7.5) was concentrated to 13 mg mL$^{-1}$, and CMP-3F(axial)Neu5Ac was added to a final concentration of 2 mM. Binary CMP-3F (axial)Neu5Ac crystals were grown by hanging drop with 3 μL of the sample mixed with an equal volume of reservoir buffer [24% poly(ethylene glycol) 3350, 100 mM HEPES (pH 7.5), 50 mM NaCl, and 0.4% Triton X-100]. Then, the binary crystals were soaking with 10 mM of CMP-3F(axial)-Neu5Ac and 10 mM of Le$^x$βProN$_3$ in buffer containing 26% poly(ethylene glycol) 3350, HEPES (100 mM, pH 7.5), NaCl (100 mM), and 0.4% Triton X-100 for overnight. All crystals were transferred to Paratone-N and frozen in a steam of nitrogen to 100 K for data collection. Diffraction data were collected at the Stanford Synchrotron Radiation Lightsource to 1.45 Å resolution. Data were processed with XDS and scaled with XSCALE (Table 3). The structure was solved by Molecular Replacement using the program PHASER. Only the ligand-free open conformation structure (PDB ID: 2EX0) was successful in structure determination. The model was displayed and adjusted with COOT and refined with REFMAC. Final data processing and refinement statistics are shown in Table 3.

TABLE 3

X-Ray data collection and refinement statistics for PmST1 M144D.$^d$

| | |
|---|---|
| unit cell dimensions a, b, c (Å), β | 52.44, 61.57, 62.58, β = 114.15° |
| space group | P2$_1$ |
| no. of monomers per asymmetric unit | 1 |
| resolution range (Å) | 25.0-1.45 (1.49-1.45) |
| R$_{sym}$ [a] (%) | 3.8 (47.4) |
| <I>/σ<I> | 19.06 (2.58) |
| no. of reflections | 229,446 (16,432) |
| no. of unique reflections | 63,327 (4,962) |
| redundancy | 3.6 (3.3) |
| completeness (%) | 98.1 (98.2) |
| R$_{factor}$ [b] (%) | 18.7 |
| R$_{free}$ [c] (%) | 21.5 |
| no. of protein atoms | 3,197 |
| no. of CMP atoms | 21 |
| no. of water atoms | 431 |
| mean B-factor (Å$^2$) | |
| Protein, all atoms | 14.8 |
| Protein, main chain | 13.4 |
| Protein, side chain | 16.2 |
| CMP | 20.1 |
| water | 25.8 |

TABLE 3-continued

X-Ray data collection and refinement statistics for PmST1 M144D.$^d$

| | |
|---|---|
| rmsd from ideality | |
| bond distance (Å) | 0.0128 |
| bond angle (deg) | 1.429 |

[a] R$_{merge}$ = [Σ$_h$Σ$_i$|I$_h$ − I$_{hi}$|/Σ$_h$Σ$_i$I$_{hi}$] where I$_h$ is the mean of I$_{hi}$ observations of reflection h. Numbers in parenthesis represent highest resolution shell.
[b] R-Factor and
[c] R$_{free}$ = Σ||F$_{obs}$| − |F$_{calc}$||/Σ|F$_{obs}$| × 100 for 95% of recorded data (R-Factor) or 5% data (R$_{free}$)
$^d$Protein Data Bank Accession codes: The structure of PmST1 M144D mutant in complex with CMP-3F(a)-Neu5Ac was deposited with a PDB ID code 3S44.

NMR analysis of WT PmST1 and M144D mutant. Enzymes were expressed in *E. coli* BL21 (DE3) using M9 media containing $^{15}$NH$_4$Cl (1.0 g L$^{-1}$), Na$_2$HPO$_4$.7H$_2$O (12.66 g L$^{-1}$), KH$_2$PO$_4$ (3.0 g L$^{-1}$), NaCl (0.5 g L$^{-1}$), MgSO$_4$ (0.2 g L$^{-1}$), CaCl$_2$ (50 μM), and glucose (0.3%). Expressions were induced by adding 0.5 mM of isopropyl β-D-1-thiogalactopyranoside (IPTG) and incubating at 37° C. for 4 hr. The purifications were performed as previously described for the WT PmST1. The purified enzymes were dialyzed with a phosphate buffer (10 mM, pH 7.0). NMR samples of $^{15}$N-labeled WT and M144D PmST1 (~0.7 mM) were prepared in 90%/10% of H$_2$O/D$_2$O containing 10 mM of phosphate (pH 7.0) in the presence or the absence of saturating CMP. $^{15}$N—$^1$H HSQC NMR experiments were performed at 37° C. on Bruker Avance III 800 spectrometer with an Ultrashield Bruker magnet equipped with a four-channel interface, triple-resonance probe, and cryo-probe with Z-axis pulsed field gradients. The number of complex points and acquisition times were: 256, 180 ms ($^{15}$N (F$_1$)); and, 512, 64 ms ($^1$H (F$_2$)). The NMR spectra were processed and analyzed using the software, NMRPipe.

Example 3

Preparation of Oligosaccharides

One-pot three-enzyme synthesis of SLe$^x$βProN$_3$ with different sialic acid forms. Le$^x$βProN$_3$ (20-25 mg),$^9$ a sialic acid precursor (mannose, ManNAc, ManNGc or their derivatives, 1.5 equiv.), sodium pyruvate (5 equiv.), and CTP (1.5 equiv.) were dissolved in Tris-HCl buffer (10 mL, 100 mM, pH 7.5-8.5) containing MgCl$_2$ (20 mM) and appropriate amounts of Pm aldolase (0.5 mg), NmCSS (0.3-0.5 mg), and PmST1 mutant M144D (0.5-0.9 mg). The reactions were carried out by incubating the reaction mixture in an incubator shaker at 37° C. for 4-6 h. The product formation was monitored by TLC developed with EtOAc:MeOH:H$_2$O:HOAc=4:2:1:0.2 (by volume) and stained with p-anisaldehyde sugar stain. When an optimal yield was achieved, the reaction was stopped by adding the same volume (10 mL) of cold EtOH and incubation at 4° C. for 30 min. The mixture was then centrifuged and the precipitates were removed. The supernatant was concentrated, passed through a BioGel P-2 gel filtration column, and eluted with water to obtain partially purified product. A silica gel column was then used to obtain pure sialylated products with EtOAc:MeOH:H$_2$O=6:2:1 (by volume).

NMR chemical shifts and HRMS data of SLe$^x$βProN$_3$ containing different sialic acid forms synthesized by the one-pot three-enzyme system.

Neu5Acα2-3Le$^x$βProN$_3$ (1a). 33 mg, yield 93%. $^1$H NMR (600 MHz, D$_2$O): δ 5.09 (d, 1H, J=4.2 Hz), 4.50 (d, 1H, J=7.8 Hz), 4.07 (dd, 1H, J=10.4 and 3.2 Hz), 4.01-3.82 (m, 11H), 3.74 (d, 1H, J=4.2 Hz), 3.66-3.59 (m, 9H), 3.56-3.50 (m, 4H), 3.36-3.30 (m, 2H), 2.72 (dd, 1H, J=12.6 and 4.8 Hz), 2.01 (s, 3H), 2.00 (s, 3H), 1.87 (m, 2H), 1.75 (t, 1H, J=12.3 Hz), 1.12 (d, 3H, J=6.6). $^{13}$C NMR (150 MHz, D$_2$O): δ 175.20, 174.41, 174.05, 101.79, 101.15, 99.82, 98.76, 75.81, 75.42, 75.07, 74.98, 73.51, 73.07, 72.07, 72.03, 69.42, 69.35, 68.47, 68.28, 67.87, 67.47, 67.36, 66.84, 62.76, 61.64, 59.81, 55.98, 51.86, 47.93, 39.95, 28.27, 22.39, 22.20, 15.43. HRMS (ESI) m/z calcd for C$_{34}$H$_{57}$N$_5$O$_{23}$Na (M+Na) 926.3319. found 926.3342.

Neu5Gcα2-3Le$^x$βProN$_3$ (1b). 28 mg, yield 87%. $^1$H NMR (600 MHz, D$_2$O): δ 5.13 (d, 1H, J=4.2 Hz), 4.56-4.54 (m, 2H), 4.15 (s, 2H), 4.07 (dd, 1H, J=10.4 and 3.2 Hz), 4.01-3.82 (m, 12H), 3.78-3.60 (m, 8H), 3.56-3.54 (m, 3H), 3.52 (dd, 1H, J=10.4 and 7.8 Hz), 3.36-3.30 (m, 2H), 2.78 (dd, 1H, J=12.6 and 4.8 Hz), 2.06 (s, 3H), 1.87 (m, 2H), 1.75 (t, 1H, J=12.3 Hz), 1.19 (d, 3H, J=6.6). $^{13}$C NMR (150 MHz, D$_2$O): δ 175.73, 174.17, 173.84, 101.55, 100.91, 99.62, 98.52, 75.59, 75.20, 74.83, 74.75, 73.30, 72.57, 71.84, 69.20, 69.12, 69.10, 67.98, 67.65, 67.23, 67.13, 66.57, 66.61, 62.50, 60.91, 59.79, 59.60, 55.75, 51.33, 47.71, 39.78, 28.04, 22.16, 15.20. HRMS (ESI) m/z calcd for C$_{34}$H$_{57}$N$_5$O$_{24}$Na (M+Na) 942.3291. found 942.3292.

Kdnα2-3Le$^x$βProN$_3$ (1c). 27 mg, yield 85%. $^1$H NMR (600 MHz, D$_2$O): δ 5.04 (d, 1H, J=4.2 Hz), 4.47-4.45 (m, 2H), 3.85 (dd, 1H, J=9.6 and 2.4 Hz), 3.81-3.62 (m, 10H), 3.56 (d, 1H, J=4.0 Hz), 3.49-3.29 (m, 12H), 3.18-3.14 (m, 3H), 2.65 (dd, 1H, J=12.6 and 4.8 Hz), 1.98 (s, 3H), 1.87 (m, 2H), 1.69 (t, 1H, J=12.3 Hz), 1.10 (d, 3H, J=6.6). $^{13}$C NMR (150 MHz, D$_2$O): δ 174.36, 174.17, 101.72, 101.09, 99.76, 98.74, 75.70, 75.35, 75.02, 74.93, 74.04, 73.43, 72.26, 71.99, 70.32, 69.84, 69.34, 69.26, 67.79, 67.36, 67.28, 66.79, 62.73, 61.60, 59.73, 55.91, 47.84, 39.51, 28.21, 22.31, 15.37. HRMS (ESI) m/z calcd for C$_{32}$H$_{54}$N$_4$O$_{23}$Na (M+Na) 885.3077. found 885.3103.

Neu5AcN$_3$α2-3Le$^x$βProN$_3$ (1d). 33 mg, yield 89%. $^1$H NMR (800 MHz, D$_2$O): δ 5.06 (d, 1H, J=4.0 Hz), 4.47-4.56 (m, 2H), 4.01 (s, 2H), 3.96-3.76 (m, 11H), 3.72-3.59 (m, 10H), 3.54-3.45 (m, 3H), 3.47 (dd, 1H, J=10.4 and 7.8 Hz), 3.34-3.27 (m, 2H), 2.71 (dd, 1H, J=12.6 and 4.8 Hz), 1.98 (s, 3H), 1.81 (m, 2H), 1.74 (t, 1H, J=12.3 Hz), 1.10 (d, 3H, J=6.6). $^{13}$C NMR (200 MHz, D$_2$O): δ 174.43, 174.09, 171.36, 101.75, 101.17, 99.82, 98.81, 75.79, 75.40, 75.08, 74.99, 73.47, 72.74, 72.10, 72.06, 69.43, 69.33, 68.35, 68.19, 67.63, 67.44, 67.35, 66.86, 62.72, 61.67, 59.79, 55.98, m 52.06, 51.92, 47.91, 39.97, 28.28, 22.38, 15.44. HRMS (ESI) m/z calcd for C$_{34}$H$_{56}$N$_8$O$_{23}$Na (M+Na) 967.3356. found 967.3396.

KdnN$_3$α2-3Le$^x$βProN$_3$ (1e). 27 mg, yield 84%. $^1$H NMR (600 MHz, D$_2$O): δ 5.11 (d, 1H, J=4.0 Hz), 4.54 (d, 1H, J=8.0 Hz), 4.52 (d, 1H, J=8.0 Hz), 4.07 (dd, 1H, J=9.6 and 3.2 Hz), 4.03-3.83 (m, 11H), 3.78 (d, 1H, J=3.2 Hz), 3.72-3.66 (m, 6H), 3.60-3.49 (m, 5H), 3.38-3.35 (m, 3H), 2.75 (dd, 1H, J=12.6 and 4.8 Hz), 2.04 (s, 3H), 1.83 (m, 2H), 1.78 (t, 1H, J=12.3 Hz), 1.17 (d, 3H, J=6.6). $^{13}$C NMR (150 MHz, D$_2$O): δ 174.15, 173.64, 101.49, 100.88, 99.60, 98.52, 75.53, 75.16, 74.78, 74.73, 73.25, 72.77, 71.93, 71.80, 69.38, 69.16, 69.08, 68.30, 67.61, 67.10, 66.59, 62.50, 62.46, 61.38, 59.57, 55.73, 47.67, 39.50, 28.02, 22.13, 15.17. HRMS (ESI) m/z calcd for C$_{32}$H$_{53}$N$_7$O$_{22}$Na (M+Na) 910.3141. found 910.3137.

9-N$_3$-Neu5Acα2-3Le$^x$βProN$_3$ (1f). 28 mg, yield 91%. $^1$H NMR (800 MHz, D$_2$O): δ 5.11 (d, 1H, J=4.0 Hz), 4.56 (d, 1H, J=8.0 Hz), 4.51 (d, 1H, J=8.0 Hz), 4.03-4.02 (m, 2H), 3.98-3.85 (m, 9H), 3.79 (d, 1H, J=3.2 Hz), 3.71-3.69 (m, 8H), 3.61-3.49 (m, 6H), 3.40-3.36 (m, 3H), 2.77 (dd, 1H, J=12.6 and 4.8 Hz), 2.05 (s, 3H), 1.83 (m, 2H), 1.79 (t, 11-1, J=12.3 Hz), 1.17 (d, 3H, J=6.6). $^{13}$C NMR (200 MHz, D$_2$O): δ 174.90, 174.16, 173.74, 101.51, 100.88, 99.58, 98.50, 75.63, 75.21, 74.81, 74.73, 73.24, 72.64, 72.42, 71.81, 70.39, 69.19, 69.09, 68.70, 68.20, 67.61, 67.15, 67.11, 66.59, 61.38, 59.60, 55.72, 53.01, 51.59, 47.68, 39.77, 28.02, 22.14, 15.18. HRMS (ESI) m/z calcd for C$_{34}$H$_{56}$N$_8$O$_{22}$Na (M+Na) 951.3407. found 910.3407.

9-O-Ac-Neu5Acα2-3Le$^x$βProN$_3$ (1g). 20 mg, yield 62%. $^1$H NMR (600 MHz, D$_2$O): δ 5.12 (d, 1H, 1=4.0 Hz), 4.55-4.53 (m, 2H), 4.44 (dd, 1H, J=11.4 and 1.8 Hz), 4.20 (dd, 1H, J=11.4 and 6.6 Hz), 4.14-3.86 (m, 11H), 3.79 (d, 1H, J=3.0 Hz), 3.74-3.65 (m, 8H), 3.58-3.56 (m, 2H), 3.54 (dd, 1H, 1=9.6 and 7.8 Hz), 3.41-3.36 (m, 2H), 2.78 (dd, 1H, J=12.6 and 4.8 Hz), 2.16 (s, 3H), 2.05 (s, 6H), 1.85 (m, 2H), 1.81 (t, 1H, J=12.6 Hz), 1.18 (d, 3H, 1=6.6). $^{13}$C NMR (150 MHz, D$_2$O): δ 174.18, 174.41, 174.00, 173.96, 101.80, 101.14, 99.80, 98.78, 75.88, 75.53, 75.09, 74.80, 73.54, 72.89, 72.08, 69.75, 69.57, 69.45, 69.37, 68.46, 68.37, 67.89, 67.37, 66.86, 65.98, 61.65, 59.84, 55.99, 51.85, 47.60, 40.05, 28.29, 22.41, 22.23, 20.44, 15.45. HRMS (ESI) m/z calcd for C$_{36}$H$_{59}$N$_5$O$_{24}$Na (M+Na) 968.3448. found 968.3427.

9-O-Ac-Ncu5Gcα2-3Le$^x$βProN$_3$ (1h). 21 mg, yield 64%. $^1$H NMR (600 MHz, D$_2$O): δ 5.12 (d, 1H, J=4.0 Hz), 4.55 (dd, 1H, J=7.8 and 4.2 Hz), 4.45 (m, 1H), 4.22-4.19 (m, 1H), 4.14 (s, 2H), 4.13-3.79 (m, 13H), 3.73-3.66 (m, 8H), 3.61-3.59 (m, 2H), 3.55 (t, 1H, J=7.8 Hz), 3.41-3.37 (m, 2H), 2.80 (dd, 1H, J=12.6 and 4.8 Hz), 2.16 (s, 3H), 2.06 (s, 6H), 1.88-1.85 (m, 2H), 1.81 (t, 1H, J=12.6 Hz), 1.19 (d, 3H, 1=6.6). $^{13}$C NMR (150 MHz, D$_2$O): δ 175.93, 174.54, 174.41, 174.01, 101.80, 101.15, 99.81, 99.77, 75.86, 75.53, 75.09, 75.00, 73.54, 72.62, 72.09, 69.75, 69.63, 69.45, 69.37, 68.30, 68.23, 67.90, 67.36, 66.86, 65.93, 61.65, 61.17, 59.83, 55.99, 51.54, 47.95, 40.10, 28.29, 22.41, 20.44, 15.45. HRMS (ESI) m/z calcd for C$_{36}$H$_{59}$N$_5$O$_{24}$Na (M+Na) 984.3397. found 984.3397.

Results and Discussion

Figure 4:
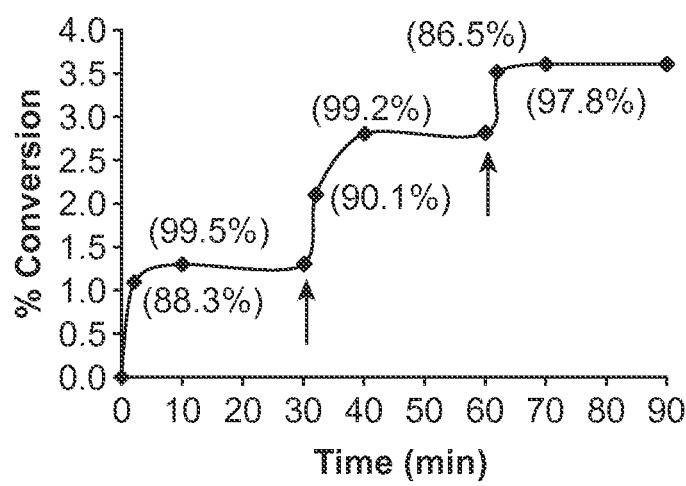

Donor hydrolysis by PmST1 causes low yield sialylation of Le$^x$. In order to understand why PmST1-catalyzed sialylation of Le$^x$ resulted in low yields, time course studies were carried out using a fluorescently labeled Le$^x$ acceptor (4-methylumbelliferyl β-Le$^x$ or Le$^x$βMU) in a high performance liquid chromatography (HPLC) assay. As shown in FIG. 4, PmST1-catalyzed sialylation of Le$^x$βMU (1 mM) using one equivalent of donor CMP-Neu5Ac reached a low yield (1.1-1.3%) plateau quickly within 2 min. Every additional dose of donor substrate CMP-Neu5Ac (shown by arrows in FIG. 4) increased the product formation which always reached a plateau quickly. Monitoring the CMP-Neu5Ac consumption (% consumption numbers are shown in parentheses in FIG. 4) in the reaction mixture by capillary electrophoresis studies confirmed a quick consumption of CMP-Neu5Ac. These indicated that donor (CMP-Neu5Ac) hydrolysis activity of PmST1, where water molecules compete with the poor Le$^x$ acceptor for the consumption of sugar nucleotide (CMP-Neu5Ac) donor of the sialyltransferase (FIG. 5), contributed significantly to the low yield of PmST1-catalyzed sialylation. In fact, donor hydrolysis has been observed in other glycosyltransferase-catalyzed reactions that lead to lower synthetic yields. The donor hydrolysis were observed frequently in co-crystallization of glycosyltransferases with a corresponding sugar nucleotide donor where its sugar component was usually cleaved off and only the hydrolyzed nucleotide was observed in the substrate binding pocket of the enzyme. Therefore, inert donor derivatives of glycosyltransferases have been commonly applied in the x-ray crystal structure studies of glycosyltransferases. Two recent papers discussed the donor hydrolysis activities of human blood group A and B glycosyltransferases (GTA and GTB) which are Mn$^{2+}$-dependent and the UDP-Gal hydrolysis activity of GTB is increased in the presence of an acceptor substrate analog. Nevertheless, the effect of donor hydrolysis of glycosyltransferases on glycosylation processes has not been investigated in detail. In addition, no strategy has been reported for improving the yields of glycosyltransferase-catalyzed reactions by decreasing donor hydrolysis activity.

Asp141 and His311 influence PmST1 donor hydrolysis activity. As shown in Table 4, D141A mutation decreased the efficiency of CMP-Neu5Ac hydrolysis activity of PmST1 by 1,000-fold mainly due to the decrease in the turnover number. H311A mutation also decreased the CMP-Neu5Ac hydrolysis activity by 16-fold, mainly contributed by a decreased turnover number without affecting the binding affinity significantly.

TABLE 4

Apparent kinetics of the CMP-Neu5Ac hydrolysis activity of WT PmST1 and mutants.

| | $K_m$ (mM) | $k_{cat}$ (s$^{-1}$) | $k_{cat}/K_m$ (s$^{-1}$ mM$^{-1}$) |
|---|---|---|---|
| WT | 1.5 ± 0.2 | 27 ± 1 | 18 |
| [a]D141A | 1.4 ± 0.2 | (2.5 ± 0.1) × 10$^{-2}$ | 1.8 × 10$^{-2}$ |
| [a]H311A | 1.8 ± 0.2 | 2.1 ± 0.1 | 1.1 |
| M144D | 7.3 ± 0.5 | 6.5 ± 0.1 | 0.89 |
| M144H | 13 ± 3 | 71 ± 6 | 5.5 |

[a]PmST1 D141A and H311A mutants were generated previously. See, Ni, et al. (2006) *Biochemistry* 45, 2139-2148.

PmST1 mutants with decreased CMP-Neu5Ac hydrolysis activity. As shown in Table 4, both M144D and M144H mutations decreased the efficiency of donor hydrolysis. M144D mutation decreased the efficiency of donor hydrolysis by 20-fold due to a 4.9-fold increase of the $K_m$ value and a 4.2-fold decrease of the $k_{cat}$ value. M144H mutation caused a less significant 3.3-fold decrease in the efficiency of donor hydrolysis due to a significant 8.7-fold increase in the $K_m$ value which is offset by a 2.6-fold increase in the $k_{cat}$ value.

α2-3-sialyltransferase activities of PmST1 mutants. As shown in Table 5, when a good sialyltransferase acceptor 4-methylumbelliferyl β-lactoside (LacβMU) was used, the M144D mutation decreased the α2-3-sialyltransferase activity by 18-fold due to a 9-fold increase of $K_m$ value and a 2-fold decrease of $k_{cat}$ value. When a poor sialyltransferase acceptor Le$^x$βMU was used, the M144D mutation did not change the efficiency of the α2-3-sialyltransferase activity of PmST1 significantly. In comparison, M144H mutation only decreased the α2-3-sialyltransferase activity weakly (1.3-fold) when LacβMU was used as an acceptor and increased the efficiency of α2-3-sialyltransferase activity by 2.6-fold when Le$^x$βMU was used as an acceptor.

α2-3-sialidase activity of PmST1 by 5588- and 594-fold respectively when Neu5Acα2-3LacβMU was used as the sialidase substrate (Table 6). While the PmST1 M144D mutant showed no sialidase activity when Neu5Acα2-3Le$^x$-βMU was used as the substrate, PmST1 M144H has increased sialidase activity compared to the WT PmST1 using the SLe$^x$ substrate. For example, the PmST1 M144H mutant cleaved 10.0%, 24.5%, and 34.0% of Neu5Ac from Neu5Acα2-3Le$^x$-βMU in 1 h, 6 h, and 20 h, respectively. In comparison, WT PmST1 removed 2.0%, 7.0%, and 7.5% of Neu5Ac from Neu5Acα2-3Le$^x$βMU under the same reaction conditions. The decreased α2-3-sialidase activity by M144D mutation allows the potential application of the PmST1 M144D mutant in sialylation of glycoconjugates containing terminal galactoside or Le$^x$ where the decreased α2-3-sialidase activity has the most advantages as these reactions are challenging for prompt monitoring.

TABLE 6

Apparent kinetics of the α2-3-sialidase activity of WT PmST1, M144D, and M144H mutants using Neu5Acα2-3LacβMU as the sialidase substrate.

| | $K_m$ (mM) | $k_{cat}$ (s$^{-1}$) | $k_{cat}/K_m$ (s$^{-1}$ mM$^{-1}$) |
|---|---|---|---|
| [a]WT | [a]24 | [a]2.3 × 10$^2$ | [a]9.5 |
| M144D | 20 ± 2 | (3.5 ± 0.1) × 10$^{-2}$ | 1.7 × 10$^{-3}$ |
| M144H | 1.7 ± 0.3 | (2.7 ± 0.2) × 10$^{-2}$ | 1.6 × 10$^{-2}$ |

[a]Data are from Yu, H., et al. (2005) *J. Am. Chem. Soc.* 127, 17618-17619.

Figure 6:
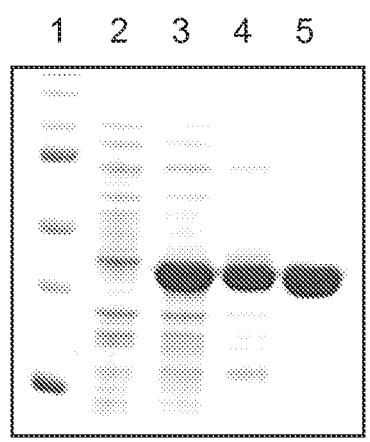

PmST1 M144D mutant has a similar expression level as the WT PmST1. The PmST1 M144D mutation did not change the enzyme expression level in *E. coli*. About 98 mg of C-His$_6$-tagged PmST1 M144D protein can be routinely purified from one liter of *E. coli* cell culture using Ni$^{2+}$-affinity column (FIG. 6). This expression level is very similar to that (100 mg) of the WT PmST1 and allows the application of the mutant in preparative and large-scale synthesis of SLe$^x$ antigens.

Figure 7:
Figure 7:
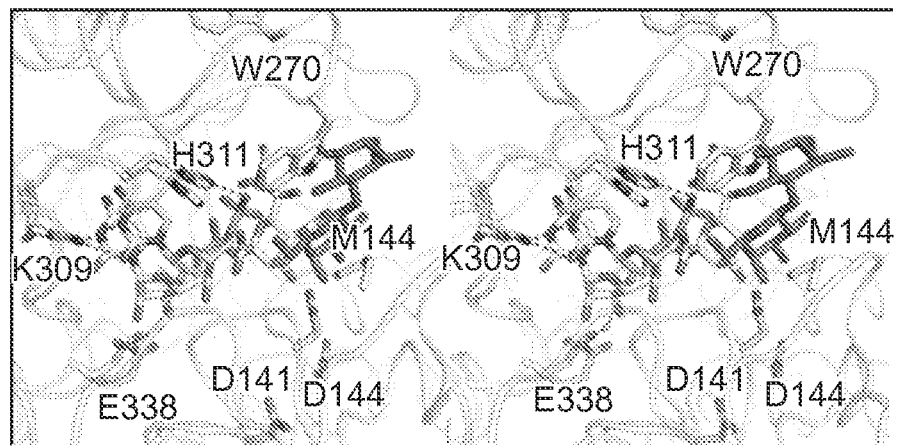
Figure 7:
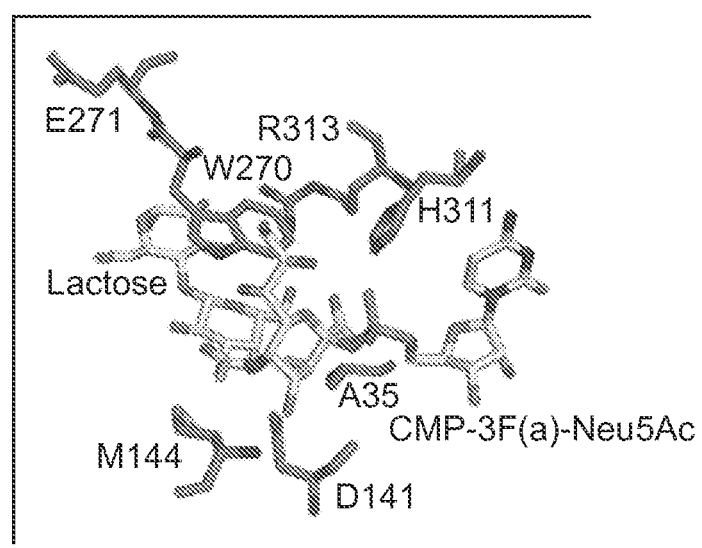
Figure 8:
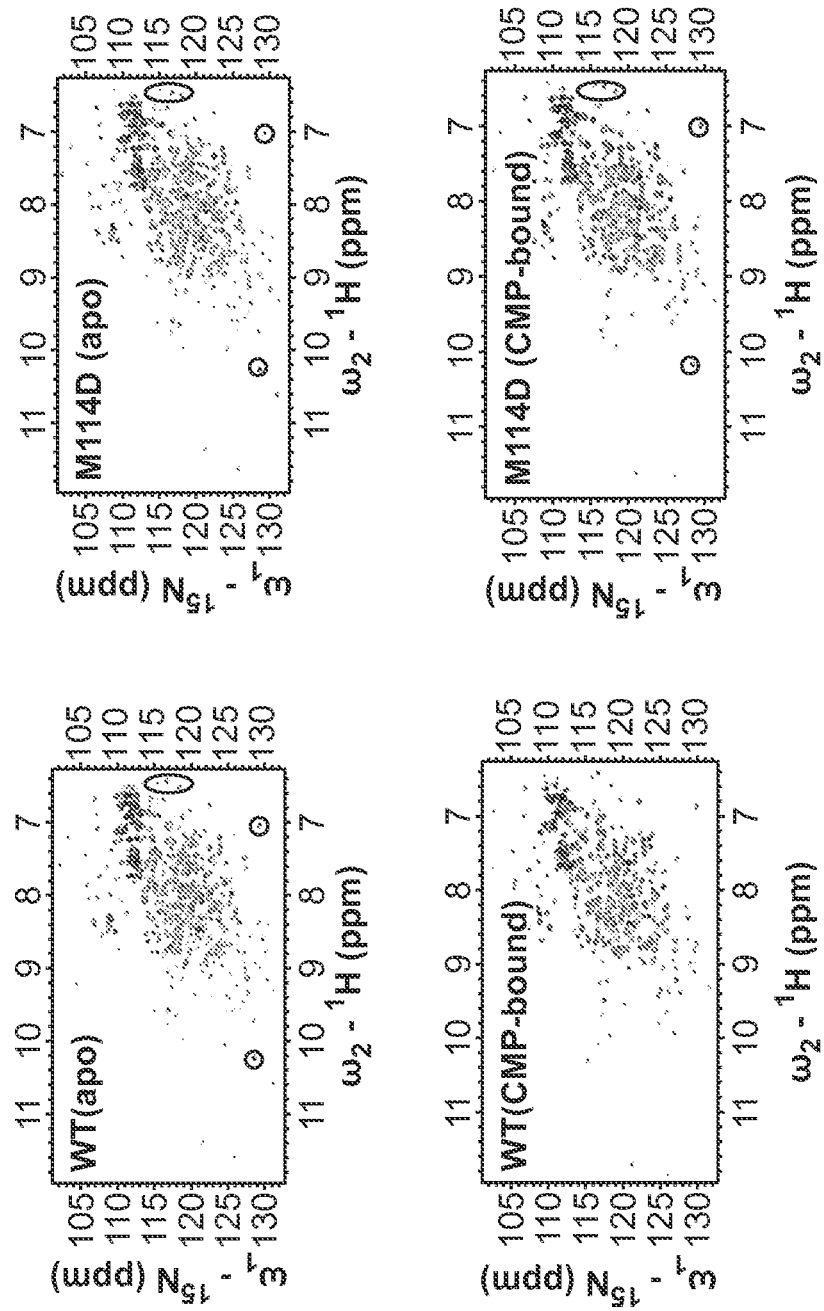

X-Ray crystal structure of PmST1 M144D mutant. The structure of the PmST1 M144D mutant with CMP-3F(axial)-Neu5Ac was determined to 1.45 Å resolution with $R_{factor}$ and $R_{free}$ values of 18.7% and 21.5% respectively Table 3). FIG. 7 shows the structural comparison between WT PmST1 and M144D mutant with bound CMP donor. FIG. 7A shows the overall structure of WT PmST1 with CMP bound (white tubes), aligned with the C-terminal domain of the M144D mutant (grey tubes) also with CMP bound (space filled atoms). FIG. 7B shows the stereo view of the superposition near the active site. WT PmST1 is shown as white tubes with

TABLE 5

Apparent kinetics of the α2-3-sialyltransferase activity of WT PmST1 and mutants.

| | $K_m$ (mM) | | | $k_{cat}$ (s$^{-1}$) | | | $k_{cat}/K_m$ (s$^{-1}$ mM$^{-1}$) | | |
|---|---|---|---|---|---|---|---|---|---|
| | WT | M144D | M144H | WT | M144D | M144H | WT | M144D | M144H |
| LacβMU | [a]1.4 | 12 ± 1 | 0.79 ± 0.04 | [a]47 | 22 ± 1 | 21 ± 1 | [a]34 | 1.9 | 27 |
| [b]CMP-Neu5Ac | [a]0.44 | 0.30 ± 0.05 | 0.81 ± 0.06 | [a]32 | 1.9 ± 0.1 | 21 ± 1 | [a]73 | 6.1 | 27 |
| Le$^x$βMU | 17 ± 2 | 13 ± 2 | 8.1 ± 0.9 | 6.7 ± 0.3 | 4.0 ± 0.2 | 8.4 ± 0.3 | 0.38 | 0.32 | 1.0 |
| [c]CMP-Neu5Ac | 0.39 ± 0.03 | 2.1 ± 0.1 | 0.4 ± 0.05 | 0.55 ± 0.01 | 0.59 ± 0.01 | 0.93 ± 0.02 | 1.4 | 0.28 | 2.2 |

[a]Data are from Yu, H., et al. (2005) *J. Am. Chem. Soc.* 127, 17618-17619.
[b]With LacβMU,
[c]With Le$^x$βMU.

PmST1 M144D mutant has a decreased α2-3-sialidase activity. M144D and M144H mutations also decreased the bound CMP-3F(a)-Neu5Ac (sticks with white carbon bonds) and lactose acceptor (sticks with dark grey carbon bonds).

The M144D mutant in shown as grey tubes with CMP bound (sticks with light grey carbon bonds). FIG. 7C shows the active site of the ternary crystal structure of PmST1 (PDB ID: 21HZ) with bound CMP-3F(axial)-Neu5Ac and lactose. The mutation site M144 is underlined.

The structure resides in the open conformation similar to the wild-type structure with no substrate (rmsd of 0.50 Å for 385 equivalent α-carbons). However, the M144D structure contains well-ordered electron density in the active site that clearly defines the CMP nucleotide. The sialic acid moiety is disordered, likely due to dynamics and/or multiple conformations in the open state of the enzyme. In the M144D structure, the CMP moiety does not bind as deeply into the pocket of the active site as the WT PmST1. The base and ribose are situated about 1.5 and 2.0 Å respectively, farther out of the active site compared to the WT PmST1. In the wild-type structure, Glu338 forms bidentate hydrogen bond interactions with both the 2' and 3' OH of the CMP ribose. In the M144D structure, an ordered water molecule mediates the interaction between the ribose and Glu338. The more shallow binding of the donor nucleotide in the M144D structure does not pull down the β-strand and the ensuing loop that contains Trp270. In comparison, in the wild-type enzyme, donor-nucleotide binding pulls down a β-strand causing Trp270 to pop out of the C-terminal domain, where it helps define the acceptor binding site in the sialyltransferase reaction.

PmST1 M144D mutant is more efficient than M144H mutant in silylating $Le^x$. Overall, the M144D mutation decreased the undesired CMP-Neu5Ac hydrolysis activity significantly (20-fold) without appreciably changing the efficiency of the α2-3-sialyltransferase activity when $Le^x$ was used as an acceptor. As a result, M144D showed an overall improved activity in sialylation of $Le^x$ for the formation of sialyl $Le^x$ ($SLe^x$) structures. In comparison, M144H mutant which has a 3.3-fold decreased CMP-Neu5Ac hydrolysis activity and 2.6-fold increased α2-3-sialyltransferase activity using $Le^x$ as an acceptor was less effective for directly silylating $Le^x$.

Figure 9:
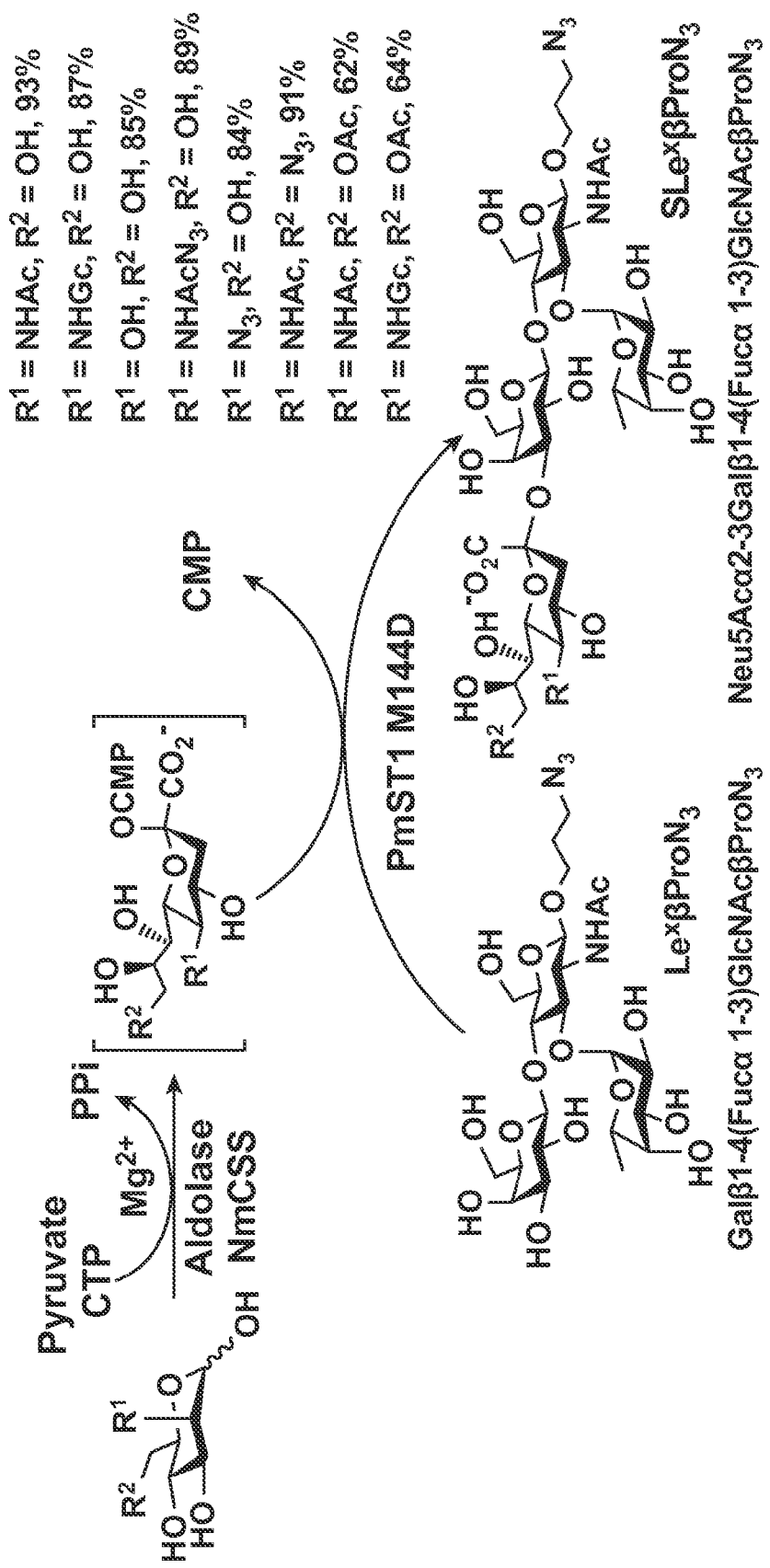
Figure 10:
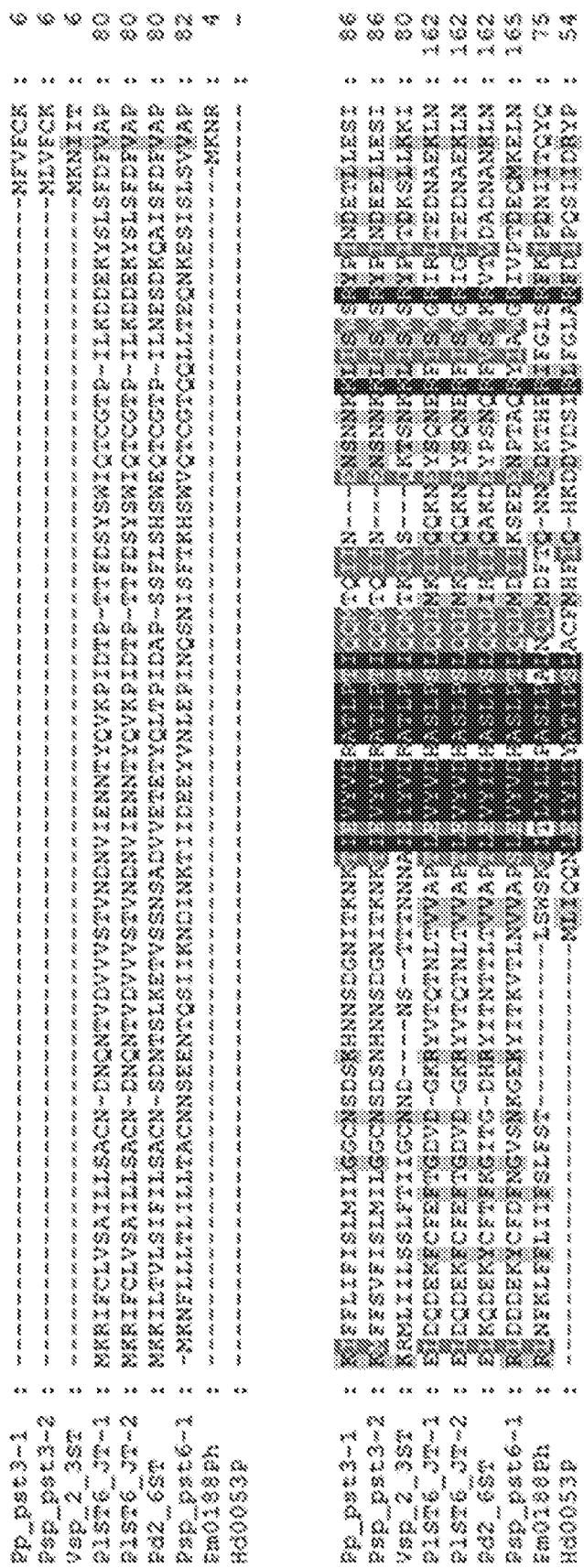

Synthesis of $SLe^x$ containing diverse sialic acid forms using PmST1 M144D mutant. The application of the PmST1 M144D mutant obtained by protein structure-based rational design in the synthesis of $SLe^x$ containing diverse naturally occurring and non-natural sialic acid forms was demonstrated using an efficient one-pot three-enzyme chemoenzymatic synthetic system (FIG. 9). The system contained PmST1 M144D mutant, an *Neisseria meningitidis* CMP-sialic acid synthetase (NmCSS), and a *Pasteurella multocida* sialic acid aldolase. N-Acetylmannosamine (ManNAc), mannose, and their derivatives were used for in situ synthesis of CMP-sialic acids and derivatives. $Le^x$ trisaccharide used as the sialyltransferase acceptor was synthesized using a one-pot two-enzyme system containing a bifunctional L-fucokinase/GDP-fucose pyrophosphorylase (FKP) cloned from *Bacteroides fragilis* and a recombinant *Helicobacter pylori* α1-3-fucosyltransferase as shown previously. As shown in FIG. 9, $SLe^x$ tetrasaccharides containing natural sialic acid forms including N-acetylneuraminic acid (Neu5Ac), N-glycolylneuraminic acid (Neu5Gc), 2-keto-3-deoxy-D-glycero-D-galacto-nonulosonic acid (Kdn), as well as 9-O-acetylated Neu5Ac and Neu5Gc were obtained in excellent (85-93%) to good yields (62-64%). The relatively lower yields for the synthesis of $SLe^x$ containing the 9-O-acetyl sialic acid forms were due to the de-O-acetylation process leading to the formation of non-O-acetylated $SLe^x$ oligosaccharides. In addition, $SLe^x$ containing non-natural sialic acid forms including those with an N-azidoacetyl group or an azido group at C-5 or a C-9 azido group were also successfully obtained in excellent yields (84-91%).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. An isolated glycosyltransferase, wherein
the amino acid corresponding to position 120 of SEQ ID NO:1 is any amino acid other than M,
the amino acid corresponding to position 289 of SEQ ID NO:1 is any amino acid other than R,
wherein the glycosyltransferase has decreased α2-3 sialidase or donor substrate hydrolysis activity compared to a control glycosyltransferase, wherein the amino acid of the glycosyltransferase corresponding to position 120 of SEQ ID NO:1 is M, the amino acid corresponding to position 247 of SEQ ID NO:1 is E, and the amino acid corresponding to position 289 of SEQ ID NO:1 is R,
and wherein the glycosyltransferase is a member of the glycosyltransferase family 80 (GT80).

2. The isolated glycosyltransferase of claim 1, wherein the isolated glycosyltransferase has decreased α2-3 sialidase activity, and
the amino acid of the glycosyltransferase corresponding to position 247 of SEQ ID NO:1 is any amino acid other than E, or
the amino acid of the glycosyltransferase corresponding to position 289 of SEQ ID NO:1 is any amino acid other than R.

3. The isolated glycosyltransferase of claim 1, wherein the ratio of α2-3 sialidase activity for the control glycosyltransferase to the α2-3 sialidase activity of the isolated glycosyltransferase is at least 5:1.

4. The isolated glycosyltransferase of claim 3, wherein the ratio is at least 10:1.

5. The isolated glycosyltransferase of claim 3, wherein the ratio is at least 100:1.

6. The isolated glycosyltransferase of claim 3, wherein the ratio is at least 1000:1.

7. The isolated glycosyltransferase of claim 1, wherein the isolated glycosyltransferase comprises:
the amino acid corresponding to position 247 of SEQ ID NO:1 is any amino acid other than E, and
the amino acid corresponding to position 289 of SEQ ID NO:1 is any amino acid other than R.

8. The isolated glycosyltransferase of claim 1, wherein the isolated glycosyltransferase has decreased donor substrate hydrolysis activity, and wherein the amino acid corresponding to position 120 of SEQ ID NO:1 is any amino acid other than M.

9. The isolated glycosyltransferase of claim 8, wherein the ratio of donor substrate hydrolysis activity for the control α2-3 sialidase to the donor substrate hydrolysis activity of the isolated glycosyltransferase is at least 2:1.

10. The isolated glycosyltransferase of claim 1, wherein the amino acid corresponding to position 120 of SEQ ID NO:1 is any amino acid selected from the group consisting of V, I, L, F, W, P, S, T, A, G, C, Y, N, Q, D, E, K, R, and H.

11. The isolated glycosyltransferase of claim 1, wherein the amino acid corresponding to position 247 of SEQ ID NO:1 is any amino acid selected from the group consisting of V, I, L, M, F, W, P, S, T, A, G, C, Y, N, Q, D, K, R, and H.

12. The isolated glycosyltransferase of claim 1, wherein the amino acid corresponding to position 289 of SEQ ID NO:1 is any amino acid selected from the group consisting of V, I, L, M, F, W, P, S, T, A, G, C, Y, N, Q, D, E, K, and H.

13. The isolated glycosyltransferase of claim 1, wherein
the amino acid corresponding to position 120 of SEQ ID NO:1 is D, E, H, K or R,
the amino acid corresponding to position 247 of SEQ ID NO:1 is F, Y or W, or
the amino acid corresponding to position 289 of SEQ ID NO:1 is Y, F or W.

14. The isolated glycosyltransferase of claim 1, wherein
the amino acid corresponding to position 120 of SEQ ID NO:1 is D or H,
the amino acid corresponding to position 247 of SEQ ID NO:1 is F, or
the amino acid corresponding to position 289 of SEQ ID NO:1 is Y.

15. The isolated glycosyltransferase of claim 1, wherein the glycosyltransferase is an α2-3 sialyltransferase.

16. The isolated glycosyltransferase of claim 15, comprising a motif in the sialyltransferase domain comprising at least one member selected from the group consisting of sialyltransferase motif A (YDDGS; SEQ ID NO:31) and sialyltransferase motif B (KGH).

17. The isolated glycosyltransferase of claim 1, wherein the control glycosyltransferase is SEQ ID NO:1.

18. The isolated glycosyltransferase of claim 17, wherein the glycosyltransferase comprises a polypeptide sequence having at least 80% sequence identity to SEQ ID NO:1.

19. The isolated glycosyltransferase of claim 1, wherein the isolated glycosyltransferase comprises a polypeptide sequence selected from the group consisting of SEQ ID NO: 3 (M120D), SEQ ID NO: 5 (M120H), SEQ ID NO: 7 (E247F), SEQ ID NO: 9 (R289Y) and SEQ ID NO: 11 (E247F/R289Y).

20. A recombinant nucleic acid encoding an isolated glycosyltransferase of claim 1.

21. A cell comprising an recombinant nucleic acid of claim 20.

22. A method of preparing an oligosaccharide, the method comprising:
a) forming a reaction mixture comprising an acceptor sugar, a donor substrate comprising a sugar moiety and a nucleotide, and the glycosyltransferase of claim 1, under conditions sufficient to transfer the sugar moiety from the donor substrate to the acceptor sugar, thereby forming the oligosaccharide.

* * * * *